(12) United States Patent
Nishimuta et al.

(10) Patent No.: US 12,263,620 B2
(45) Date of Patent: Apr. 1, 2025

(54) ORTHODONTIC ALIGNER MANUFACTURING AND QUALITY ASSESSMENT SYSTEM

(71) Applicant: Align Technology, Inc., San Jose, CA (US)

(72) Inventors: James Nishimuta, Durham, NC (US); Enrique Soltero Borrego, Ciudad Juarez (MX); Enrique Jonathan Guzman Olivas, Ciudad Juarez (MX); Jun Sato, San Jose, CA (US); Kevin Daniel Rodriguez Trujillo, Ciudad Juarez (MX); Jose Kiyotaka Blanco Romo, Ciudad Juarez (MX); Erick Enriquez de Anda, Ciudad Juarez (MX); Lance Robert Pickens, Campbell, CA (US); Wesly Wong, Cupertino, CA (US); Gabriela Perez Vallejo, Ciudad Juarez (MX); Carlos Alberto Garcia Carmona, Ciudad Juarez (MX); Omar Barraza Alvarez, Ciudad Juarez (MX); Miguel Angel Hurtado Soltero, Ciudad Juarez (MX)

(73) Assignee: Align Technology, Inc., San Jose, CA (US)

( * ) Notice: Subject to any disclaimer, the term of this patent is extended or adjusted under 35 U.S.C. 154(b) by 66 days.

(21) Appl. No.: 17/990,581

(22) Filed: Nov. 18, 2022

(65) Prior Publication Data
US 2023/0158716 A1     May 25, 2023

Related U.S. Application Data

(60) Provisional application No. 63/282,576, filed on Nov. 23, 2021.

(51) Int. Cl.
    *B29C 33/38*     (2006.01)
    *B29C 51/10*     (2006.01)
    (Continued)

(52) U.S. Cl.
    CPC .......... *B29C 33/3842* (2013.01); *B29C 51/10* (2013.01); *B29C 51/268* (2013.01);
    (Continued)

(58) Field of Classification Search
    CPC .............................. A61C 7/08; B29C 33/3842
    (Continued)

(56) References Cited

U.S. PATENT DOCUMENTS 5,975,893 A     11/1999     Chishti et al.
6,210,162 B1     4/2001     Chishti et al.
(Continued)

FOREIGN PATENT DOCUMENTS

CN     214712864 U     11/2021
WO     2018005010 A1     1/2018

*Primary Examiner* — S. Behrooz Ghorishi
*Assistant Examiner* — Gregory C. Grosso
(74) *Attorney, Agent, or Firm* — Lowenstein Sandler LLP

(57) ABSTRACT

Implementations describe systems and methods for manufacturing and performing quality assessment of dental appliances. In one embodiment, a method of manufacturing a dental appliance comprises receiving, at a holder, a feature of the dental appliance, the feature comprising a first surface having a first shape, wherein the holder holds the feature of the dental appliance at a reference position. The method further includes automatically placing an object against the feature at the reference position using a robot arm, wherein the object comprises a second surface having a second shape that mates with the first shape. The method further includes applying pressure to press the object against the feature of the dental appliance and bonding the object to the feature of the dental appliance while applying the pressure.

21 Claims, 30 Drawing Sheets

(51) Int. Cl.
　　　*B29C 51/26*　　　(2006.01)
　　　*B29C 51/30*　　　(2006.01)
　　　*B33Y 10/00*　　　(2015.01)
　　　*B33Y 50/00*　　　(2015.01)
　　　*B33Y 80/00*　　　(2015.01)
　　　*A61C 7/08*　　　(2006.01)
　　　*B29L 31/00*　　　(2006.01)

(52) U.S. Cl.
　　　CPC .............. *B29C 51/30* (2013.01); *B33Y 10/00*
　　　　　(2014.12); *B33Y 50/00* (2014.12); *B33Y 80/00*
　　　　　　　(2014.12); *A61C 7/08* (2013.01); *B29L*
　　　　　　　　　　　　　　　　　　　*2031/753* (2013.01)

(58) Field of Classification Search
　　　USPC ........................................................ 156/242
　　　See application file for complete search history.

(56) References Cited

U.S. PATENT DOCUMENTS

| | | |
|---|---|---|
| 6,309,215 B1 | 10/2001 | Phan et al. |
| 6,450,807 B1 | 9/2002 | Chishti et al. |
| 6,497,574 B1 | 12/2002 | Miller |
| 6,749,414 B1 | 6/2004 | Hanson et al. |
| 6,830,450 B2 | 12/2004 | Knopp et al. |
| 6,957,118 B2 | 10/2005 | Kopelman et al. |
| 6,976,627 B1 | 12/2005 | Culp et al. |
| 7,092,784 B1 | 8/2006 | Simkins |
| 7,220,124 B2 | 5/2007 | Taub et al. |
| 7,236,842 B2 | 6/2007 | Kopelman et al. |
| 7,245,977 B1 | 7/2007 | Simkins |
| 7,261,533 B2 | 8/2007 | Wrosz et al. |
| 7,335,024 B2 | 2/2008 | Wen |
| 7,384,266 B2 | 6/2008 | Wen |
| 7,435,084 B2 | 10/2008 | Liu et al. |
| 7,472,789 B2 | 1/2009 | Wu et al. |
| 7,476,100 B2 | 1/2009 | Kuo |
| 7,481,647 B2 | 1/2009 | Sambu et al. |
| 7,604,181 B2 | 10/2009 | Culp et al. |
| 7,641,828 B2 | 1/2010 | DeSimone et al. |
| 7,648,360 B2 | 1/2010 | Kuo |
| 7,674,422 B2 | 3/2010 | Kuo |
| 7,711,447 B2 | 5/2010 | Lu et al. |
| 7,748,199 B2 | 7/2010 | Sankaran et al. |
| 7,802,987 B1 | 9/2010 | Phan |
| 7,819,659 B2 | 10/2010 | Wen |
| 7,831,322 B2 | 11/2010 | Liu et al. |
| 7,840,373 B2 | 11/2010 | Culp et al. |
| 7,892,474 B2 | 2/2011 | Shkolnik et al. |
| 7,922,490 B2 | 4/2011 | Wen |
| 7,957,824 B2 | 6/2011 | Boronvinskih et al. |
| 8,019,465 B2 | 9/2011 | Spiridonov et al. |
| 8,030,588 B2 * | 10/2011 | Culp ................... B07C 5/3412 |
| | | 209/552 |
| 8,087,932 B2 | 1/2012 | Liu |
| 8,636,513 B2 | 1/2014 | Wen |
| 8,765,031 B2 | 7/2014 | Li et al. |
| 8,776,391 B1 | 7/2014 | Kaza et al. |
| 9,108,338 B2 | 8/2015 | Sirovskiy et al. |
| 9,403,238 B2 | 8/2016 | Culp |
| 9,943,386 B2 | 4/2018 | Webber et al. |
| 9,943,991 B2 | 4/2018 | Tanugula et al. |
| 10,336,102 B2 | 7/2019 | Cole |
| 10,495,973 B2 | 12/2019 | Cole |
| 10,888,395 B2 | 1/2021 | Kopelman |
| 11,295,444 B2 | 4/2022 | Cherkas et al. |
| 11,420,362 B2 | 8/2022 | Mojdeh et al. |
| 11,511,485 B2 | 11/2022 | Mojdeh et al. |
| 11,534,277 B2 | 12/2022 | Chavez et al. |
| 2004/0243361 A1 | 12/2004 | Steuben et al. |
| 2006/0093982 A1 | 5/2006 | Wen |
| 2006/0093987 A1 | 5/2006 | Wen |
| 2006/0093993 A1 | 5/2006 | Wen |
| 2006/0127850 A1 | 6/2006 | Wen |
| 2006/0127857 A1 | 6/2006 | Zhenhuan et al. |
| 2006/0127858 A1 | 6/2006 | Wen |
| 2006/0127859 A1 | 6/2006 | Wen |
| 2006/0127860 A1 | 6/2006 | Wen |
| 2006/0172250 A1 | 8/2006 | Wen |
| 2006/0199145 A1 | 9/2006 | Liu et al. |
| 2007/0092853 A1 | 4/2007 | Liu et al. |
| 2007/0243502 A1 | 10/2007 | Wen |
| 2008/0083348 A1 | 4/2008 | Kuo et al. |
| 2009/0148814 A1 | 6/2009 | Li et al. |
| 2014/0061974 A1 | 3/2014 | Tyler |
| 2014/0265034 A1 | 9/2014 | Dudley |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007362 A1 | 1/2017 | Chen et al. |
| 2017/0007363 A1 | 1/2017 | Boronkay |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0007386 A1 | 1/2017 | Mason et al. |
| 2017/0008333 A1 | 1/2017 | Mason et al. |
| 2018/0000564 A1 * | 1/2018 | Cam ...................... A61F 5/566 |
| 2019/0102880 A1 | 4/2019 | Parpara et al. |
| 2019/0338067 A1 | 11/2019 | Liska et al. |
| 2019/0345276 A1 | 11/2019 | Liska et al. |
| 2020/0078137 A1 | 3/2020 | Chen et al. |
| 2020/0160497 A1 | 5/2020 | Shah et al. |
| 2020/0214801 A1 | 7/2020 | Wang et al. |
| 2020/0290262 A1 | 9/2020 | Aguilar Mendez et al. |
| 2021/0030516 A1 | 2/2021 | O'Leary et al. |
| 2021/0178639 A1 | 6/2021 | Lukacs et al. |

\* cited by examiner

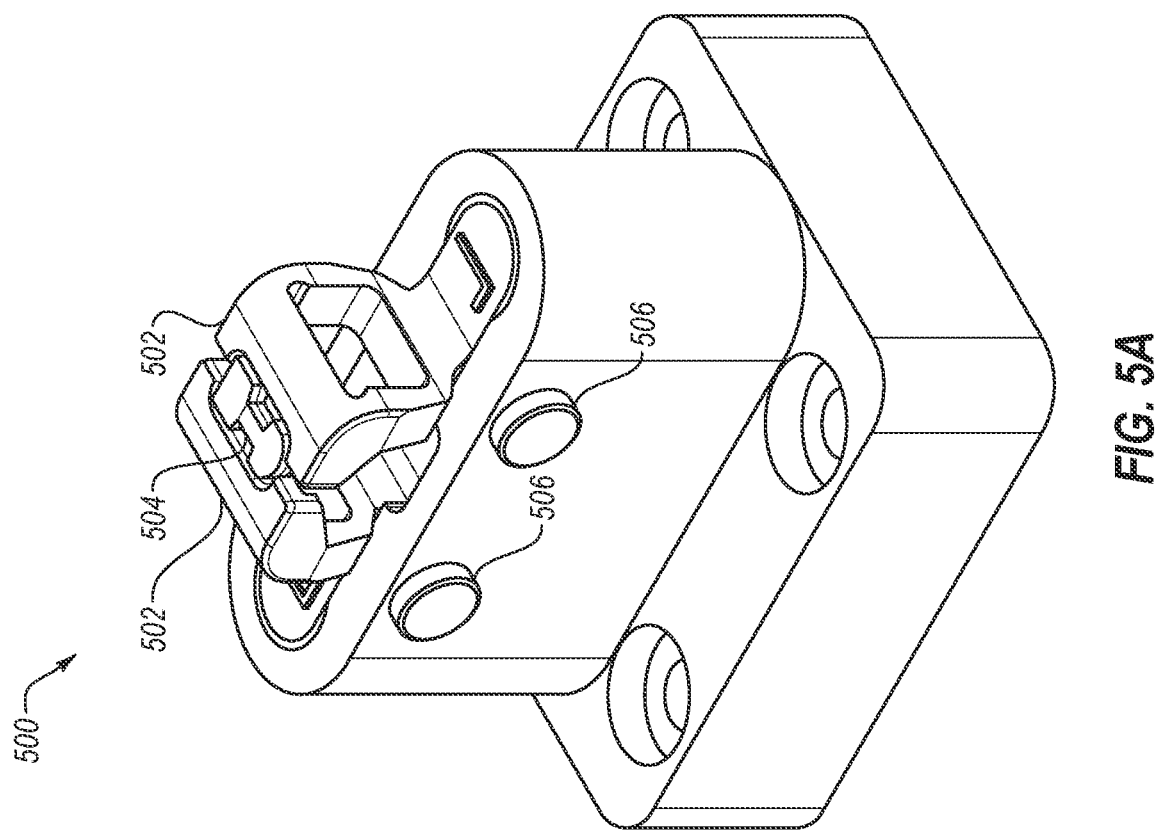

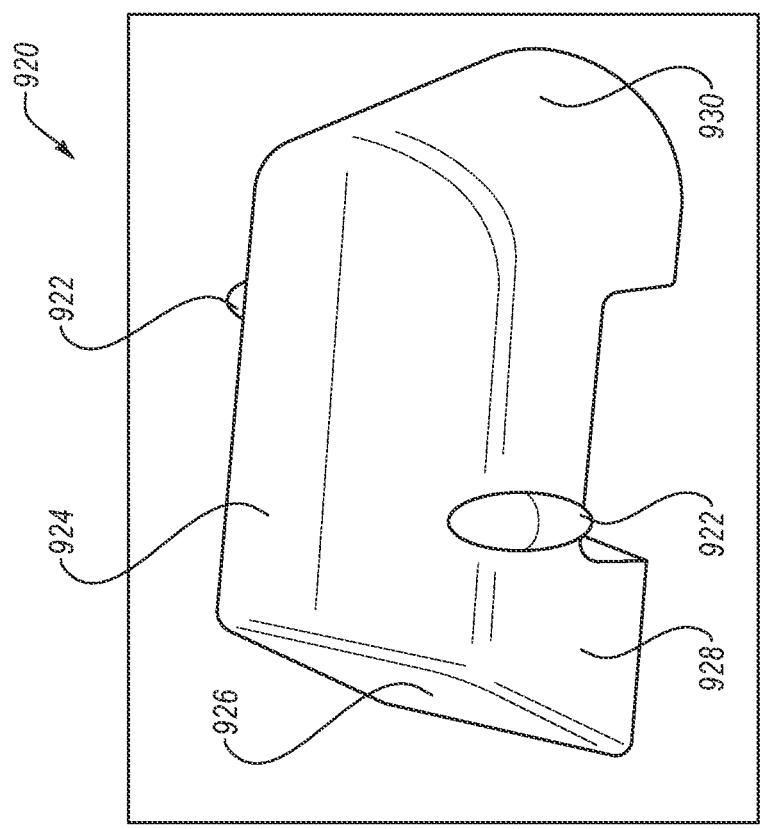
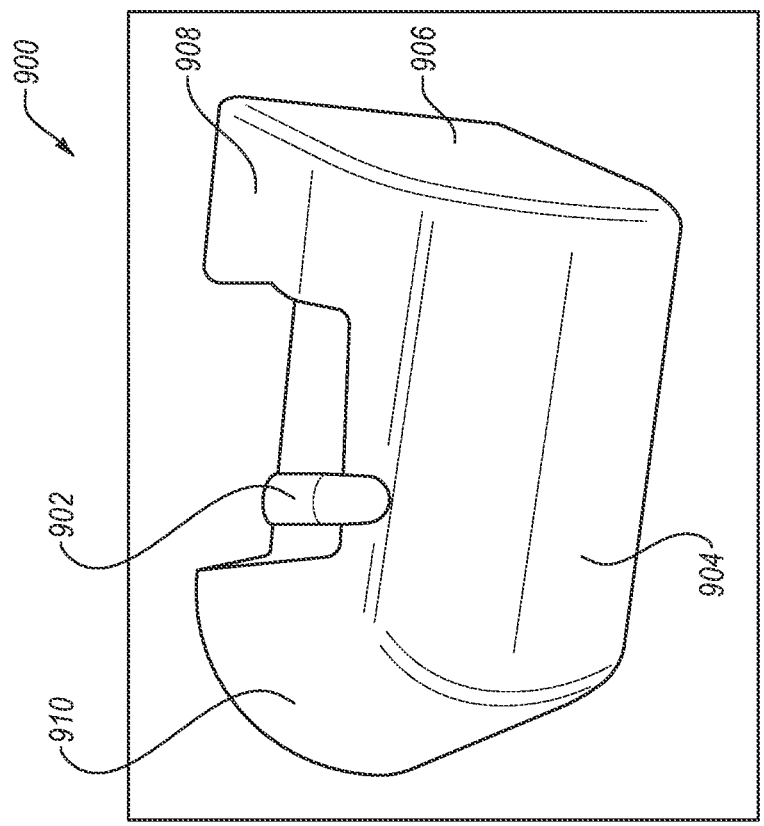
FIG. 9A
FIG. 9B

ORTHODONTIC ALIGNER MANUFACTURING AND QUALITY ASSESSMENT SYSTEM

RELATED APPLICATIONS

This application claims the benefit of U.S. Provisional Application No. 63/282,576, filed Nov. 23, 2021, the entire content of which is hereby incorporated by reference.

TECHNICAL FIELD

The present disclosure relates to the field of manufacturing custom products and, in particular, to systems and methods for manufacturing custom dental appliances such as orthodontic aligners, and performing quality inspection of such dental appliances.

BACKGROUND

For some applications, shells are formed around molds to achieve a negative of the mold. The shells are then removed from the molds to be further used for various applications. One example application in which a shell is formed around a mold and then later used is corrective dentistry or orthodontic treatment. In such an application, the mold may be a positive mold of a dental arch for a patient and the shell may be an aligner to be used for aligning one or more teeth of the patient. When attachments are used, the mold may also include features associated with planned orthodontic attachments and virtual fillers.

Molds may be formed using casting or rapid prototyping equipment. For example, 3D printers may manufacture the molds using additive manufacturing techniques (e.g., stereolithography) or subtractive manufacturing techniques (e.g., milling). The aligners may then be formed over the molds using thermoforming equipment. Once the aligner is formed, it may be manually or automatically trimmed. In some instances, a computer controlled 4-axis or 5-axis trimming machine (e.g., a laser trimming machine or a mill) is used to trim the aligner along a cutline. The trimming machine uses electronic data that identifies the cutline to trim the aligner. Thereafter, the aligner may be removed from the mold and delivered to the patient.

SUMMARY

Various implementations of the present disclosure are summarized.

In a first implementation, a method of manufacturing a dental appliance, comprises: receiving, at a holder, a feature of the dental appliance, the feature comprising a first surface having a first shape, wherein the holder holds the feature of the dental appliance at a reference position; automatically placing an object against the feature at the reference position using a robot arm, wherein the object comprises a second surface having a second shape that mates with the first shape; applying pressure to press the object against the feature of the dental appliance; and bonding the object to the feature of the dental appliance while applying the pressure.

A second implementation may further extend the first implementation. In the second implementation, the method further comprises performing the following prior to receiving the feature of the dental appliance at the holder: performing three-dimensional printing to print a mold for the dental appliance; thermoforming the dental appliance over the mold; trimming the dental appliance along a trim line; and removing the dental appliance from the mold.

A third implementation may further extend the first or second implementation. In the third implementation, the dental appliance comprises an orthodontic aligner, the method further comprising performing the following before placing the object against the feature of the orthodontic aligner: determining an aligner type of the orthodontic aligner; determining an object type to use from a plurality of object types, wherein the object type is associated with the aligner type; and automatically picking up the object having the object type using the robot arm.

A fourth implementation may further extend the third implementation. In the fourth implementation, determining the aligner type comprises: capturing an image of the feature; and processing the image.

A fifth implementation may further extend the fourth implementation. In the fifth implementation, processing the image comprises: inputting the image into a trained machine learning model, wherein the trained machine learning model outputs a classification for the orthodontic aligner that indicates the aligner type.

A sixth implementation may further extend the fourth or fifth implementation. In the sixth implementation, the feature comprises a pattern of notches and/or protrusions associated with the aligner type, wherein processing of the image is performed to identify the pattern of notches and/or protrusions of the feature, and wherein the object having the object type comprises an opposing pattern of notches and/or protrusions that mates with the pattern of notches and/or protrusions of the feature for the aligner type.

A seventh implementation may further extend any of the first through sixth implementations. In the seventh implementation, the method further comprises: capturing an image of the dental appliance in the holder prior to placing the object against the feature of the dental appliance; processing the image; and determining whether the dental appliance has a correct placement in the holder based on a result of the processing.

An eighth implementation may further extend the seventh implementation. In the eighth implementation, processing the image comprises inputting the image into a trained machine learning model, wherein the trained machine learning model generates an output indicating whether the dental appliance has the correct placement in the holder.

A ninth implementation may further extend any of the first through eighth implementations. In the ninth implementation, the method further comprises: capturing an image of the dental appliance in the holder prior to bonding the object to the dental appliance; processing the image; and determining whether the object is correctly placed against the feature of the dental appliance based on a result of the processing.

A $10^{th}$ implementation may further extend the ninth implementation. In the $10^{th}$ implementation, processing the image comprises inputting the image into a trained machine learning model, wherein the trained machine learning model generates an output indicating at least one of a) whether the object was correctly placed against the feature of the dental appliance, or b) whether the object is a correct object type for placement against the feature of the dental appliance.

An $11^{th}$ implementation may further extend the any of the first through $10^{th}$ implementations. In the $11^{th}$ implementation, bonding the object to the feature comprises laser welding the object to the feature.

A $12^{th}$ implementation may further extend the $11^{th}$ implementation. In the $12^{th}$ implementation, the object comprises a layer of a photo-thermal compound on the second surface of the object, wherein at least one of a) the dental appliance is a clear plastic dental appliance or b) the object is a clear plastic object, and wherein performing the laser welding comprises: directing coherent light having a first wavelength through at least one of the clear plastic dental appliance or the clear plastic object onto an interface of the first surface and the second surface, wherein the photo-thermal compound absorbs the coherent light having the first wavelength and generates heat that melts the object and the dental appliance at the interface of the first surface and the second surface.

A 13$^{th}$ implementation may further extend the 11$^{th}$ or 12$^{th}$ implementation. In the 13$^{th}$ implementation, the object comprises plastic impregnated with a photo-thermal compound, wherein the dental appliance is a clear plastic orthodontic aligner, and wherein performing the laser welding comprises: directing coherent light having a first wavelength through the clear plastic orthodontic aligner onto an interface of the first surface and the second surface, wherein the photo-thermal compound at the second surface absorbs the coherent light having the first wavelength and generates heat that melts the object and the dental appliance at the interface of the first surface and the second surface.

A 14$^{th}$ implementation may further extend any of the first through 13$^{th}$ implementations. In the 14$^{th}$ implementation, the method further comprises: measuring an amount of force applied to place the object against the feature of the dental appliance during the placing of the object against the feature of the dental appliance; determining whether the amount of force is between an upper force threshold and a lower force threshold; and determining whether the object has been correctly placed against the feature of the dental appliance based on whether the amount of force is between the upper force threshold and the lower force threshold.

A 15$^{th}$ implementation may further extend the 14$^{th}$ implementation. In the 15$^{th}$ implementation, the feature comprises a cavity having a narrower opening at a top of the cavity than at a bottom of the cavity, wherein placing the object against the feature causes walls of the cavity to flex outward, and wherein the walls of the cavity return to an unflexed position once the object is fully seated against the feature.

A 16$^{th}$ implementation may further extend the 14$^{th}$ or 15$^{th}$ implementation. In the 16$^{th}$ implementation, bonding the object to the feature comprises at least one of a) applying heat to activate a thermally activated solvent on the second surface of the object that forms the bond or b) exposing the dental appliance to ultraviolet radiation to cure an ultraviolet cured adhesive on the second surface of the object to form the bond.

A 17$^{th}$ implementation may further extend any of the first though 16$^{th}$ implementations. In the 17$^{th}$ implementation, the method further comprises: manufacturing the object, wherein the second surface of the object that mates with the first surface of the feature has a first average surface roughness that causes the second surface to have a target wettability, and wherein a third surface of the object that does not contact the dental appliance has a second average surface roughness that is lower than the first average surface roughness, wherein the second average surface roughness reduces at least one of absorbance or reflectance of the object to light; and coating the second surface of the object with a bonding layer, wherein the first average surface roughness facilitates an even coating of the bonding layer on second surface.

In an 18$^{th}$ implementation, a method of manufacturing a clear plastic dental appliance comprises: disposing an object within a cavity of the clear plastic dental appliance, wherein the cavity comprises a first surface having a first shape, and wherein the object comprises a second surface having a second shape that mates with the first shape; applying pressure to press the object against the cavity of the clear plastic dental appliance; and laser welding the object to the cavity of the clear plastic dental appliance while applying the pressure.

A 19$^{th}$ implementation may further extend the 18$^{th}$ implementation. In the 19$^{th}$ implementation, the method further comprises: forming the clear plastic dental appliance; wherein disposing the object within the cavity comprises inserting the object into the cavity of the clear plastic dental appliance after the clear plastic dental appliance has been formed.

A 20$^{th}$ implementation may further extend the 18$^{th}$ or 19$^{th}$ implementation. In the 20$^{th}$ implementation, forming the clear plastic dental appliance comprises thermoforming the clear plastic dental appliance over a mold.

A 21$^{st}$ implementation may further extend any of the 18$^{th}$ through 20$^{th}$ implementations. In the 21$^{st}$ implementation, the object comprises a layer of a photo-thermal compound on the second surface of the object, wherein the object is a clear plastic object, and wherein performing the laser welding comprises: directing coherent light having a first wavelength through the clear plastic object onto an interface of the first surface and the second surface, wherein the photo-thermal compound absorbs the coherent light having the first wavelength and generates heat that melts the object and the clear plastic dental appliance at the interface of the first surface and the second surface.

A 22$^{nd}$ implementation may further extend any of the 18$^{th}$ through 21$^{st}$ implementations. In the 22$^{nd}$ implementation, the method further comprises: manufacturing the object, wherein the second surface of the object that mates with the first surface of the cavity has a first average surface roughness that causes the first surface to have a target wettability, and wherein a third surface of the object that does not contact the clear plastic dental appliance has a second average surface roughness that is lower than the first average surface roughness, wherein the second average surface roughness reduces at least one of absorbance or reflectance of the object to coherent light used to perform the laser welding; and coating the second surface of the object with a photo-thermal compound, wherein the first average surface roughness facilitates an even coating of the a photo-thermal compound on second surface.

A 23$^{rd}$ implementation may further extend any of the 18$^{th}$ through 22$^{nd}$ implementations. In the 23$^{rd}$ implementation, the method further comprises: forming a mold for the clear plastic dental appliance, wherein the mold comprises an object configured to separate from the mold; thermoforming the clear plastic dental appliance over the mold, wherein the cavity forms over the mold during the thermoforming; trimming the clear plastic dental appliance along a trim line; and removing the clear plastic dental appliance from the mold, wherein the object is retained within the cavity and separates from the mold during removal of the clear plastic dental appliance from the mold.

A 24$^{th}$ implementation may further extend any of the first through 23$^{rd}$ implementations. The 24$^{th}$ implementation includes a manufacturing system that performs the operations of any of the first through 23$^{rd}$ implementations. The manufacturing system may include a holder configured to receive a feature of a dental appliance and to hold the dental appliance by clamping the feature of the dental appliance, wherein the holder holds the feature of the dental appliance at a reference position; a robot arm configured to retrieve an object and to place the object against the feature at the reference position; a press configured to apply pressure to press the object against the feature of the dental appliance while the dental appliance is held by the holder; and a laser configured to expose an interface of the dental appliance and the object to coherent light to weld the object to the feature of the dental appliance while the press presses the object against the feature of the dental appliance.

A $25^{th}$ implementation may further extend the $24^{th}$ implementation. In the $25^{th}$ implementation the manufacturing system further comprises a three-dimensional printer to print a mold for the dental appliance; thermoforming equipment to thermoform the dental appliance over the mold; and trimming equipment to trim the dental appliance along a trim line.

A $26^{th}$ implementation may further extend the $24^{th}$ or $25^{th}$ implementation. In the $26^{th}$ implementation, the manufacturing system further comprises: a camera to capture an image of the feature while the dental appliance is held in the holder; and a processing device to perform one or more of the operations of the above implementations.

A $27^{th}$ implementation may further extend any of the $24^{th}$ through $26^{th}$ implementations. In the $27^{th}$ implementation, a robot arm comprises a sensor to measure an amount of force applied to place the object against the feature of the dental appliance during placement of the object against the feature of the dental appliance; and a processing device to: determine whether the amount of force is between an upper force threshold and a lower force threshold; and determine whether the object has been correctly placed against the feature of the dental appliance based on whether the amount of force is between the upper force threshold and the lower force threshold.

In a $28^{th}$ implementation, a method of performing automated quality control for a clear plastic dental appliance comprises: capturing, by a camera, an image of an object bonded to the clear plastic dental appliance by a bond, wherein the clear plastic dental appliance comprises a mating surface shaped to fit over teeth of a patient and an occlusal surface opposite the mating surface, wherein the occlusal surface is positioned toward the camera during the capturing of the image, and wherein an interface of the object with the clear plastic dental appliance is visible in the image; processing, by a processing device, the image to determine one or more properties of the bond; determining, by the processing device, whether the one or more properties satisfy one or more criteria; and determining, by the processing device, whether the bond is a defective bond based on whether or not the one or more properties satisfy the one or more criteria.

A $29^{th}$ implementation may further extend the $28^{th}$ implementation. In the $29^{th}$ implementation, the method further comprises: determining that the one or more properties fail to satisfy the one or more criteria; and repeating a bonding process to improve the bond between the clear plastic dental appliance and the object.

A $30^{th}$ implementation may further extend the $28^{th}$ or $29^{th}$ implementation. In the $30^{th}$ implementation, the bonding process is a laser welding process, and wherein repeating the bonding process comprises: applying pressure to press the object against the clear plastic dental appliance; and laser welding the object to the clear plastic dental appliance while applying the pressure.

A $31^{st}$ implementation may further extend the $28^{th}$ through $30^{th}$ implementations. In the $31^{st}$ implementation, the one or more properties comprise at least one of a) a size of a bonded surface region or b) a ratio of the size of the bonded surface region to a size of an unbonded surface region; and the one or more criteria comprise at least one of a) a threshold size for the bonded surface region or b) a threshold ratio for the size of the bonded surface region to the size of the unbonded surface region.

A $32^{nd}$ implementation may further extend the $28^{th}$ through $31^{st}$ implementations. In the $32^{nd}$ implementation, processing the image comprises inputting the image into a trained machine learning model, wherein the trained machine learning model outputs the one or more properties of the bond, and wherein the one or more properties comprise at least one of: a) a classification of the bond as a successful bond or an unsuccessful bond; b) an indication of a size of a bonded surface region; c) an identification of the bonded surface region; d) an indication of a size of an unbonded surface region; e) an identification of the unbonded surface region; or f) an indication of a ratio of the size of the bonded surface region to the size of the unbonded surface region.

A $33^{rd}$ implementation may further extend the $28^{th}$ through $32^{nd}$ implementations. In the $33^{rd}$ implementation, the method further comprises: performing three-dimensional printing to print a mold for the clear plastic dental appliance; thermoforming the clear plastic dental appliance over the mold; trimming the clear plastic dental appliance along a trim line; removing the clear plastic dental appliance from the mold; placing the object onto or into a feature of the clear plastic dental appliance, wherein the clear plastic dental appliance comprises a feature comprising a first surface having a first shape, and wherein the object comprises a second surface having a second shape that mates with the first shape; and bonding the object to the clear plastic dental appliance.

A $34^{th}$ implementation may further extend the $28^{th}$ through $33^{rd}$ implementations. In the $34^{th}$ implementation, the method further comprises: providing illumination of the object bonded to the clear plastic dental appliance using a light source, wherein the illumination emphasizes the bond between the object and the clear plastic dental appliance.

A $35^{th}$ implementation may further extend the $28^{th}$ through $34^{th}$ implementations. In the $35^{th}$ implementation, the method further comprises: capturing, by the camera or an additional camera, an additional image of the object inserted into a cavity of the clear plastic dental appliance prior to the object being bonded to the clear plastic dental appliance; processing the additional image; and determining whether the object is correctly placed into the cavity of the clear plastic dental appliance based on a result of the processing.

A $36^{th}$ implementation may further extend the $35^{th}$ implementation. In the $36^{th}$ implementation, processing the additional image comprises inputting the additional image into a trained machine learning model, wherein the trained machine learning model generates an output indicating at least one of a) whether the object was correctly inserted into the cavity of the clear plastic dental appliance, or b) whether the object is a correct object type for insertion into the cavity of the clear plastic dental appliance.

A $37^{th}$ implementation may further extend the $28^{th}$ through $36^{th}$ implementations. In the $37^{th}$ implementation, the method further comprises: capturing, by the camera or an additional camera, an additional image of the clear plastic dental appliance prior to the object being bonded to the clear plastic dental appliance; processing the additional image to determine an appliance type of the clear plastic dental appliance; determining an object type to use from a plurality of object types, wherein the object type is associated with the appliance type; and causing the object having the object type to be inserted into a cavity in the clear plastic dental appliance.

A $38^{th}$ implementation may further extend the $37^{th}$ implementation. In the $38^{th}$ implementation, processing the additional image comprises: inputting the additional image into a trained machine learning model, wherein the trained machine learning model outputs a classification for the clear plastic dental appliance that indicates the appliance type.

A $39^{th}$ implementation may further extend the $37^{th}$ or $38^{th}$ implementations. In the $39^{th}$ implementation, the cavity comprises a pattern of notches and/or protrusions associated with the appliance type, wherein processing of the image is performed to identify the pattern of notches and/or protrusions of the cavity, and wherein the object having the object type comprises an opposing pattern of notches and/or protrusions that mates with the pattern of notches and/or protrusions of the cavity for the appliance type.

A $40^{th}$ implementation may further extend the $28^{th}$ through $39^{th}$ implementations. In the $40^{th}$ implementation, the method further comprises: capturing an image of the clear plastic dental appliance in a holder prior to bonding the object to the clear plastic dental appliance; processing the image; and determining whether the clear plastic dental appliance has a correct placement in the holder based on a result of the processing.

A $41^{st}$ implementation may further extend the $40^{th}$ implementation. In the $41^{st}$ implementation, processing the image comprises inputting the image into a trained machine learning model, wherein the trained machine learning model generates an output indicating whether the clear plastic dental appliance has the correct placement in the holder.

A $42^{nd}$ implementation may further extend any of the $28^{th}$ through $41^{st}$ implementations. In the $42^{nd}$ implementation, a quality analysis system for orthodontic aligners may perform the operations of any of the $28^{th}$ through $41^{st}$ implementations. The quality analysis system may comprise: a holder, configured to hold a clear plastic orthodontic aligner; a camera, configured to capture an image of an object bonded to the clear plastic orthodontic aligner by a bond, wherein the clear plastic orthodontic aligner comprises a mating surface shaped to fit over teeth of a patient and an occlusal surface opposite the mating surface, wherein the occlusal surface is to be positioned toward the camera during the capture of the image, and wherein the holder and camera are positioned such that an interface of the object with the clear plastic orthodontic aligner will be visible in the image; and a processing device, to: process the image to determine one or more properties of the bond; determine whether the one or more properties satisfy one or more criteria; and determine whether the bond is a defective bond based on whether or not the one or more properties satisfy the one or more criteria.

A $43^{rd}$ implementation may further extend the $42^{nd}$ implementation. In the $43^{rd}$ implementation, the quality analysis system further comprises: a light source to provide illumination of the object bonded to the clear plastic orthodontic aligner during capture of the image, wherein the illumination emphasizes the bond between the object and the clear plastic orthodontic aligner.

A $44^{th}$ implementation may further extend the $42^{nd}$ or $43^{rd}$ implementations. In the $44^{th}$ implementation, the quality analysis system further comprises: an additional camera to capture an additional image of the object and/or clear plastic orthodontic aligner.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIGS. 5A-B illustrate perspective views of holders for dental appliances, in accordance with embodiments of the present disclosure.

FIG. 9A illustrates a perspective view of a first type of object shaped for insertion into a cavity of a first type of feature of a dental appliance, in accordance with embodiments of the present disclosure.

FIG. 9B illustrates a perspective view of a second type of object shaped for insertion into a cavity of a second type of feature of a dental appliance, in accordance with embodiments of the present disclosure.

DETAILED DESCRIPTION OF THE DRAWINGS

Figure 1:
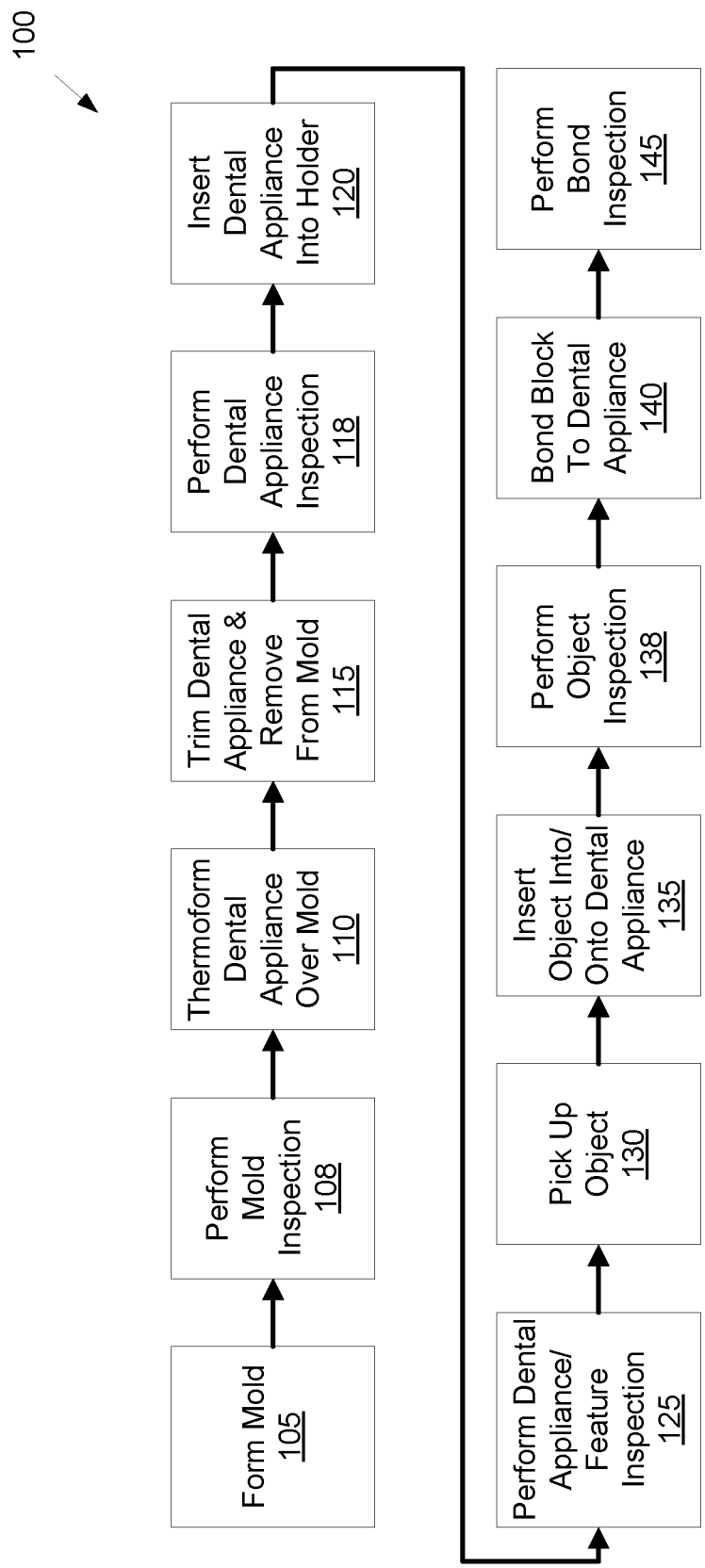
FIG. 1 illustrates a manufacturing and inspection sequence for manufacturing and inspecting a dental appliance, in accordance with embodiments of the present disclosure.

Described herein are embodiments covering systems, methods, and/or computer-readable media suitable for manufacturing of a dental appliance that includes a bonded object and performing quality analysis of one or more aspects of the dental appliance with the bonded object. Dental appliances such as orthodontic aligners may be shells thermoformed over a mold associated with a patient's dental arch. Typically, the molds over which the dental appliances are formed have a shape of a patient's dentition at a stage in treatment (e.g., at a stage in orthodontic treatment). For some types of treatment, the dental appliances are designed to have features (e.g., such as occlusal blocks) that do not correspond to a patient's dentition. A mold over which the dental appliance is formed may include a mold section for such features, which can cause the dental appliance to have one or more cavity that will not be filled by a patient's teeth. Such cavities can be weak points for the dental appliance, and can crumple or otherwise fail while the dental appliance is worn by a patient. In embodiments, objects are inserted into such cavities and bonded to the dental appliance to ensure that the objects will not separate from the dental appliance (and thus cause a choking hazard) during use.

There are numerous dental appliances (e.g., orthodontic appliances such as orthodontic aligners) that are traditionally used to correct different patient dental conditions. These various types of orthodontic appliances may be used to correct different types and severities of malocclusion (defined as abnormal alignment of the teeth and the way that the upper and lower teeth fit together). For example, orthodontic brackets (also known as braces) may be used with wires to correct some types of malocclusions. Conventional plastic orthodontic aligners may also be used to correct some types of malocclusions. However, some malocclusions may not be treatable using braces or conventional plastic orthodontic aligners. Additionally, some malocclusions may be treatable, but treatment of these malocclusions using current techniques for manufacturing plastic orthodontic aligners may introduce undesirable tradeoffs. For example, some aligner features for mandibular repositioning may have lower strength as compared to a twin block. For such malocclusions, additional orthodontic appliances that may be used on a patient include headgear, expansion appliances (e.g., a palatal expander), spacers, bite plates, Carrier® Distalizers™, functional appliances (e.g., an Andresen appliance, a Bionator, a Hawley retainer, a twin block, a Herbst appliance, a Forsus appliance, etc.), and so on. Additionally, other types of dental appliances may be used on patients for the treatment of sleep apnea and other conditions.

Current plastic aligners may introduce tradeoffs when used to correct malocclusions that are traditionally corrected through the use of some of the aforementioned additional orthodontic appliances. For example, current plastic aligners may be susceptible to crushing when used for some geometries such as large undercuts or complex features. Described herein are embodiments of manufacturing orthodontic aligners having features that enable the orthodontic aligners to apply forces to correct malocclusions that would traditionally be treated using one or more of the aforementioned additional orthodontic appliances. These features may be hollow features that would ordinarily be susceptible to being crushed. Accordingly, in embodiments cavities of the features are at least partially filled with objects that may provide structural strength to the features to prevent them from being crushed or otherwise damaged. Insertion of the objects into the hollow features may additionally or alternatively improve hygiene associated with the plastic aligner. The objects may also provide other benefits and/or perform other functions in addition to or instead of providing structural strength. The features and objects may also be used for numerous other purposes, such as jaw repositioning, to create joints in the plastic aligner, to alter mechanical properties of the plastic aligner, to alter occlusal contacts, to treat temporomandibular joint disorder (TMD), to enable linkages and/or locks to be applied to plastic aligners, to provide compliance indicators, to provide sensors, to provide buttons, and so on. In embodiments, the objects are inserted into the cavities of the features of the orthodontic aligners and a bonding process is then performed to bond the objects to the orthodontic aligners. An example bonding process that may be used is a laser welding process. Once an object is successfully bonded to an orthodontic appliance, there is no danger of the object dislodging from the orthodontic appliance and causing a choking hazard to the patient.

Also described are embodiments of a quality analysis system that can determine whether a correct object has been inserted into a cavity of a dental appliance, whether the object has been properly placed in the cavity of the dental appliance and/or whether a bond has successfully been formed between the object and the dental appliance. The process of inserting the object into/onto the dental appliance and bonding the object to the dental appliance may be a multi-stage process, some or all of which may be automated (e.g., using robotics). In embodiments, the quality analysis system performs assessments of the dental appliance and/or object (e.g., including a bond between the dental appliance and the object) at one or more of the stages of the multi-stage process. In some embodiments, one or more trained machine learning models are used to perform one or more of the assessments.

An orthodontic aligner as described herein may be included in a series of orthodontic aligners so as to provide an orthodontic system for positioning teeth. Such an orthodontic system can include a sequence of orthodontic aligners each including a shell (e.g., a plastic shell) having a one or more regions shaped to receive at least portions of teeth. The orthodontic aligners may be successively worn by a patient to move one or more teeth from a first arrangement to a second arrangement. One or more of the orthodontic aligners may include hollow features that are at least partially filled with additional objects.

Some embodiments are discussed herein with regards to orthodontic aligners. However, embodiments discussed with reference to orthodontic aligners are also applicable to other shells and/or dental appliances that are used for other purposes, such as orthodontic retainers, orthodontic splints, shells to be used as night guards, shells that are to be used to treat sleep apnea, and so on. Accordingly, it should be understood that any reference to orthodontic aligners also applies to other types of shells and/or dental appliances (e.g., other types of shells such as orthodontic retainers, orthodontic splints, or other shells that fit onto a patient's teeth but that do not reposition the patient's teeth or jaw).

Various software and/or hardware components may be used to implement the disclosed embodiments, as shown in FIGS. 1, 3-8, 10, 12A-D and 17. For example, a robot arm may be configured to pick objects and place them against features of a dental appliance, a press may be configured to press an object against a dental appliance, a robot arm may be configured to direct a laser to perform a laser weld of an object to a dental appliance, and so on. In a further example, software components may include computer instructions stored in a tangible, non-transitory computer-readable media that are executed by one or more processing devices to perform machine based analysis and/or defect detection of dental appliances with bonded objects. The software may setup and calibrate one or more cameras included in the hardware components, capture images of dental appliances and/or objects from one or more angles using the one or more cameras, setup and calibrate a light source included in the hardware components, perform analysis that determines whether an aligner has been correctly placed in a holder, whether a correct object has been placed against a feature (e.g., into a cavity of a feature) of the dental appliance, whether an object has been correctly placed against a feature of the dental appliance, whether the object has been properly bonded to the dental appliance, and so on, optionally using one or more trained machine learning models.

Referring now to the figures, FIG. 1 illustrates a manufacturing sequence 100 for manufacturing a dental appliance that includes one or more objects bonded to the dental appliance. The manufacturing sequence may begin with formation of a mold at block 105. In embodiments, the mold may be formed using one or more rapid prototyping machines. In some embodiments, the mold may be a 3D printed object fabricated using additive manufacturing techniques (also referred to herein as "3D printing"). To manufacture the mold, a shape of the mold may be determined and designed using computer aided engineering (CAE) or computer aided design (CAD) programs. In some instances, stereolithography (SLA), also known as optical fabrication solid imaging, may be used to fabricate the mold. In SLA, the object is fabricated by successively printing thin layers of a photo-curable material (e.g., a polymeric resin) on top of one another. A platform rests in a bath of liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured.

In some embodiments, the mold may be produced using other additive manufacturing techniques. Other additive manufacturing techniques may include: (1) material jetting, in which material is jetted onto a build platform using either a continuous or drop on demand (DOD) approach; (2) binder jetting, in which alternating layers of a build material (e.g., a powder-based material) and a binding material (e.g., a liquid binder) are deposited by a print head; (3) fused deposition modeling (FDM), in which material is drawn through a nozzle, heated, and deposited layer by layer; (4) powder bed infusion, including but not limited to direct metal laser sintering (DMLS), electron beam melting (EBM), selective heat sintering (SHS), selective laser melting (SLM), and selective laser sintering (SLS); (5) sheet lamination, including but not limited to laminated object manufacturing (LOM) and ultrasonic additive manufacturing (UAM); and (6) directed energy deposition, including but not limited to laser engineering net shaping, directed light fabrication, direct metal deposition, and 3D laser cladding.

The mold formed at block 105 may have the shape of a patient's dental arch and an aligner or other dental appliance may be formed over the mold. To manufacture the mold, a shape of the dental arch for the patient at a treatment stage may be determined based on a custom treatment plan. In the example of orthodontics, the treatment plan may be generated based on an intraoral scan of a dental arch to be modeled. The intraoral scan may be performed to generate a 3D virtual model of the patient's dental arch. In some instances, SLA techniques may be used to fabricate the mold of the patient's dental arch in accordance with the description above. A separate mold of the dental arch may be manufactured for each treatment stage of the patient.

Figure 2A:
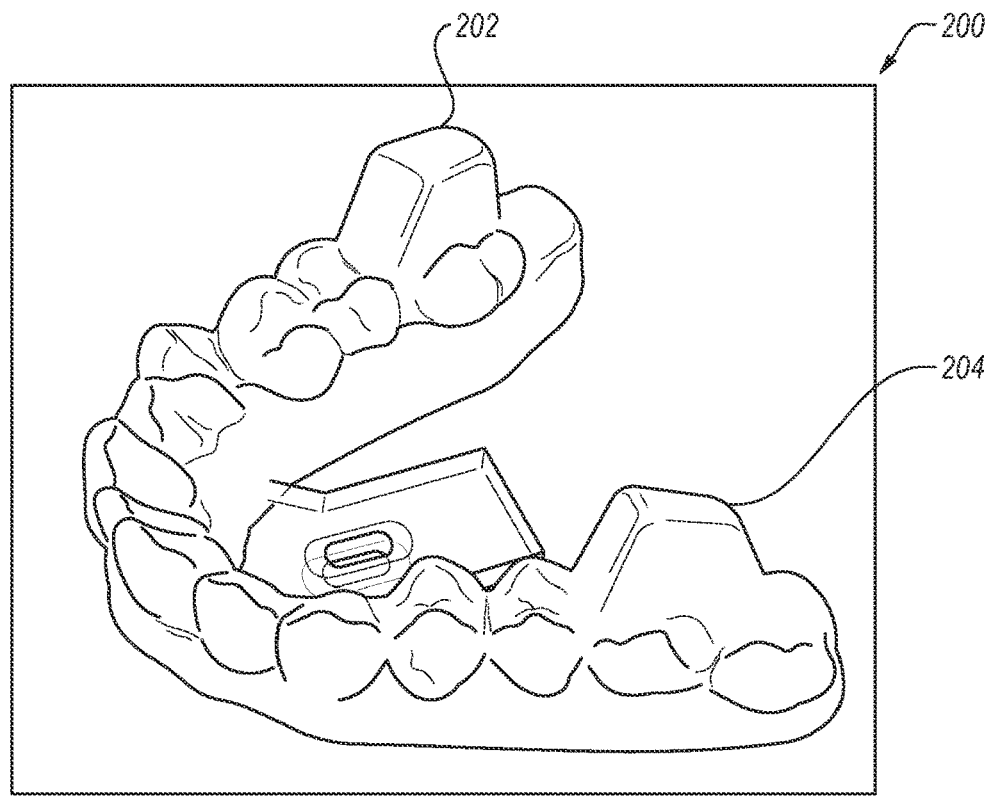
FIG. 2A illustrates a perspective view of a mold for a dental appliance, in accordance with embodiments of the present disclosure.

FIG. 2A illustrates a 3D printed mold 200 of a dental arch of a patient. As shown, in some embodiments the mold 200 includes one or more features 202, 204 that extend beyond the patient's dentition represented in the mold 200. Such features 202, 204 may be, for example, occlusal blocks or jaw positioning features. The one or more features (referred to as non-native features) may not represent a patient's teeth. Such features may be added to a digital representation of the mold that is used by a rapid prototyping machine (e.g., a 3D printer) to print the mold, and the mold may be fabricated to include the features 202, 204. Alternatively, the mold may be fabricated without the features 202, 204 and the features may be attached to the mold after the mold is manufactured.

Many different types of features may be added. Features 120 may have any imaginable shape, size, orientation, etc. that is appropriate for insertion into a patient's mouth. In some embodiments, the mold 200 may be fabricated with one or more registration features. In such embodiments the features 202, 204 may be attached to the mold via the registration features.

Returning back to FIG. 1, at block 108, the mold may optionally be inspected for defects. If the mold contains defects within its internal volume, on its surface, or on its interface, those defects may be transferred to a later formed aligner or other dental appliance formed using the mold. For example, a gap may exist between one or more thin layers of the mold as a result of a malfunction of the mold manufacturing process, causing air to become trapped within that gap. When vacuum is applied to remove trapped air during aligner manufacture, the air trapped in the gap between the thin layers of the mold may be removed and the thin layers may be forced together, closing the gap when pressure is applied to the plastic sheet. This type of defect is referred to herein as an "internal volume defect." Internal volume defects may cause a deformation of the mold of the patient's dental arch during thermoforming of the aligner, which may be transferred to the aligner formed over the deformed mold. In another example, particles (e.g., debris), may form or collect on the surface of the mold. The shape of the particles may transfer to the aligner during the thermoforming process. This type of defect is referred to herein as a "surface defect." In a further example, holes (e.g., pits) may form at the interface of the internal volume and the surface of the mold. The shape of the holes may transfer to the aligner during the thermoforming process. This type of defect is referred to herein as an "interface defect." Collectively these defects may be referred to as layering defects.

Inspection of the mold may include generating one or more images of the mold and processing the one or more images using image processing and/or a one or more trained machine learning models that has been trained to perform quality analysis of 3D printed molds. In one embodiment, the mold inspection is performed according to U.S. patent application Ser. No. 16/685,848, filed Nov. 15, 2019, which is incorporated by reference herein. For example, a mold defect detection system may include an imaging system and a computing device. The imaging system may include a platform apparatus, a top view camera apparatus, and/or a side view camera apparatus. The computing device may include an imager control module, which may send instructions to the platform apparatus, top view camera apparatus and/or side view camera apparatus to cause the defect detection system to capture images of one or more regions of the mold disposed on the platform apparatus. The captured images may be sent to the computing device, and an image inspection module on the computing device may analyze the images of the mold to determine whether any manufacturing defects (e.g., gross defects, layering defects, etc.) are present in the mold. If the mold passes inspection, then the process may proceed to block 110.

At block 110, the orthodontic aligner or other dental appliance is formed (e.g., thermoformed) over the mold. In one embodiment, a sheet of material (e.g., a polymeric or plastic sheet) is pressure formed or thermoformed over the mold. To thermoform the dental appliance over the mold, the sheet of material may be heated to a temperature at which the sheet becomes pliable. Pressure may concurrently be applied to the sheet to form the now pliable sheet around the mold. In some embodiments, vacuum is applied to remove trapped air and pull the sheet onto the mold along with pressurized air to form the sheet to the detailed shape of the mold. Once the sheet cools, it will have a shape that conforms to the mold. At block 115, the dental appliance (e.g., aligner) may be trimmed. The dental appliance may be trimmed along a cut line (e.g., a gingival cut line) in embodiments. The cut line may be specified in a digital file. A laser cutter may read the digital file to automatically cut the dental appliance along the cut line. Alternatively, the dental appliance may be manually cut along the cut line by a technician. The aligner may then be removed from the mold. Alternatively, the dental appliance may be removed from the mold prior to being trimmed.

At block 118, inspection is performed of the dental appliance. The dental appliance may have defects caused by the thermoforming process, by the trimming process, and/or by removal of the dental appliance from the mold after the thermoforming process. Such defects may include, for example, a deformation, a bend, an improper cutline, and so on. Inspection of the dental appliance may include generating one or more images of the dental appliance and processing the one or more images using image processing and/or a one or more trained machine learning models that has been trained to perform quality analysis of thermoformed dental appliances. In one embodiment, the dental appliance inspection is performed according to U.S. patent application Ser. No. 16/145,016, filed Oct. 17, 2018, which is incorporated by reference herein. For example, a dental appliance defect detection system may include an imaging system and a computing device. The imaging system may include a platform apparatus, a top view camera apparatus, and/or a side view camera apparatus. The computing device may include an imager control module, which may send instructions to the platform apparatus, top view camera apparatus and/or side view camera apparatus to cause the defect detection system to capture images of one or more regions of the dental appliance disposed on the platform apparatus. The captured images may be sent to the computing device, and an image inspection module on the computing device may analyze the images of the dental appliance to determine whether any defects are present in the dental appliance. If the dental appliance passes inspection, then the process may proceed to block 110.

Figure 2B:
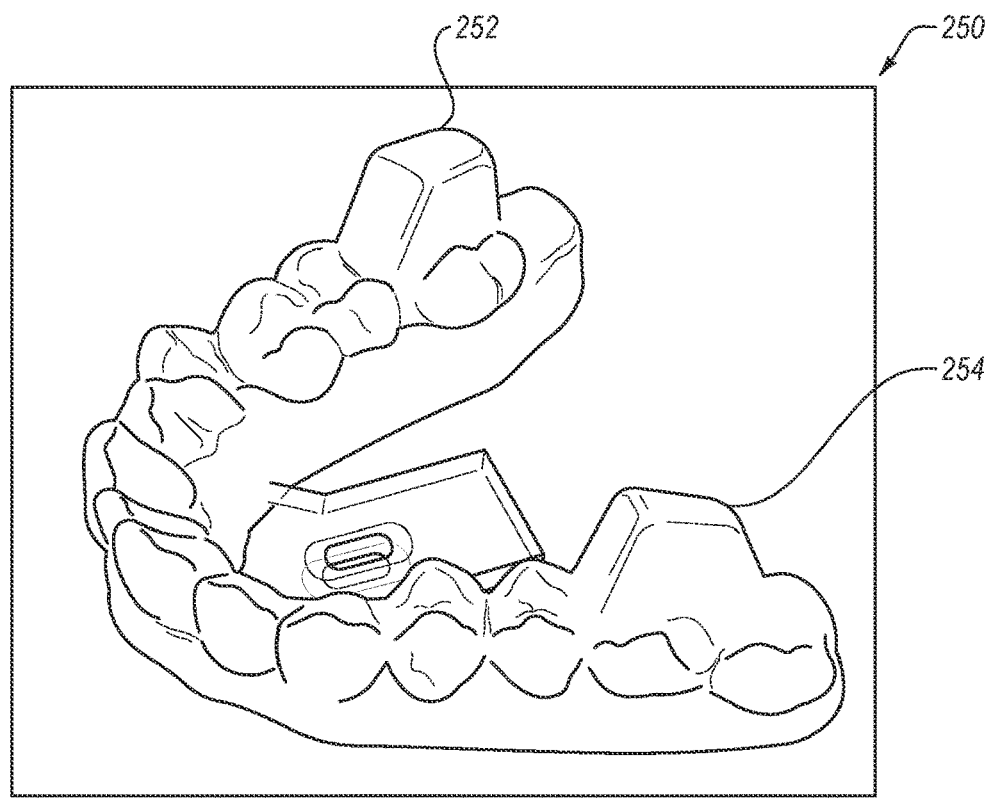
FIG. 2B illustrates a perspective view of an orthodontic appliance, in accordance with embodiments of the present disclosure.

FIG. 2B illustrates an orthodontic aligner 250 customized to reposition teeth of a patient for a stage of orthodontic treatment. The orthodontic aligner 250 is a tooth and/or jaw repositioning appliance that can be worn by a patient in order to achieve an incremental repositioning of individual teeth in the jaw. The orthodontic aligner 250 can include a shell (e.g., a translucent or clear polymeric shell) having teeth-receiving cavities that receive and resiliently reposition the teeth. As shown, in some embodiments the mold 200 includes one or more features 252, 254 (referred to as non-native features) that extend beyond the patient's dentition represented in the orthodontic aligner 250. The features 252, 254 correspond to features 202, 204 of FIG. 2A in embodiments. Such features 202, 204 may be, for example, occlusal blocks or jaw positioning features. The features 252, 254 may include large cavities that are susceptible to being crushed.

Orthodontic aligner 250 is an example tooth repositioning appliance that can be worn by a patient in order to achieve an incremental repositioning of individual teeth in the jaw. The appliance can include a shell (e.g., a continuous polymeric shell or a segmented shell) having teeth-receiving cavities that receive and resiliently reposition the teeth. An aligner or portion(s) thereof may be indirectly fabricated using a physical model of teeth. For example, an appliance (e.g., polymeric appliance) can be formed using a physical model of teeth and a sheet of suitable layers of polymeric material. A "polymeric material," as used herein, may include any material formed from a polymer. A "polymer," as used herein, may refer to a molecule composed of repeating structural units connected by covalent chemical bonds often characterized by a substantial number of repeating units (e.g., equal or greater than 3 repeating units, optionally, in some embodiments equal to or greater than 10 repeating units, in some embodiments greater or equal to 30 repeating units) and a high molecular weight (e.g., greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states. Polymers may include polyolefins, polyesters, polyacrylates, polymethacrylates, polystyrenes, polypropylenes, polyethylenes, polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers. The systems and/or methods provided herein are compatible with a range of plastics and/or polymers. Accordingly, this list is not inclusive, but rather is exemplary. The plastics can be thermosets or thermoplastics. The plastic may be thermoplastic.

Examples of materials applicable to the embodiments disclosed herein include, but are not limited to, those materials described in the following Provisional patent applications filed by Align Technology: "MULTIMATERIAL ALIGNERS," U.S. Prov. App. Ser. No. 62/189,259, filed Jul. 7, 2015; "DIRECT FABRICATION OF ALIGNERS WITH INTERPROXIMAL FORCE COUPLING", U.S. Prov. App. Ser. No. 62/189,263, filed Jul. 7, 2015; "DIRECT FABRICATION OF ORTHODONTIC APPLIANCES WITH VARIABLE PROPERTIES," U.S. Prov. App. Ser. No. 62/189,291, filed Jul. 7, 2015; "DIRECT FABRICATION OF ALIGNERS FOR ARCH EXPANSION", U.S. Prov. App. Ser. No. 62/189,271, filed Jul. 7, 2015; "DIRECT FABRICATION OF ATTACHMENT TEMPLATES WITH ADHESIVE," U.S. Prov. App. Ser. No. 62/189,282, filed Jul. 7, 2015; "DIRECT FABRICATION CROSS-LINKING FOR PALATE EXPANSION AND OTHER APPLICATIONS", U.S. Prov. App. Ser. No. 62/189,301, filed Jul. 7, 2015; "SYSTEMS, APPARATUSES AND METHODS FOR DENTAL APPLIANCES WITH INTEGRALLY FORMED FEATURES", U.S. Prov. App. Ser. No. 62/189,312, filed Jul. 7, 2015; "DIRECT FABRICATION OF POWER ARMS", U.S. Prov. App. Ser. No. 62/189,317, filed Jul. 7, 2015; "SYSTEMS, APPARATUSES AND METHODS FOR DRUG DELIVERY FROM DENTAL APPLIANCES WITH INTEGRALLY FORMED RESERVOIRS", U.S. Prov. App. Ser. No. 62/189,303, filed Jul. 7, 2015; "DENTAL APPLIANCE HAVING ORNAMENTAL DESIGN", U.S. Prov. App. Ser. No. 62/189,318, filed Jul. 7, 2015; "DENTAL MATERIALS USING THERMOSET POLYMERS," U.S. Prov. App. Ser. No. 62/189,380, filed Jul. 7, 2015; "CURABLE COMPOSITION FOR USE IN A HIGH TEMPERATURE LITHOGRAPHY-BASED PHOTOPOLYMERIZATION PROCESS AND METHOD OF PRODUCING CROSSLINKED POLYMERS THEREFROM," U.S. Prov. App. Ser. No. 62/667,354, filed May 4, 2018; "POLYMERIZABLE MONOMERS AND METHOD OF POLYMERIZING THE SAME," U.S. Prov. App. Ser. No. 62/667,364, filed May 4, 2018; and any conversion applications thereof (including publications and issued patents), including any divisional, continuation, or continuation-in-part thereof.

The dental appliance 250 can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth (e.g., may include features 252, 254). In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance in place over the teeth. In some cases, however, it may be desirable or necessary to provide individual attachments or other anchoring elements on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 3:
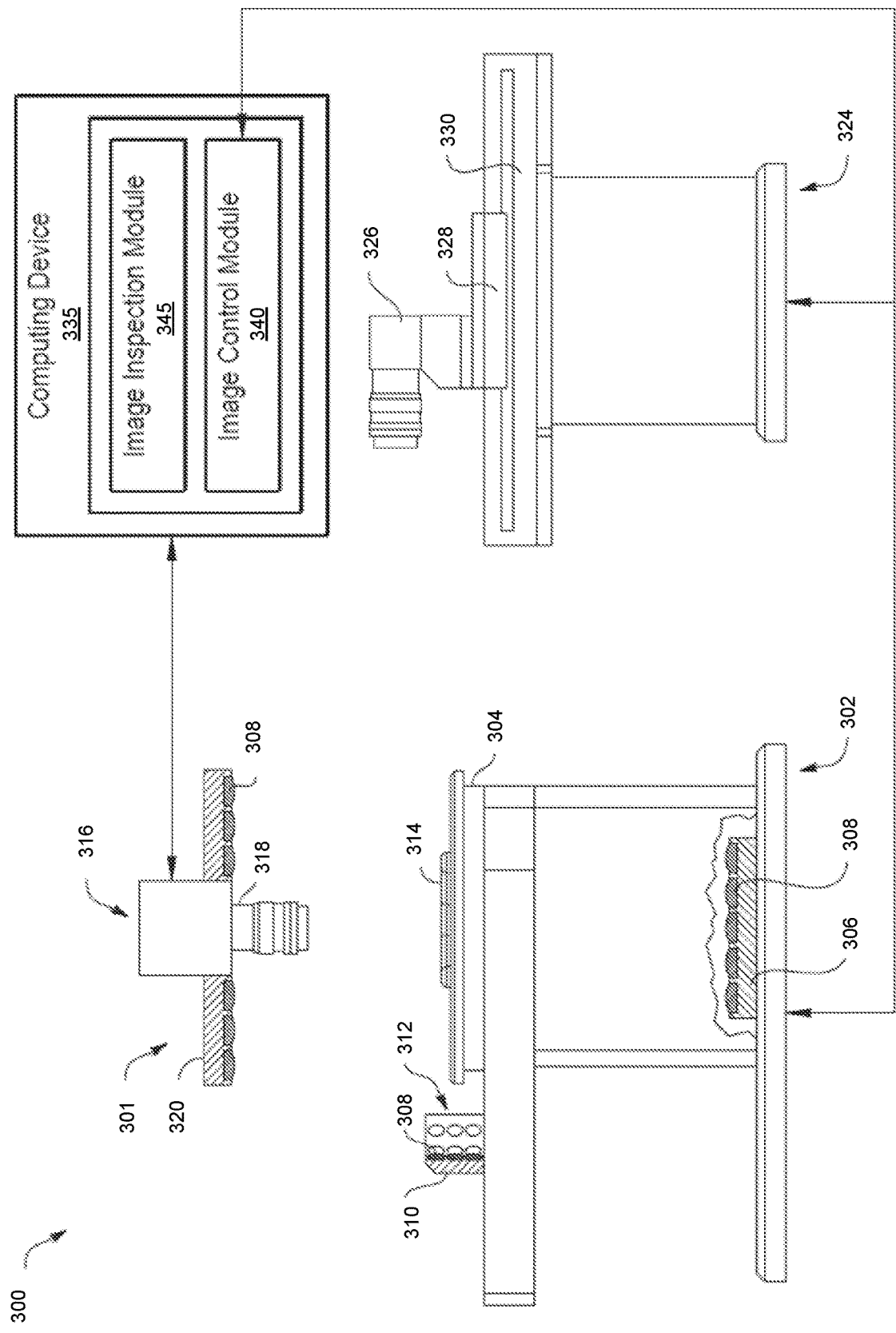
FIG. 3 illustrates a side view of an inspection station for a mold and/or dental applicant, in accordance with embodiments of the present disclosure.

FIG. 3 illustrates one embodiment of a defect detection system 300 that performs automated defect detection of an article 314. In one embodiment, the article is a mold, and the defect detection system 300 is used to perform the defect detection of the mold at block 108. In one embodiment, the article is a dental appliance (e.g., an orthodontic aligner), and the defect detection system 300 is used to perform defect detection of the dental appliance at block 118. The defect detection system 300 may include an imaging system 301 and a computing device 335. The imaging system 301 may include a platform apparatus 302, a top view camera apparatus 316, and/or a side view camera apparatus 324. The platform apparatus 302, top view camera apparatus 316 and/or side view camera apparatus 324 may be connected to computing device 335 via a wired or wireless connection. The computing device 335 may include an imager control module 340, which may send instructions to the platform apparatus 302, top view camera apparatus 316 and/or side view camera apparatus 324 to cause the defect detection system 300 to capture images of one or more regions of article 314 disposed on the platform apparatus 302. The captured images may be sent to the computing device 335, and an image inspection module 345 on the computing device 335 may analyze the images of the article 314 to determine whether any manufacturing defects (e.g., gross defects, layering defects, etc.) are present in the 3D object 314.

The platform apparatus 302 may include a platform 304. The article 314 may sit on the platform 304 while images of the article 314 are captured and subsequently processed by a processing logic. In one embodiment, the platform 304 may be a multi-axis platform. In one embodiment, the multi-axis platform includes an x-y-z-θ control, allowing the platform 304 to move along 4 axes of motion. Alternatively, the multi-axis platform may include fewer degrees of control (e.g., a θ control that causes the multi-axis platform to rotate around a z-axis). The 3D object 314 may be secured in a stationary position by a part holder, such as shown in FIGS. 4-7B, in some embodiments. Alternatively, the article 314 may rest on the platform 304 without use of a part holder. Imager control module 340 may send instructions to platform apparatus 302 to set a motion setting of the platform 304 and cause the platform 304 (and the 3D printed object disposed thereon) to move along or around at least one axis of motion (e.g., rotation and/or translational motion in the x, y, and/or z axes). In some embodiments, the platform 304 is rotated continuously while images are generated. Alternatively, the platform 304 may be rotated to a target orientation, and then rotation may be stopped while one or more images are generated. In some embodiments, one or more images are generated from a single position. In some embodiments, the platform is not moveable and/or one or more images are generated from only a single orientation/position of the platform.

The platform apparatus 302 may further include one or more light sources. The light sources may include a first light source 306 disposed beneath the platform 304, which may include a first set of one or more light emitting elements 308. Each light emitting element 308 may include at least one of an incandescent light bulb, a fluorescent light bulb, a light-emitting diode (LED), a neon lamp, and so forth. In one embodiment, the one or more of the light emitting elements 308 may emit full spectrum light. In one embodiment, one or more of the light emitting elements 308 may emit light of a particular wavelength or spectrum. For example, light emitting elements 308 may emit, red light, blue light, green light, infrared light, ultraviolet light, and so on. First light source 306 may include light emitting elements 308 that emit various different wavelengths or spectrums of light in embodiments. For example, some light emitting elements 308 may emit infrared light, while other light emitting elements may emit full spectrum light. In one embodiment, the platform 304 may be composed of a transparent material, allowing illumination from the first light source 306 below the platform to pass through the platform 304 and provide illumination of a bottom of the article 314 from underneath the article 314.

The platform apparatus 302 may further include a backing plate 310. The article 314 may be disposed between the side view camera apparatus 324 and the backing plate 310. The backing plate 310 may facilitate images of the article 314 with adequate contrast and/or lighting conditions. The backing plate 310 may include a second light source 312, wherein the second light source 312 may include a second set of one or more light emitting elements 308. The second light source 312 may provide illumination to at least one side of the 3D object 314. Second light source 312 may include light emitting elements 308 that emit various different wavelengths or spectrums of light in embodiments. For example, some light emitting elements 308 may emit infrared light, while other light emitting elements may emit full spectrum light. In one embodiment, backing plate 310 has a curved shape with a concave face that faces the platform 304 and article 314 disposed thereon.

A third light source 320 may be disposed over the platform 304, and may provide illumination on a top of the article 314. The third light source 320 may include a third set of one or more light emitting elements 308. Third light source 320 may include light emitting elements 308 that emit various different wavelengths or spectrums of light in embodiments. For example, some light emitting elements 308 may emit infrared light, while other light emitting elements may emit full spectrum light. In one embodiment, third light source 320 is a component of top view camera apparatus 316. Alternatively, third light source 320 may be a separate component, which may be connected to computing device 335.

The top view camera apparatus 316 may include a top view camera 318 that is configured to capture images of the article 314. The top view camera 318 may include a high definition camera in one embodiment. In some embodiments, the top view camera apparatus 316 may include one or more cameras that capture a wide field of view of the article. The top view camera 318 may be a two-dimensional camera or a 3D camera (e.g., a pair of cameras that generate a stereo image pair, a camera and associated structured light projector that shines a structured light pattern onto the article 314, and so on). The top view camera 318 may be configured to acquire top view images of the article 114 using certain illumination settings to enable the article 314 to be visible in a top view image. In one embodiment, the top view camera 318 has a fixed position. Alternatively, the top view camera 318 may be a movable camera. For example, the top view camera 318 may be moveable in the x, y and z directions and/or may rotate about one or more axes. Imager control module 340 may send instructions to top view camera apparatus 316 to set a zoom setting of the top view camera 318, to set an angle of the top view camera 318, to set a position of the top view camera 318, and so on. Instructions from the imager control module 340 may also cause the top view camera 318 to generate one or more images of the article 314.

The side view camera apparatus 324 may include a side view camera 326 that is configured to capture images of the article 314. The side view camera 326 may be a two-dimensional camera or a 3D camera (e.g., a pair of cameras that generate a stereo image pair, a camera and associated structured light projector that shines a structured light pattern onto the article 314, and so on). In one embodiment, the side view camera is a high resolution camera and/or a high speed camera (e.g., capable of capturing an image up to every millisecond. The side view camera 326 may acquire a single image or multiple images of different regions of the article by moving (e.g., by rotation and/or translational motion) the article 314 using the multi-axis platform, which may be directed via the x-y-z-θ controls, and generating images at different rotation and/or translational motion settings of the multi-axis platform.

The side view camera 326 may be attached to a moveable base 328. Alternatively, the side view camera may be at a fixed position, or may be on a different type of base (which may or may not be movable). The moveable base 328 may allow the side view camera 326 to move towards and away from the article 314, thus allowing the side view camera 326 to capture images of the article 314 from different perspectives. The moveable base 328 may be connected to a platform 330, which guides the moveable base 328 towards and away from the article 314. In one embodiment, the platform 304 (and article 314 disposed thereon) may be stationary, and the side view camera 326 may be movable around the platform 304 (e.g., on a track that wholly or partially circumscribes the platform 304). In one embodiment, the platform 304 is a multi-axis platform and the side view camera 326 is movable around the platform 304. In one embodiment, the side view camera 326 may capture multiple images and/or a video of the article 314 as it moves with the platform 304. The video may include multiple frames, where each frame may be an image of a distinct region of the article 314. Imager control module 340 may send instructions to side view camera apparatus 324 to set a zoom setting of the side view camera 326, to set an angle of the side view camera 326, to set a position of the side view camera 326, and so on. Instructions from the imager control module 340 may also cause the side view camera 326 to generate one or more images of the article 314.

Image control module 140 may cause the top view camera 118 and/or side view camera 126 to capture images of the 3D object 314. In one embodiment, a illumination may be provided to the article 314 by at least one of the first light source 306, the second light source 312, and/or the third light source 320. The generated image or images may be send to computing device 335. Once computing device 335 receives an image of the article 314, the image may be processed by image inspection module 345 to determine whether the article 314 includes any defects. In one embodiment the image (or images) may be input into a trained machine learning module of the image inspection module 345 that has been trained to identify defects in images of molds and/or dental appliances. The machine learning model then outputs an indication of any defects in the article 314.

Returning back to FIG. 1, at block 120 the dental appliance is inserted into a holder. The holder may be a specially designed holder that is configured to grasp one or more features having specific shapes. Alternatively, the holder may be a universal holder that can hold multiple features having different shapes. In one embodiment, different holders are configured for holding different types of features. For example, a first holder may be configured to hold features having a first shape that are used for upper dental arches, and a second holder may be configured to hold features having a second shape that are used for lower dental arches.

Figure 4:
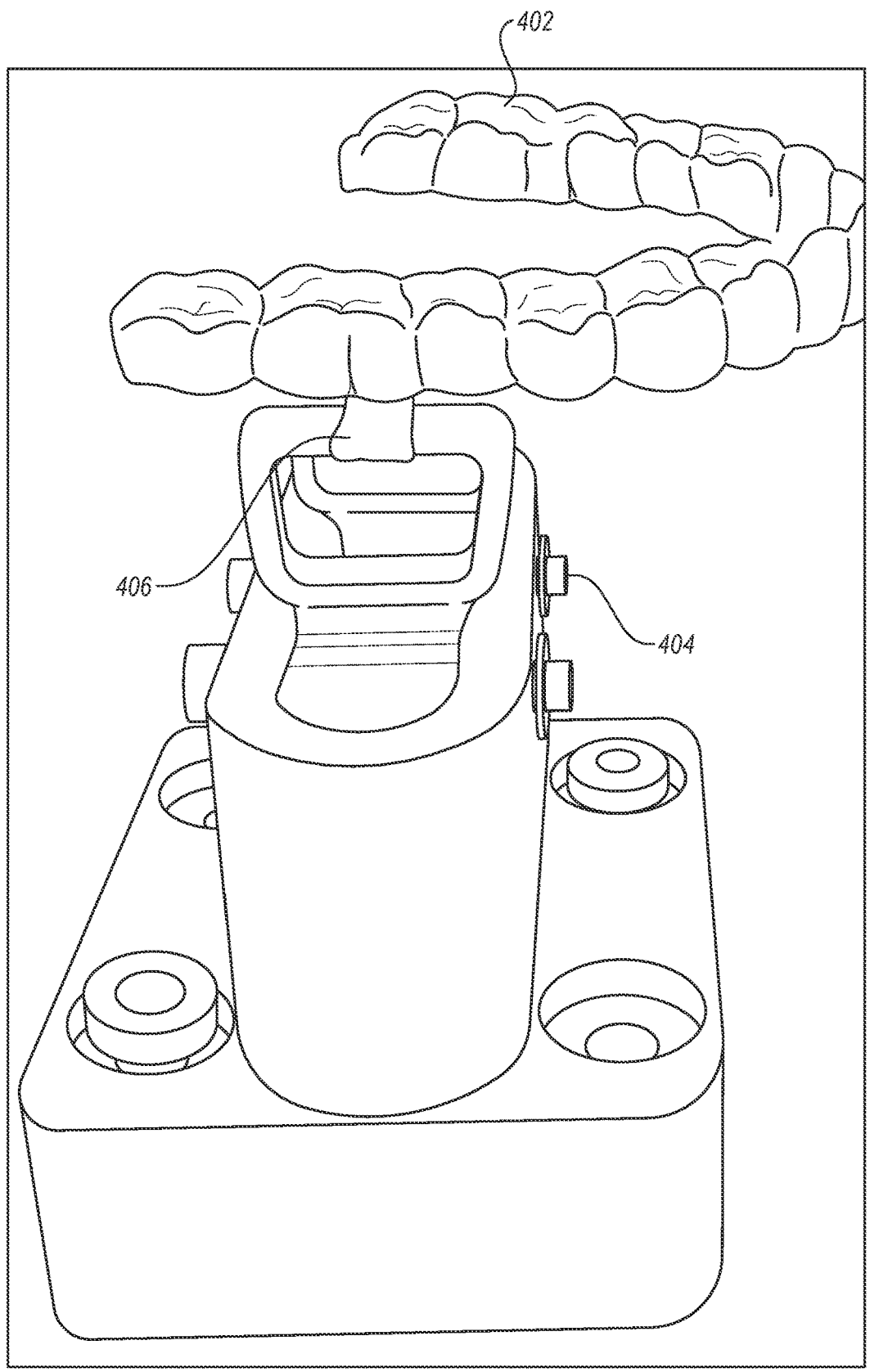
FIG. 4 illustrates a perspective view of a dental appliance inserted into a holder, in accordance with embodiments of the present disclosure.

FIG. 4 illustrates a perspective view of a dental appliance 402 inserted into a holder 404, in accordance with embodiments of the present disclosure. In particular, a feature 406 of the dental appliance 402 is inserted into the holder 404. The holder 404 may be configured to receive features at a particular orientation. For example, feature 406 may have a first shape, size and/or angle on a first side and a second shape, size and/or angle on a second side. Jaws of the holder 404 may be shaped to receive the feature having the first side with the first shape, size and/or angle and the second side with the second shape, size and/or angle in a set orientation. In some embodiments, the holder 404 will not receive the feature 406 except in the correct orientation. In some embodiments, when the feature 406 is correctly placed into the holder 404, a plane defined by the arch of the dental appliance 402 is approximately parallel to a plane defined by a surface on which the holder 404 is placed. If the feature 406 is incorrectly placed into the holder 404, then the plane defined by the arch of the dental appliance 402 may not be parallel to the surface onto which the holder 404 is placed (e.g., a plane defined by a platform or table supporting the holder 404.

Figure 5B:
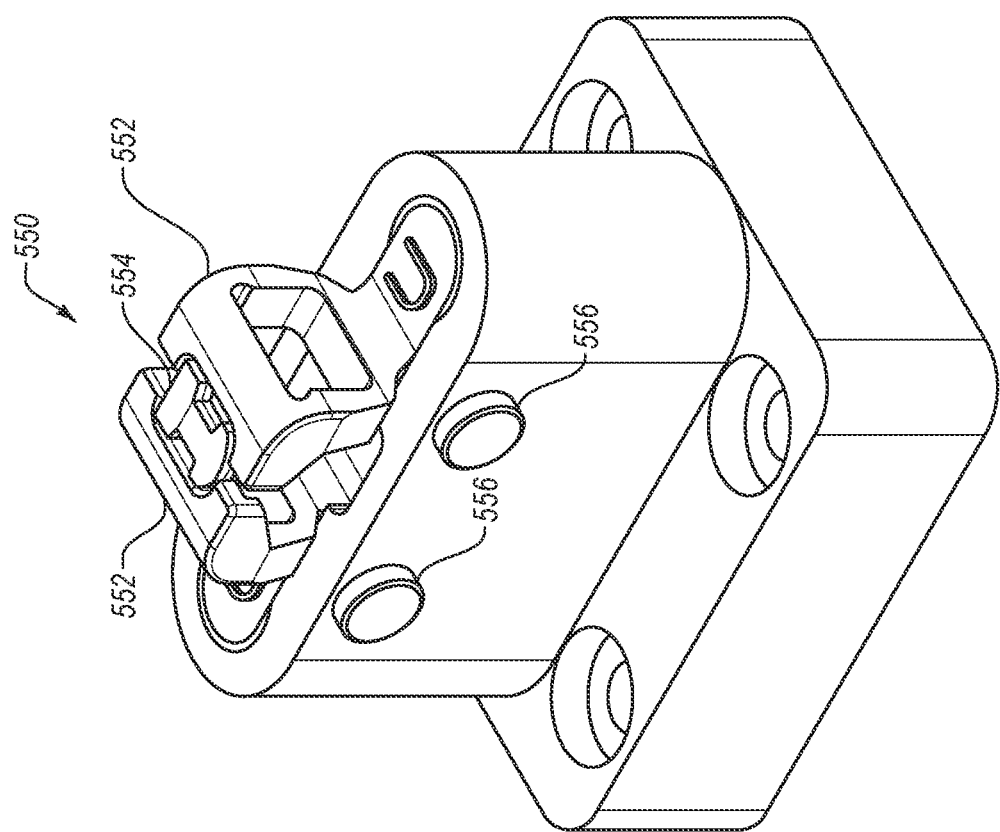

FIGS. 5A-B illustrate perspective views of holders 500, 550 for dental appliances, in accordance with embodiments of the present disclosure. In one embodiment, holder 500 is a lower holder for holding dental appliances that will be used on a lower dental arch and holder 550 is an upper holder for holding dental appliances that will be used on an upper dental arch. Each of the holders 500, 550 includes a pair of jaws 502, 552. Each of jaws 502 pivot about a respective axis 506. Similarly, each of jaws 552 pivot about a respective axis 556. The jaws 502, 552 may be spring loaded such that a spring forces the jaws closed. A feature 504 of a dental appliance for a lower dental arch may be inserted into the jaws 502 of holder 500. The jaws 502 may have a first shape configured to receive and hold the feature 504. Similarly, feature 554 of a dental appliance for an upper dental arch may be inserted into the jaws 552 of holder 550. The jaws 552 may have a second shape configured to receive and hold the feature 554. The jaws 502, 552 may apply a sufficient clamping force to the respective feature 504, 554 to secure the feature and the dental appliance that includes the feature. In the illustrated example the features 504, 554 are shown without the remainder of the dental appliance that would include the feature.

Figure 6A:
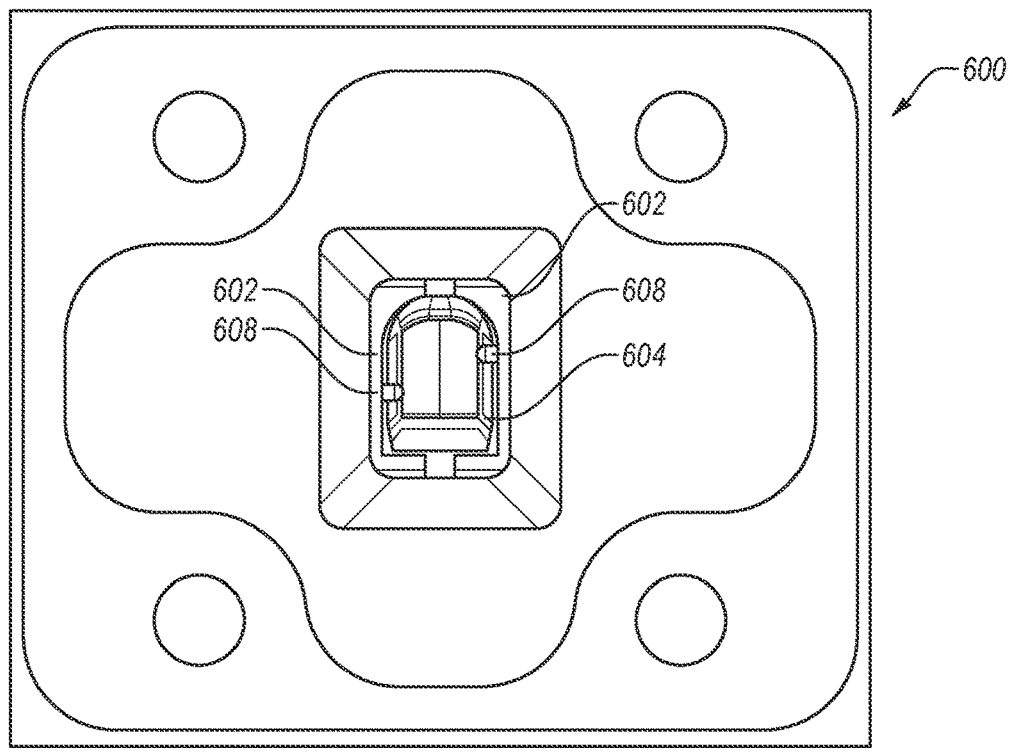
FIG. 6A illustrates a bottom view of a holder for dental appliances with a first type of feature, in accordance with embodiments of the present disclosure.
Figure 6B:
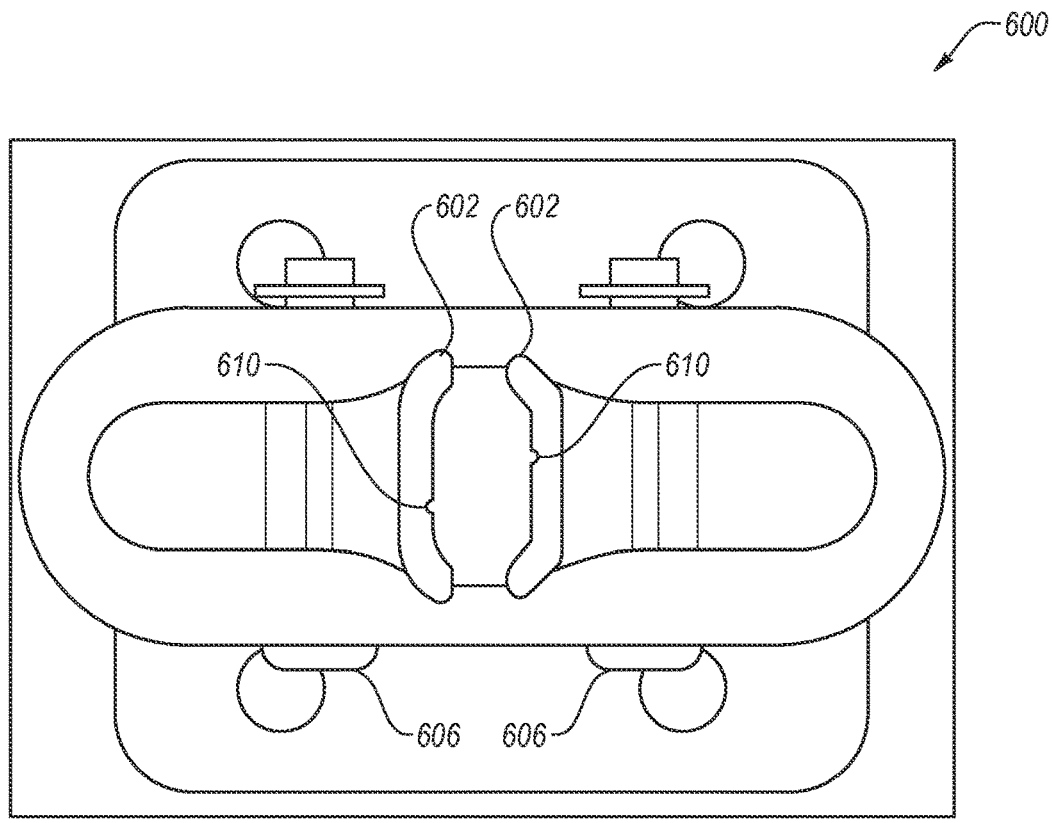
FIG. 6B illustrates a top view of the holder of FIG. 6A, in accordance with embodiments of the present disclosure.

FIG. 6A illustrates a bottom view of a holder 600 for dental appliances holding a first type of feature 604, in accordance with embodiments of the present disclosure. FIG. 6B illustrates a top view of the holder 600 of FIG. 6A, in accordance with embodiments of the present disclosure. In embodiments, holder 600 corresponds to holder 500 of FIG. 5. As shown, holder 600 includes jaws 602 that pivot about axes (e.g., provided by pins) 606. In one embodiment, each type of feature (e.g., feature 604) includes a notch and/or projection pattern (e.g., projection pattern 608) that is unique to that type of feature. In one embodiment, jaws 604 include a matching projection and/or notch pattern (e.g., notch pattern 610) that mates with the notch and/or projection pattern (e.g., projection pattern 608) of the feature 604. In such embodiments, if the wrong type of feature is inserted into the holder, then the notch/projection pattern of the feature fails to align with the projection/notch pattern of the jaws. As shown, feature 604 includes a first projection pattern 608 that matches a first notch pattern 610 of jaws 602 of holder 600.

Figure 7A:
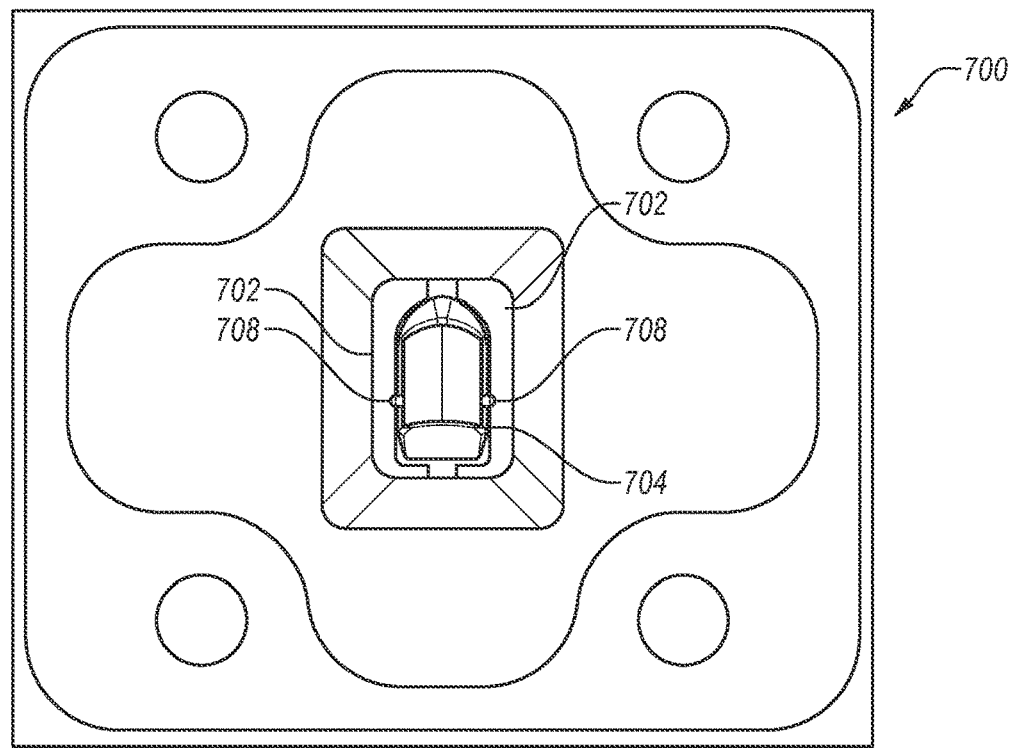
FIG. 7A illustrates a bottom view of a holder for dental appliances with a second type of feature, in accordance with embodiments of the present disclosure.
Figure 7B:
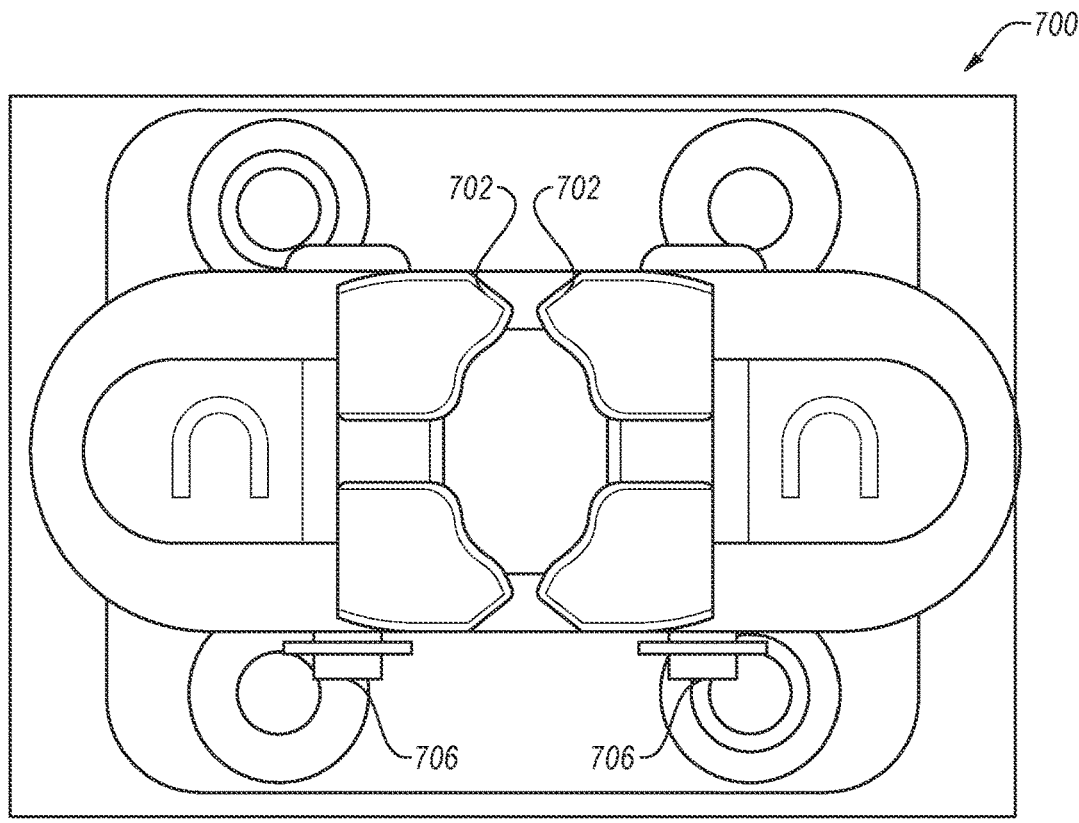
FIG. 7B illustrates a top view of the holder of FIG. 7A, in accordance with embodiments of the present disclosure.

FIG. 7A illustrates a bottom view of a holder 700 for dental appliances with a second type of feature 704, in accordance with embodiments of the present disclosure. FIG. 7B illustrates a top view of the holder 700 of FIG. 7A, in accordance with embodiments of the present disclosure. In embodiments, holder 700 corresponds to holder 550 of FIG. 5. As shown, holder 700 includes jaws 702 that pivot about axes (e.g., provided by pins) 706. In one embodiment, each type of feature (e.g., feature 704) includes a notch and/or projection pattern (e.g., projection pattern 708) that is unique to that type of feature. In one embodiment, jaws 704 include a matching projection and/or notch pattern that mates with the notch and/or projection pattern (e.g., projection pattern 708) of the feature 704. In such embodiments, if the wrong type of feature is inserted into the holder, then the notch/projection pattern of the feature fails to align with the projection/notch pattern of the jaws. As shown, feature 704 includes a second projection pattern 708 that matches a second notch pattern (not shown) of jaws 702 of holder 700.

Returning back to FIG. 1, at block 125 aligner inspection and/or feature inspection is performed on the dental appliance in the holder. In one embodiment, the holder and held dental appliance are moved to an inspection station. In one embodiment, the holder and held dental appliance are automatically moved to the inspection station, such as via a conveyor (e.g., a conveyor belt). The holder with the dental appliance may be positioned at an inspection station when the dental appliance is inserted into the holder. Alternatively, the holder with the dental appliance may be moved to an inspection station after the dental appliance has been inserted into the holder.

In one embodiment, the inspection station includes one or more camera that generates one or more images of the dental appliance in the holder. The image or images may be processed to determine whether the dental appliance was properly inserted into the holder. This may include inputting the image or images into a trained machine learning model trained to determine whether the dental appliance has a proper placement in the holder. Additionally, or alternatively, the image or images may be processed to determine a dental appliance type (e.g., aligner type) for the dental appliance that has been inserted into the holder. Dental appliance types may include, for example, a dental appliance for an upper dental arch or a dental appliance for a lower dental arch. Dental appliance type may alternatively include a dental appliance with short occlusal blocks for an upper dental arch, a dental appliance with tall occlusal blocks for the upper dental arch, a dental appliance with short occlusal blocks for the lower dental arch, or a dental appliance with tall occlusal blocks for the lower dental arch. In one embodiment, the image or images are input into a trained machine learning model that outputs an identity of the dental appliance.

Figure 8:
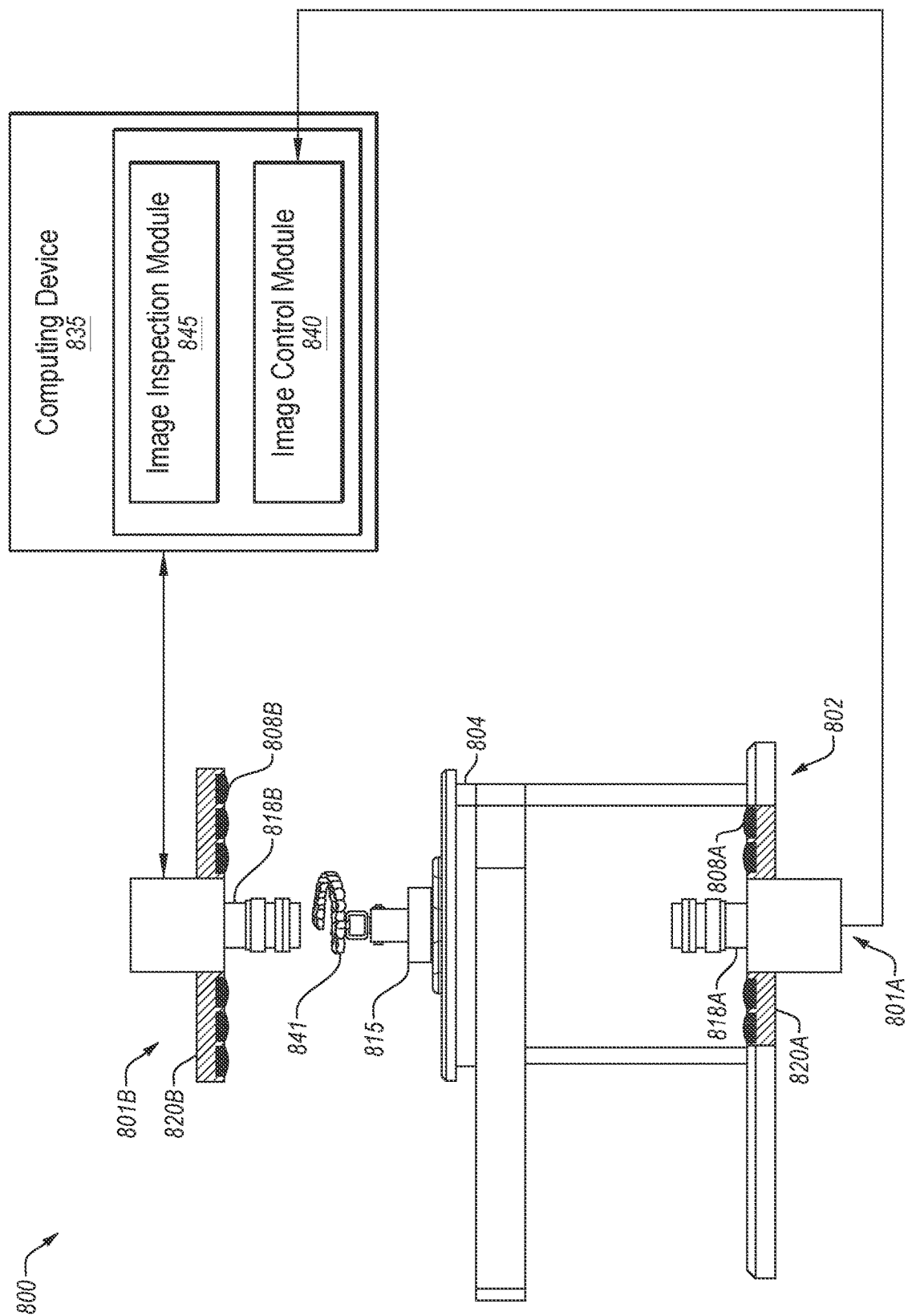
FIG. 8 illustrates a side view of an inspection station for a feature of a dental appliance inserted into a holder, in accordance with embodiments of the present disclosure.

FIG. 8 illustrates a side view of an inspection station 800 for a dental appliance 814 inserted into a holder 815, in accordance with embodiments of the present disclosure. The inspection system 800 may be used to perform the operations of block 125 in embodiments. Alternatively, the inspection system 300 of FIG. 3 may be used to perform the operations of 125 in embodiments.

The inspection station 800 may include one or more imaging system 801A-B, a platform apparatus 802 and a computing device 835. The platform apparatus 802 may include a platform 804. The holder 815 may sit on the platform 804 while images of the dental appliance 814 are captured and subsequently processed by a processing logic. In one embodiment, the platform 804 may be a multi-axis platform. In one embodiment, the multi-axis platform includes an x-y-z-θ control, allowing the platform 804 to move along 4 axes of motion. Alternatively, the multi-axis platform may include fewer degrees of control (e.g., a θ control that causes the multi-axis platform to rotate around a z-axis). Holder 814 may correspond to holder 500, holder 550, holder 600, or holder 700 in embodiments. In some embodiments, the platform 804 is not moveable.

In one embodiment, the inspection station 800 includes a lower imaging system 801A and lacks an upper imaging system 801B. In such an embodiment, a backing plate (not shown) may be positioned at the location shown for the upper imaging system 801B. The backing plate may have a color (e.g., white or black) that provides contrast and emphasizes features of the dental appliance during imaging. In one embodiment, the backing plate includes one or more light sources that provide a backlight to emphasize features of the dental appliance. The lower imaging system 801A may be positioned beneath the holder and dental appliance, and thus may be out of the way and enable easy access to the holder 815 for a robot arm. Thus, the robot arm can have access to the dental appliance without any danger of a collision with the upper imaging system 801B. In one embodiment, the holder 815 includes a channel that enables imaging of at least the held feature of the dental appliance through the holder 815 by the lower imaging system 801A. The channel may be hollow or filled with a transparent medium such as quartz or clear plastic.

In one embodiment, the inspection station 800 includes the upper imaging system 801B and lacks the lower imaging system 801A. In such embodiments, a robot arm may maneuver around the upper imaging system 801B, the upper imaging system 801B may be moveable, and may be moved out of the way when the robot arm is to gain access to the dental appliance, or the upper imaging system 801B may be positioned out of the way so that it does not interfere with operation of the robot arm. For example, the upper imaging system 801B may be positioned at an angle other than 90 degrees to the holder so that it generates a skewed image of the dental appliance in the holder. In such an embodiment, a backing plate (not shown) may be positioned at the location shown for the lower imaging system 801A. The backing plate may have a color (e.g., white or black) that provides contrast and emphasizes features of the dental appliance during imaging. In one embodiment, the backing plate includes one or more light sources that provide a backlight to emphasize features of the dental appliance. In one embodiment, the inspection station 800 includes both the upper imaging system 801B and the lower imaging system 801A.

The lower imaging system 801A may include a bottom view camera 818A and a light source 820A including one or more light emitting elements 808A. The bottom view camera 818A may be configured to acquire bottom view images of the dental appliance 814 in the holder 815 using certain illumination settings to enable the dental appliance 814 to be visible in a bottom view image. In one embodiment, the bottom view camera 818A has a fixed position. Alternatively, the bottom view camera 818A may be a movable camera. For example, the bottom view camera 818A may be moveable in the x, y and/or z directions and/or may rotate about one or more axes. Image control module 840 may send instructions to lower imaging system 801A to set a zoom setting of the bottom view camera 818A, to set an angle of the bottom view camera 818A, to set a position of the bottom view camera 818A, and so on. Instructions from the image control module 840 may also cause the bottom view camera 818A to generate one or more images of the dental appliance 814 held by holder 815.

The upper imaging system 801B may include a top view camera 818B and a light source 820B including one or more light emitting elements 808B. The top view camera 818B may be configured to acquire top view images of the dental appliance 814 in the holder 815 using certain illumination settings to enable the dental appliance 814 to be visible in a top view image. In one embodiment, the top view camera 818B has a fixed position. Alternatively, the top view camera 818B may be a movable camera. For example, the top view camera 818B may be moveable in the x, y and/or z directions and/or may rotate about one or more axes. Image control module 840 may send instructions to upper imaging system 801B to set a zoom setting of the top view camera 818B, to set an angle of the top view camera 818B, to set a position of the top view camera 818B, and so on. Instructions from the image control module 840 may also cause the top view camera 818B to generate one or more images of the dental appliance 814 held by holder 815.

The computing device 835 may include an image control module 840, which may send instructions to the platform apparatus 802, lower imaging system 801A and/or upper imaging system 801B to cause the camera 818A and/or camera 818B to capture one or more images of dental appliance 814 held by holder 815. The captured images may be sent to the computing device 835, and an image inspection module 845 on the computing device 835 may analyze the images to determine whether the dental appliance 814 is properly disposed on the holder 815 and/or to determine a dental appliance type of the dental appliance 814.

Returning back to FIG. 1, processing logic may determine an object type for an object to be placed against a feature of the dental appliance (e.g., inserted into a cavity of a feature of the dental appliance). Each object type may have a different shape in embodiments. Each dental appliance type may include features that are shaped to receive a particular object type having a particular shape. In one embodiment, the object type is determined based on the dental appliance type determined at block 125. In one embodiment, the feature of each dental appliance includes a pattern of notches and/or projections that unique to that type of dental appliance. Image processing and/or machine learning may have been performed at block 125 to determine the dental appliance type, and an object type may then be determined that corresponds to the dental appliance type.

FIG. 9A illustrates a perspective view of a first type of object 900 shaped for insertion into a cavity of a first type of feature of a first type of dental appliance, in accordance with embodiments of the present disclosure. As shown, the object 900 includes a first pattern of projections 902 that identifies a first object type for object 900.

FIG. 9B illustrates a perspective view of a second type of object shaped for insertion into a cavity of a second type of feature of a second type of dental appliance, in accordance with embodiments of the present disclosure. As shown, the object 920 includes a second pattern of projections 922 that identifies a second object type for object 920.

In some embodiments, object 900 and object 920 are clear plastic (e.g., polymeric) objects. In some embodiments, a first surface 904, 924 of the objects 900, 920 that will interface with a second surface of a feature of a dental appliance is coated with a bonding agent (also referred to as a bonding layer) to facilitate a bond between the first surface 904, 924 of the object 900, 920 and the second surface of the feature of the dental appliance. In one embodiment, the bonding agent is a photo-thermal compound. One example of a photo thermal compound that may be used is Clear-Weld®. In such embodiments, plastics laser welding may be performed by directing coherent light having a target wavelength (e.g., in the infrared part of the spectrum) through the dental appliance and/or the object onto an interface of the object and the dental appliance. The photo thermal compound absorbs the light, and the coherent light causes the photo thermal compound to heat up and melt the object and the dental appliance at the interface of the object and the dental appliance, which results in a weld between the object and the dental appliance. Use of the photo thermal compound combined with laser welding results in no particulates, no vibration or surface marring, and strong, hermetic welds formed at high speed as compared to other bonding techniques such as adhesive bonding, solvent bonding, ultrasonic bonding, vibration bonding, and hot-plate weld bonding techniques. However, in some embodiments, any of these other bonding techniques may alternatively be used to bond the object to the dental appliance. In one example, the bonding layer is a thermally activated solvent and bonding is achieved by applying heat to activate the thermally activated solvent on the first surface. In one example, the bonding layer is an ultraviolet cured adhesive and bonding is achieved by applying ultraviolet light to cure the ultraviolet cured adhesive on the first surface.

In one embodiment, the first surface 904, 924 of the object 900, 920 is a rough surface. The rough surface may improve a wettability (e.g., wetting) of the first surface 904, 924. The improved wettability of the first surface 904, 924 improves a uniformity of the photo thermal compound coated on the first surface 904, 924.

In some embodiments, other surfaces 906, 908, 910, 926, 928, 930 of the object 900, 920 are smooth surfaces. For example, in one embodiment a surface opposite the first surface 904, 924 that will not contact the dental appliance has a lower average surface roughness than the first surface. For example, the surface opposite the first surface may be a smooth surface (e.g., a polished surface). The smooth surface may reduce at least one of absorbance or reflectance of the object to light.

In one embodiment, the object 900, 920 comprises plastic impregnated with a photo-thermal compound. For such embodiments, the dental appliance may be transparent or clear, and laser welding may be performed by directing coherent light through the dental appliance onto the first surface that is mated with the dental appliance. The photo-thermal compound at the first surface absorbs the coherent light having a target wavelength and generates heat that melts the object and the dental appliance at the interface of the first surface and the second surface. By impregnating the photo-thermal compound into the object, a manufacturing step of coating the object with the photo-thermal compound may be eliminated. However, more photo-thermal compound may be used in such an embodiment, which can increase cost.

In one embodiment, the object 900, 920 incudes one or more through holes. The through holes may prevent air entrapment during placement of the object into a cavity of a feature of a dental appliance. Air entrapment may cause air bubbles that prevent successful bonding at a location of the air bubbles. In one embodiment, a vacuum is applied via the holes after the object has been placed into a cavity of a dental appliance to remove any air. In one embodiment, the object 900, 920 is shaped to prevent air entrapment (e.g., with a curved convex slope where the object will contact the feature of the dental appliance.

In one embodiment, the object is manufactured using injection molding. An injection mold may be formed, and a first surface of the injection mold may be roughened to cause the first surface of the object to have a target surface roughness. In one embodiment, the surface of the injection mold is roughened via chemical etching. In one embodiment, the first surface of the object is coated with the bonding agent (e.g., photo-thermal compound) after the injection molding. In one embodiment, the bonding agent is sprayed onto the first surface of the object (e.g., using ultrasonic spraying). An approximately uniform layer of the bonding agent may be achieved, facilitated by the first surface having a target wettability due to its surface roughness.

In one embodiment, an ultrasonic spray system is utilized to apply a uniform coating of the adhesive agent. In one embodiment, the ultrasonic spray system includes an ultrasonic spray nozzle that breaks a liquid to be sprayed (e.g., using an ultrasonic frequency of about 120 kHz) into small droplets that evenly coat the first surface of the object. The spray may be shaped with airflow from an airflow system. The nozzle may be mounted to a gantry system, and the liquid delivery to the nozzle may be controlled by a syringe pump to control a flow rate. An amount of a photo-thermal compound that is deposited onto the object may be controlled through varying gantry speed. Once deposited, the liquid may dry, leaving behind the coating of the photo thermal compound. One example of process parameters that achieve a uniform coating density of about 20 to about 60 nL/mm² (e.g., about 40 nL/mm²) include:
1. Line width (controlled by gantry height): about 15 mm;
2. Flow rate: about 0.250 mL/min;
3. Translation speed: about 27.8 mm/s; and
4. 4 passes with sufficient time between passes to allow coating to dry.

Figure 9C:
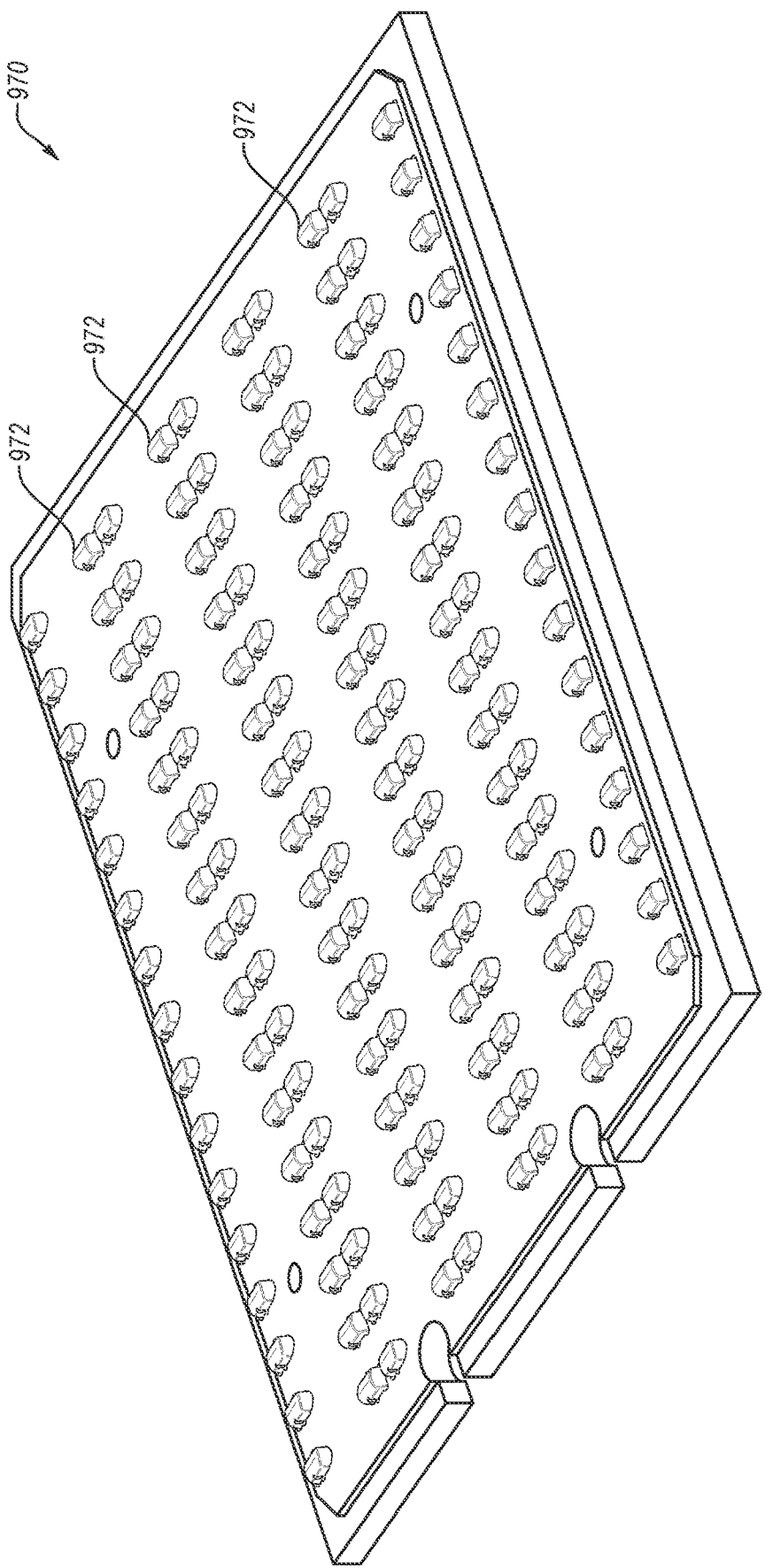
FIG. 9C illustrates a tray for objects to be inserted into features of dental appliances, in accordance with embodiments of the present disclosure.
Figure 9D:
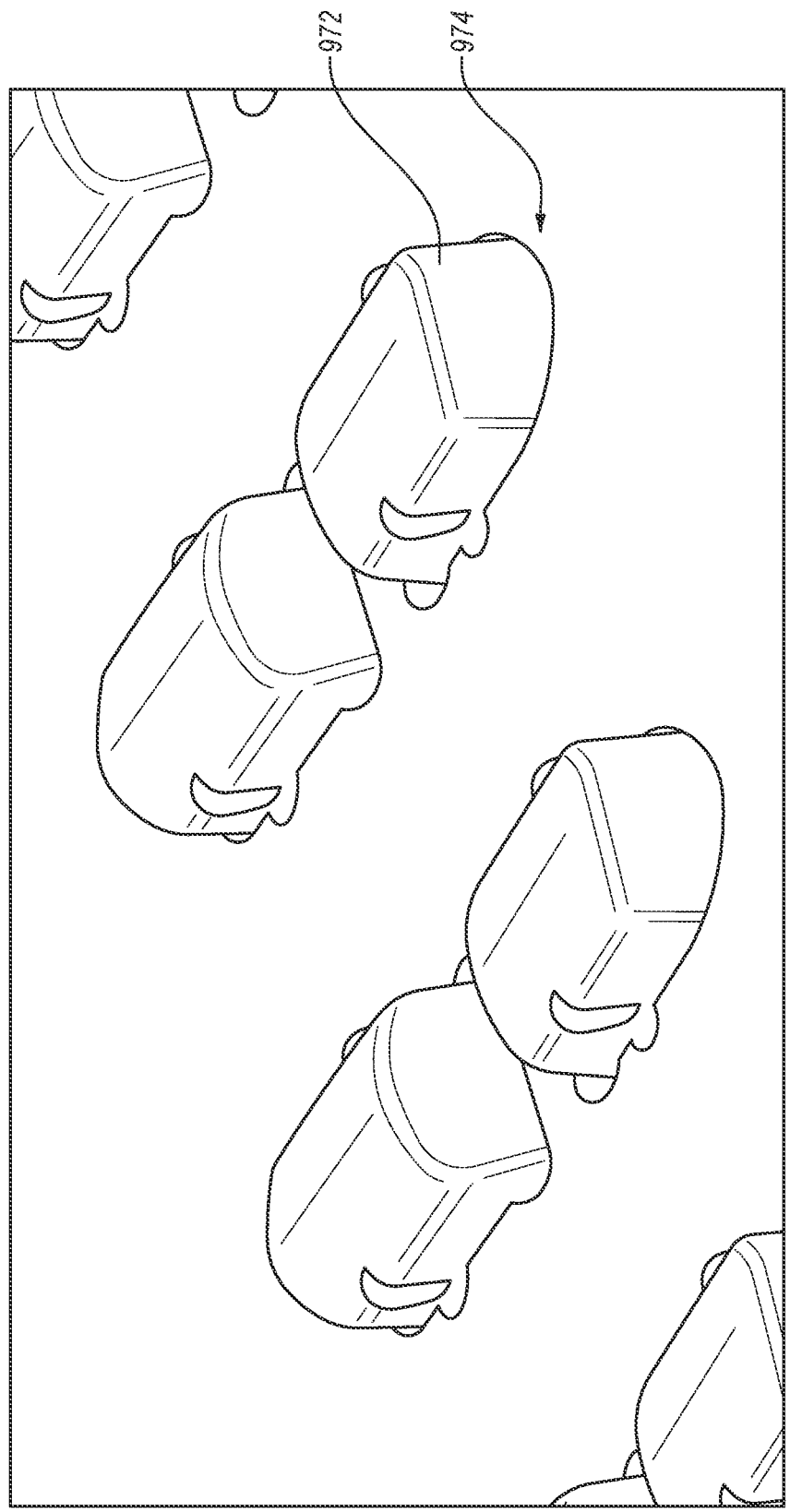
FIG. 9D illustrates a magnified view of a region of the tray of FIG. 9C.

In one embodiment, objects are placed into a tray, and are coated while in the tray. Alternatively, objects may be placed into the tray after being coated. Alternatively, objects may be placed onto a conveyor (e.g., a conveyor belt) before or after spraying the adhesive coating on the objects. In one embodiment, the objects are placed on a tape and reel. FIG. 9C illustrates a tray 970 for objects 972 to be inserted into features of dental appliances, in accordance with embodiments of the present disclosure. FIG. 9D illustrates a magnified view of a region of the tray of FIG. 9C, showing objects 972 in object-shaped cavities in the tray 970. In one embodiment, tray 970 is double-sided to facilitate stacking for storage, shipping and/or loading of blocks into a welding station. In one embodiment, for loading of blocks into the welding station, a stack is inverted so that blocks have bottom (uncoated) faces (that will not contact a dental appliance surface) accessible for pick-and-place by a robotic arm.

Returning to FIG. 1, after inspection of the dental appliance, the holder and dental appliance may be moved to a robot station. In one embodiment, the holder and held dental appliance are automatically moved to the robot station, such as via a conveyor (e.g., a conveyor belt). Alternatively, the robot station may be collocated with the inspection station, and the holder is not moved after inspection at the inspection station. At block 130 a robot arm picks up an object having the determined object type. At block 135 the robot arm then places the object against the feature of the dental appliance. This may include inserting the object into or onto the feature of the dental appliance, for example. The holder may hold the feature of the dental appliance at a reference position and with a known orientation. The robot arm may therefore automatically place the object at a correct position and orientation onto the feature of the dental appliance without the use of any cameras to determine how to position the robot arm relative to the dental appliance.

Figure 10:
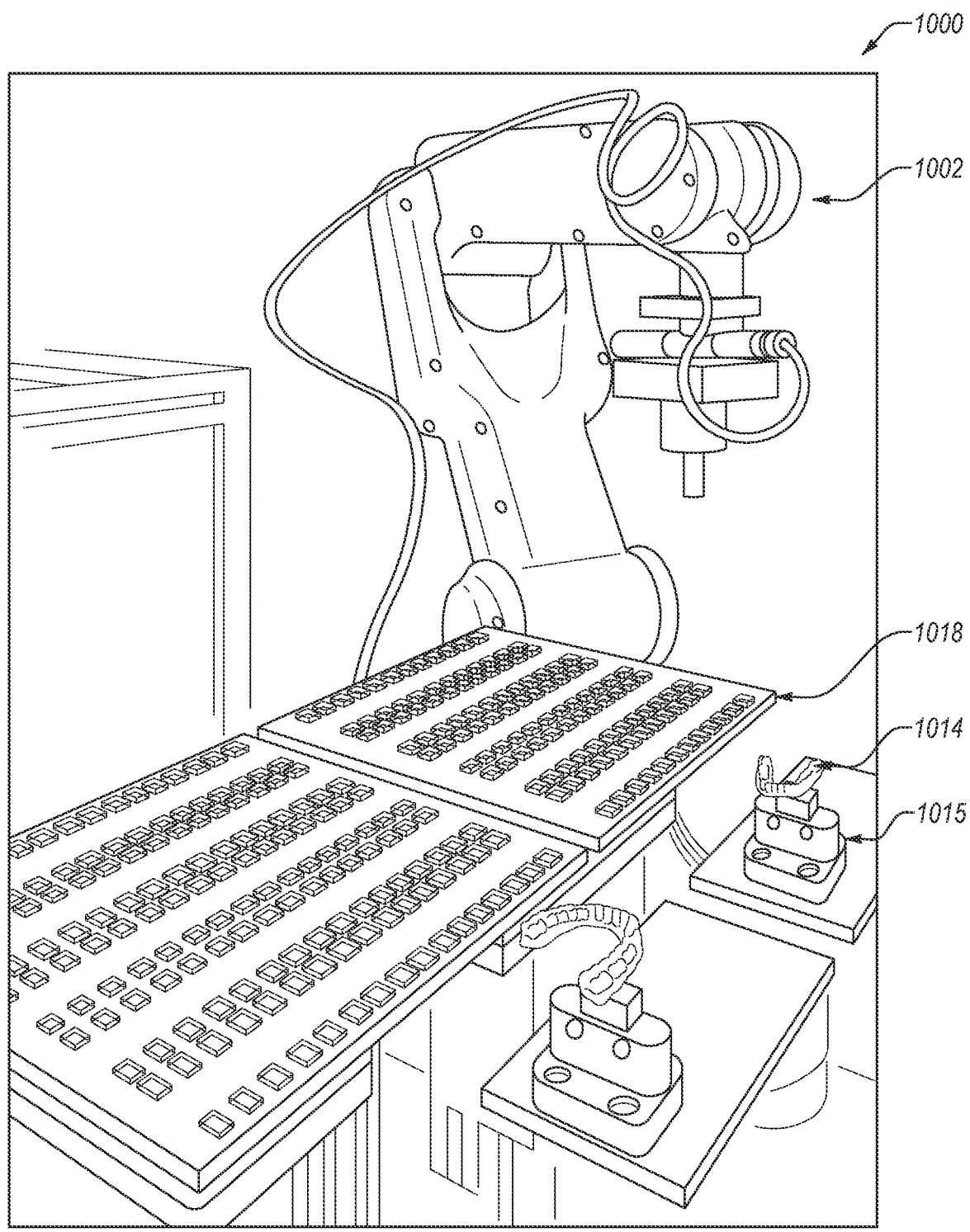
FIG. 10 illustrates a perspective view of a robot arm that picks objects up and inserts them into aligners, in accordance with embodiments of the present disclosure.

FIG. 10 illustrates a perspective view of a robot station 1000 including a robot arm 1002 that picks objects up (e.g., from tray 1018) and inserts them into aligners 1014 held in holders 1015, in accordance with embodiments of the present disclosure. The robot arm may be a multi-axis robot arm capable of movement in x, y and/or z axes and/or rotations about up to three axes in embodiments. The robot arm may be programmed to pick an object from a first known location and to place the object at a feature of a dental appliance at a second known location in embodiments.

The robot arm may be programmed to apply a set force at particular positions (e.g., z coordinates) based on a type of object being placed. For example, during placement of the object onto or into the feature of the dental appliance, over a set robot arm z (vertical) position range an increased force may be required to insert the object into a cavity of the feature. In one embodiment, the cavity has a narrower opening along at least one dimension at a top of the cavity than at a bottom of the cavity. Accordingly, placing the object against the feature and into the cavity causes walls of the cavity to flex outward. An increased force may need to be applied by the robot arm to cause the walls of the cavity to flex outward over a particular z position range. Once the object is fully seated against the feature (e.g., pressed completely into a cavity of the feature), the walls of the cavity may return to an unflexed position.

Figures 11A, 11B, 11C:
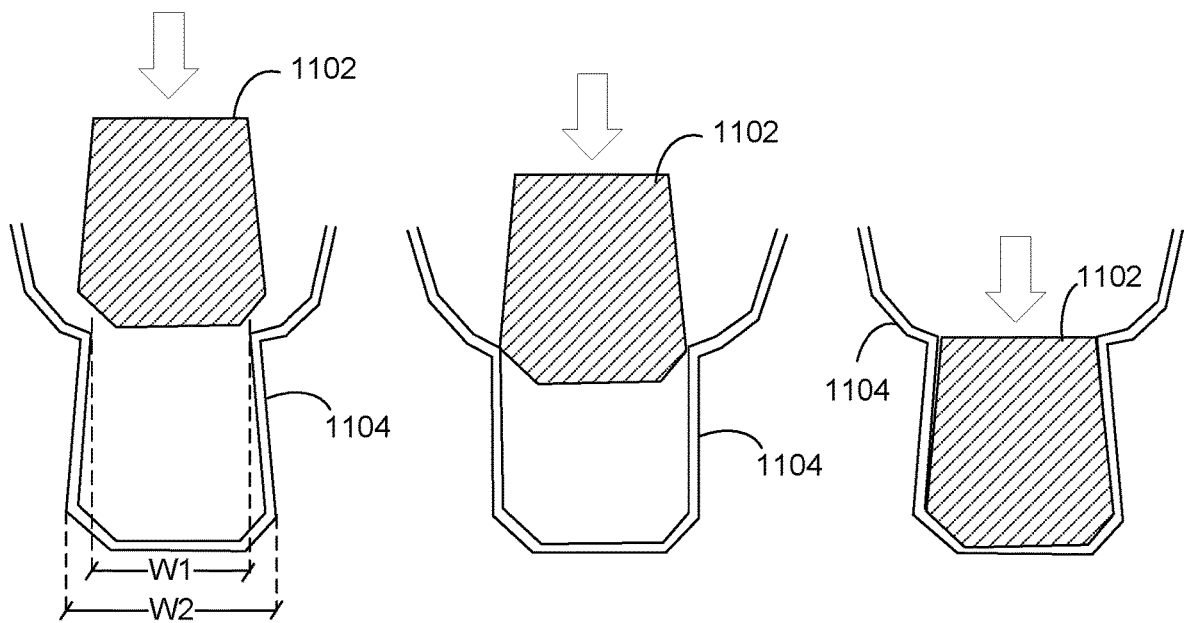
FIGS. 11A-C illustrate insertion of an object into a cavity of an aligner, in accordance with embodiments of the present disclosure.

FIGS. 11A-C illustrate insertion of an object into a cavity of an aligner having a narrower opening at a top of the cavity than at a bottom of the cavity, in accordance with embodiments of the present disclosure. Accordingly, the cavity has a negative incline in at least one dimension. As shown, a width W2 of a bottom of the cavity is wider than a width W1 of a top of the cavity of the dental appliance 1104. Accordingly, when a bottom of the object 1102 is pressed against the top of the cavity, the walls of the cavity flex outward, as shown in FIG. 11B. Then once the object is fully seated into the cavity, the walls of the cavity return to their non-flexed positions, as shown in FIG. 11C.

Figure 11D:
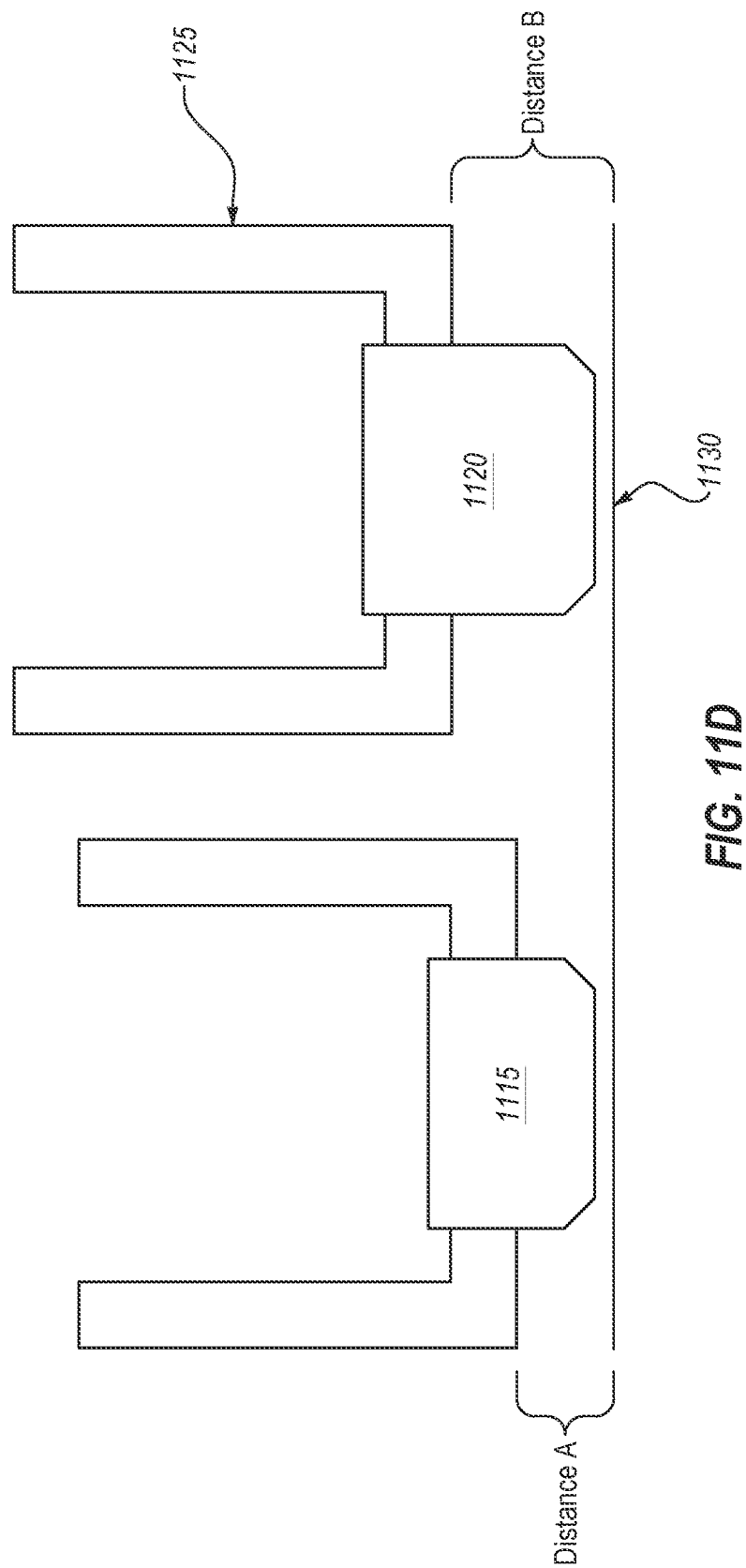
FIG. 11D illustrates force tolerances for insertion of blocks into cavities of aligners, in accordance with embodiments of the present disclosure.

FIG. 11D illustrates force tolerances for insertion of objects (e.g., blocks) into cavities of aligners, in accordance with embodiments of the present disclosure. As shown, robot arm grippers 1125 may hold a first object 1115 having a first object type or a second object 1120 having a second object type. The first object 1115 may have a first height that is less than a second height of the second object 1120. During placement of an object against a feature of a dental appliance (e.g., into a cavity of a dental appliance), an amount of force applied to place the object against the feature of the dental appliance may be measured using a force sensor and a position (e.g., z coordinate) of a robot arm may be measured. Processing logic may then compare that force to one or more force threshold (e.g., an upper force threshold and a lower force threshold). In one embodiment, an upper force threshold of 80 Newtons and a lower force threshold of 60 Newtons is used. However, other upper and/or lower force thresholds may also be used (e.g., 20 Newtons, 40 Newtons, 100 Newtons, 120 Newtons, 200 Newtons, etc.). The force thresholds may be associated with particular z coordinate ranges, which may be based on a type of object being inserted. Processing logic may determine whether the object has been correctly placed against the feature (e.g., into the cavity) of the dental appliance based on whether the amount of force is between the upper force threshold and the lower force threshold over a z coordinate range. If the force is between the upper and lower force thresholds, then a successful placement may be determined. If the force is above the upper force threshold or below the lower force threshold, then an unsuccessful placement may be determined.

As set forth above, for certain z coordinates of the robot arm an increased force is expected. Depending on a type of object being inserted, the z coordinates at which an increased force is expected may vary. For example, the robot arm may have a first height (e.g., a first z coordinate value) when a bottom of object 1115 contacts a top of a cavity 1130 based on distance A between the robot gripper 1125 and the bottom of the first object 1115. The robot arm may have a second height (e.g., a second z coordinate value) when a bottom of object 1120 contacts a top of a cavity 1130 based on distance B between the robot gripper 1125 and the bottom of the second object 1120. Accordingly, if first object 1115 is being inserted into a cavity, then an increased force may be expected starting at the first z coordinate value, and if the second object 1120 is being inserted into a cavity, then an increased force may be expected starting at the second z coordinate value. If an increased force (e.g., of between 60 Newtons and 80 Newtons) is not detected starting at the first z coordinate for placement of the first object 1115 or is not detected starting at the second coordinate for placement of the second object 1120, then an unsuccessful object placement may be determined.

Additionally, additional force thresholds may be applied for positions outside of the z coordinate range. For example, an upper force threshold of 50 or 60 Newtons may be used outside of the z coordinate range. If an increased force (e.g., that is above is above the additional force threshold) is detected early (e.g., at a higher z coordinate value than the first z coordinate value for the first object or the second z coordinate value for the second object), then an unsuccessful object placement may be determined. Such forces that are detected to be outside of force limits may indicate that an incorrect object was picked up, or example.

Figure 11E:
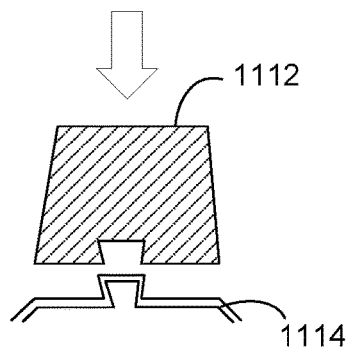
FIGS. 11E-G illustrate insertion of an object onto a feature of an aligner, in accordance with embodiments of the present disclosure.
Figure 11F:
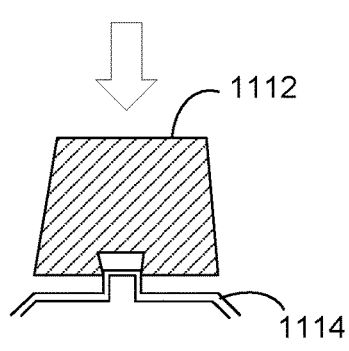
Figure 11G:
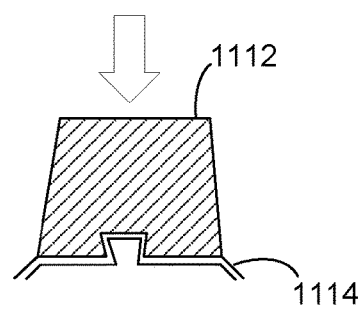

FIGS. 11E-G illustrate insertion of an object 1112 onto a feature of a dental appliance 1114, in accordance with embodiments of the present disclosure. In FIGS. 11A-C, the feature of the dental appliance included a cavity into which the object 1102 was inserted. However, the feature of dental appliance 1114 does not include a cavity. Instead, the feature includes a surface onto which the object 1112 is placed. In one embodiment, as shown, the feature includes an engagement structure that helps to secure the object 1112 to the feature of the dental appliance 1114. In the illustrated example, the engagement structure is a dovetail pin, and the object 1112 includes a dovetail channel that is shaped to receive the dovetail pin. Other types of engagement structures may also be used. As with FIGS. 11A-C, a force may be applied to flex the walls of the engagement structure (e.g., flex them inward). Once the object 1112 is fully seated against the dental appliance 1114, then the walls of the engagement structure may return to the unflexed position. In other embodiments, other types of engagement structures may be used, such as other types of pins, flats, grooves, curves and/or indentations.

Returning to FIG. 1, after the object has been placed into the dental appliance, the holder with the attached dental appliance may be moved to an inspection station. In one embodiment, the holder and held dental appliance are automatically moved to the inspection station, such as via a conveyor (e.g., a conveyor belt). In one embodiment, the dental appliance is moved to a same inspection station that was used to inspect the dental appliance in the holder prior to insertion of the object. Alternatively, the inspection station may be different from the inspection station used to inspect the dental appliance in the holder. In one embodiment, the robot station corresponds to the inspection station. In one embodiment, the inspection station corresponds to inspection station 800 of FIG. 8 or inspection station 300 of FIG. 3.

At block 138, inspection of the object inserted into the feature of the dental appliance may be performed. Inspection may include generating one or more images of the object placed against the feature (e.g., into a cavity of the feature) and processing the one or more images to determine whether the object was correctly placed against the feature of the dental appliance. In one embodiment, the image(s) is input into a trained machine learning model that outputs an indication as to whether the object was successfully placed against the feature. For example, processing logic may identify if the object is protruding from a cavity, or if the cavity walls remain flexed, or if the object is a wrong object type for the dental appliance, or if the object was inserted into the cavity with an incorrect orientation, and so on. For example, different sides of the feature may have different shapes, and a correct object may have sides with similar matching shapes to those of the feature. If an incorrect object is placed against the feature, or if a correct object is placed against the feature with an incorrect orientation, then the object may not properly mate with the feature. An image may show the incorrect mating of the object with the feature. If the object was incorrectly placed, then the object may be removed and/or replaced, and inspection may be repeated. Alternatively, the operation of block 138 may be skipped, and the dental appliance and holder may be moved directly to a bonding station (e.g., a welding station). The machine learning model or a different machine learning model may also output an indication as to whether the dental appliance was damaged as a result of placing the object against the dental appliance. Damage detection may be performed using the same process or a similar process to that performed at block 118.

At block 140, the holder and held dental appliance are moved to the bonding station (e.g., welding station). In one embodiment, the holder and held dental appliance are automatically moved to the bonding station, such as via a conveyor (e.g., a conveyor belt). At the bonding station, a force may be applied to press the object against the feature of the dental appliance, and a bonding operation may be performed to bond the object to the dental appliance. In one embodiment, a laser welding process is performed to weld the object to the dental appliance.

Figure 12A:
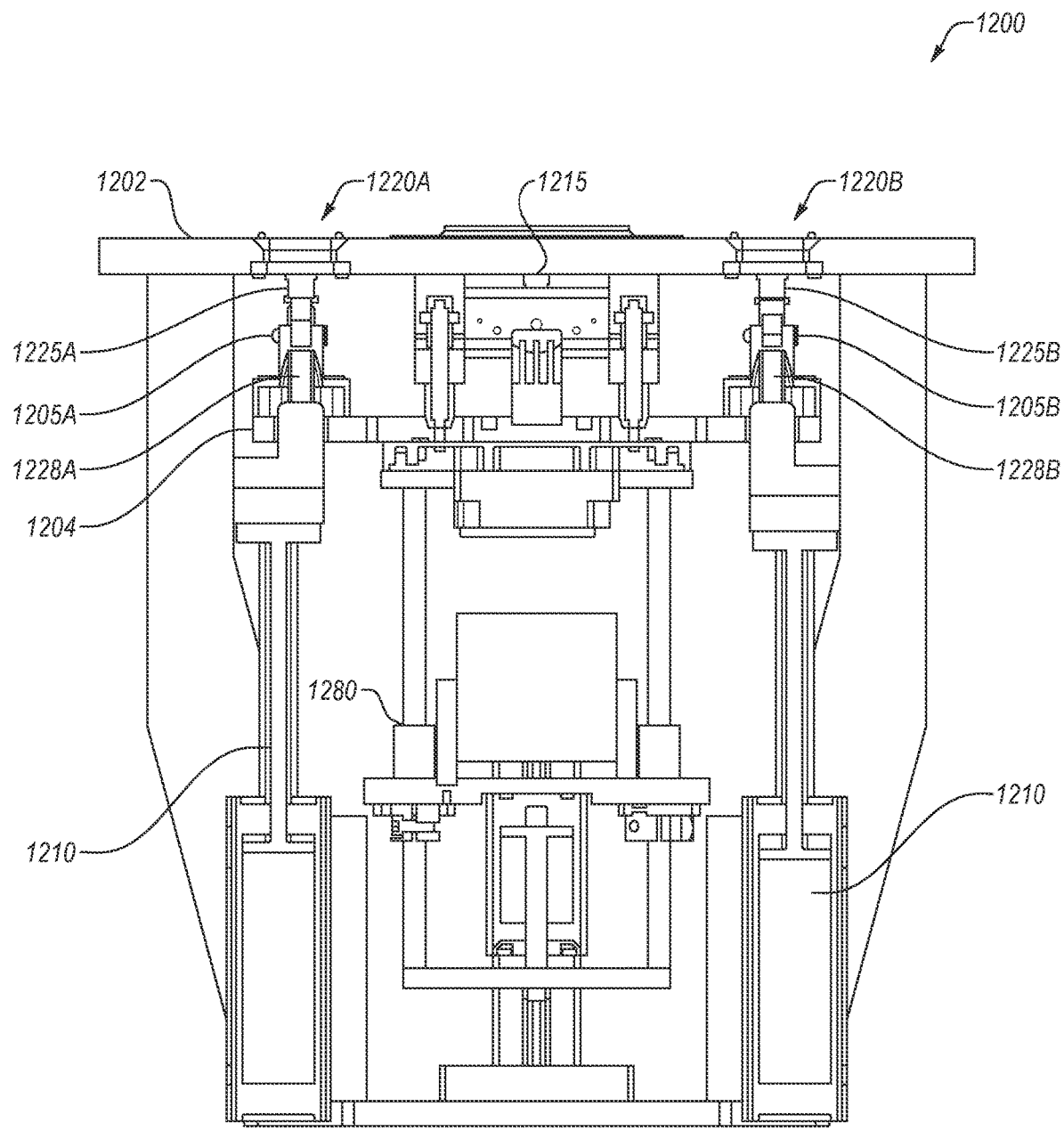
FIG. 12A illustrates a cross sectional side view of a bonding station for bonding a block to an aligner into which it has been inserted, in accordance with embodiments of the present disclosure.
Figure 12B:
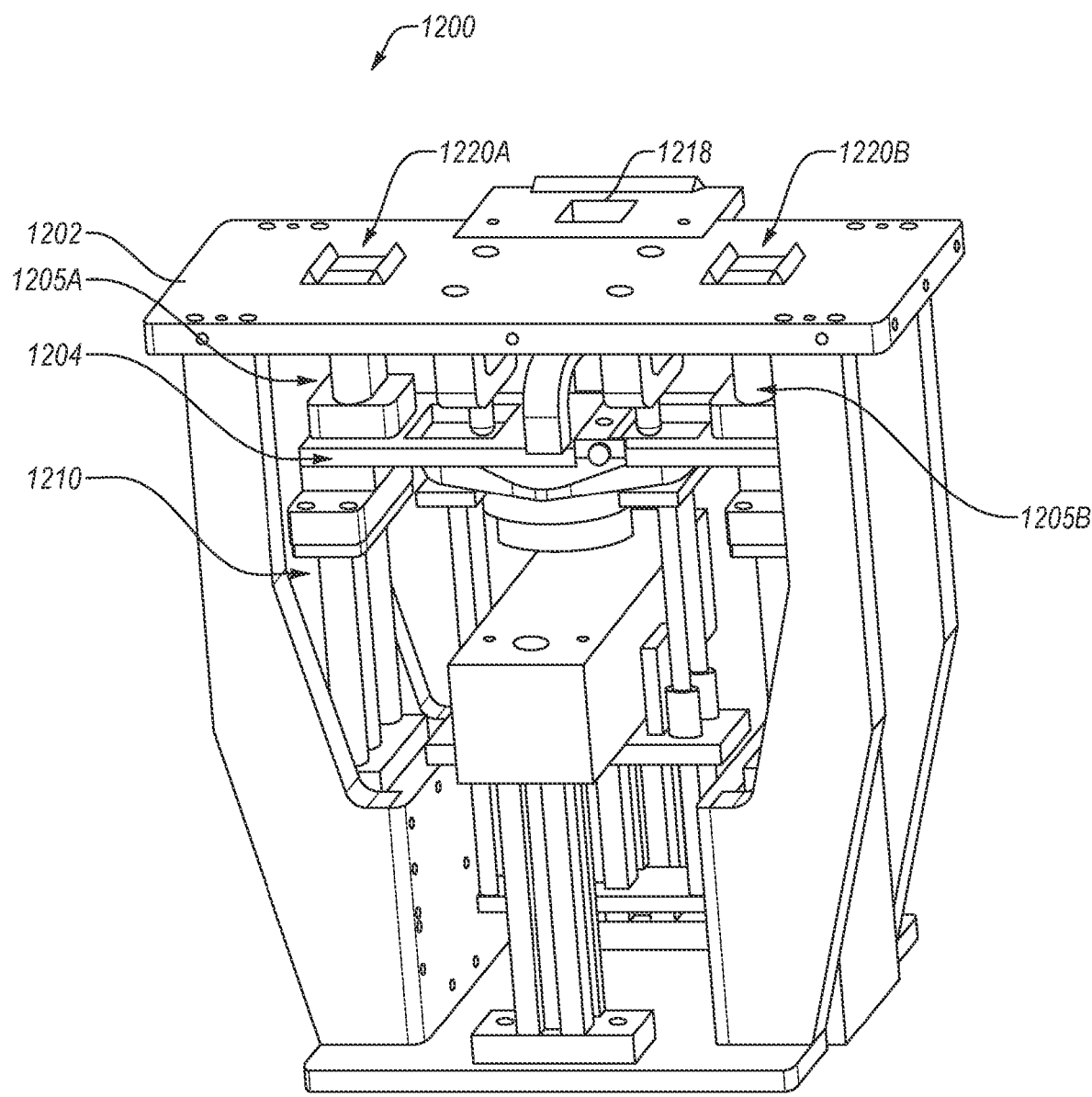
FIG. 12B illustrates a perspective view of the bonding station of FIG. 12A, in accordance with embodiments of the present disclosure.
Figure 12C:
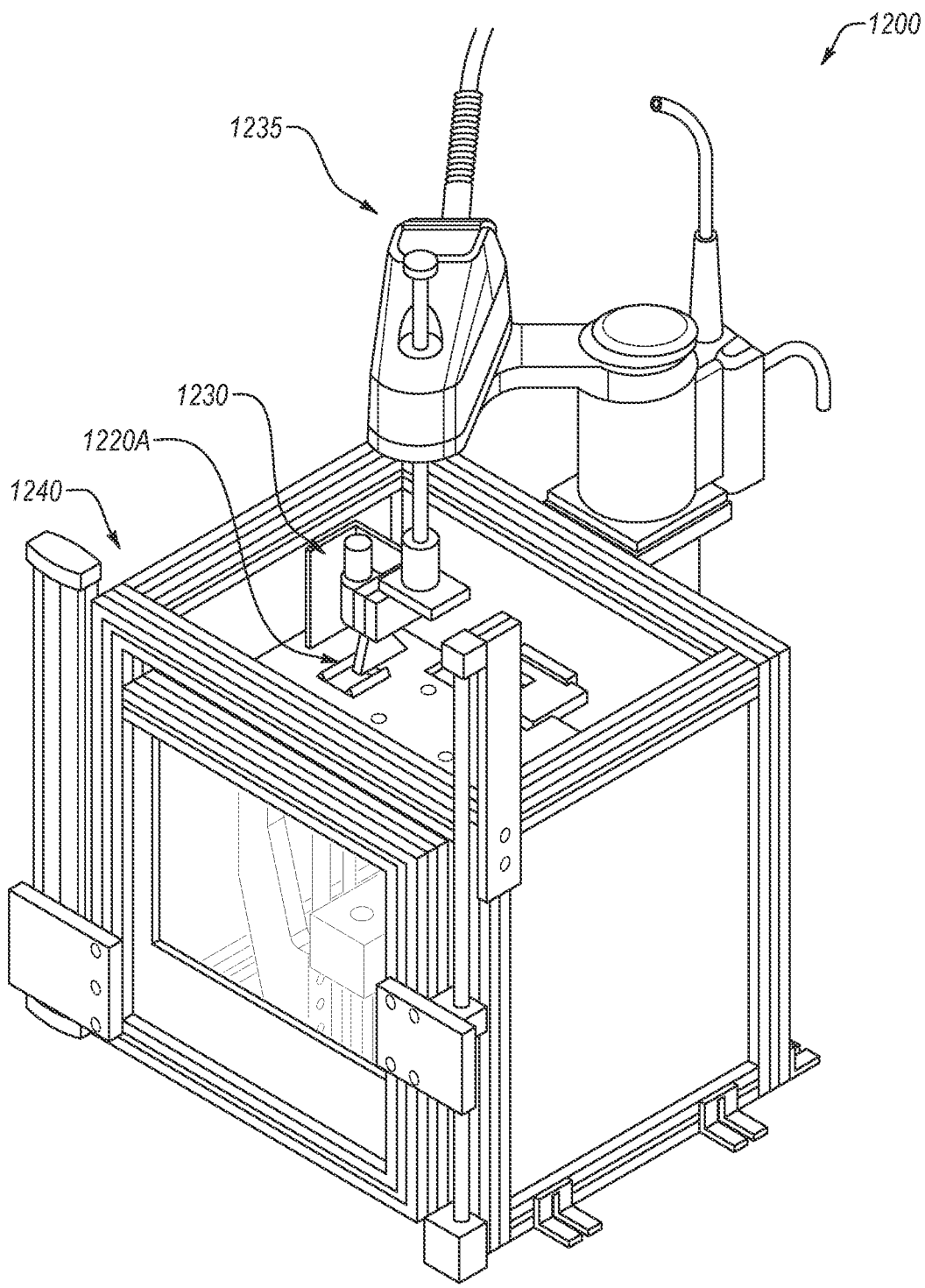
FIG. 12C illustrates a perspective view of the bonding station of FIGS. 12A-B, with the addition of a housing and a robot arm comprising a light source, in accordance with embodiments of the present disclosure.
Figure 12D:
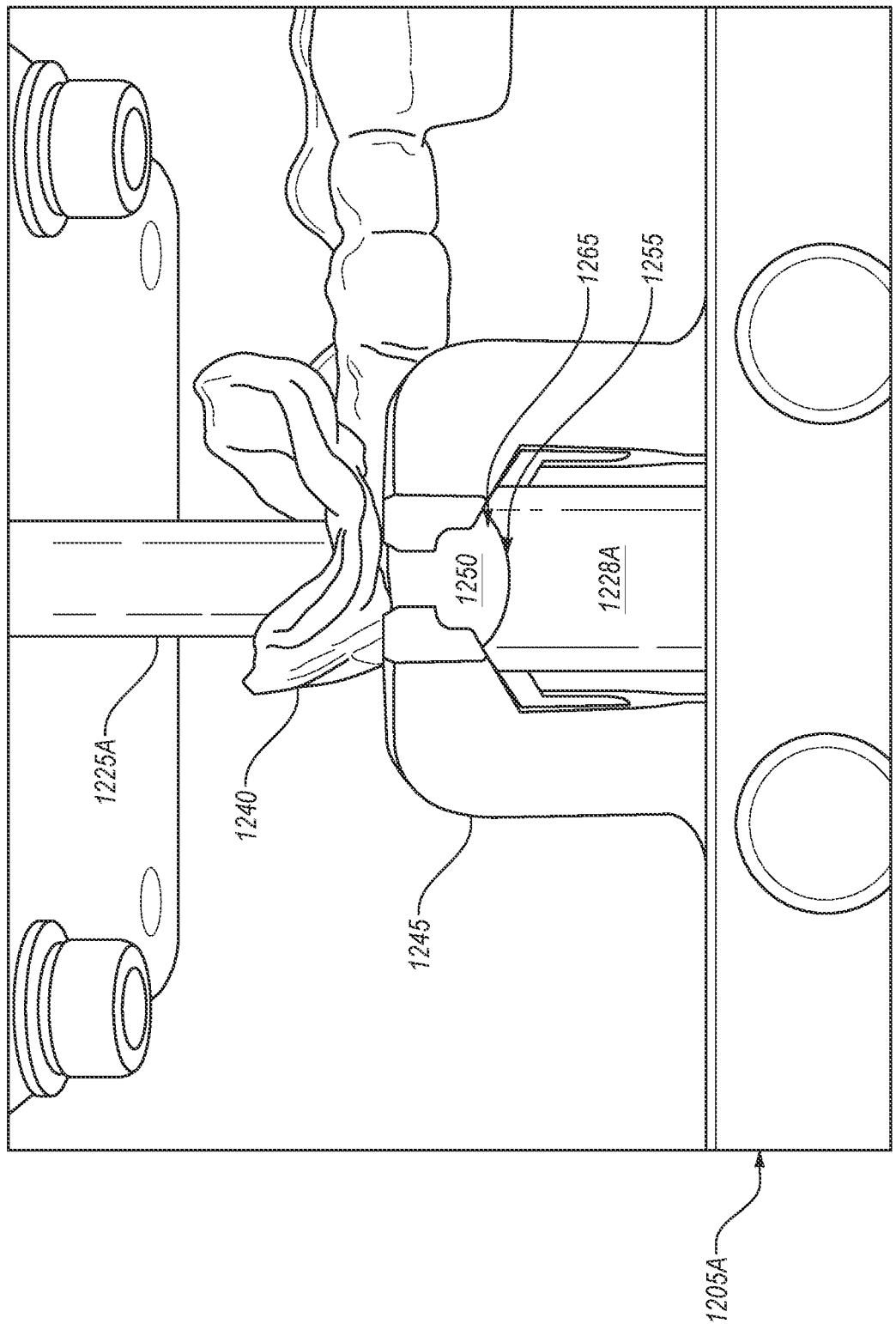
FIG. 12D illustrates a cross sectional side view of a portion of the bonding station of FIGS. 12A-C during a bonding process, in accordance with embodiments of the present disclosure.
Figure 12E:
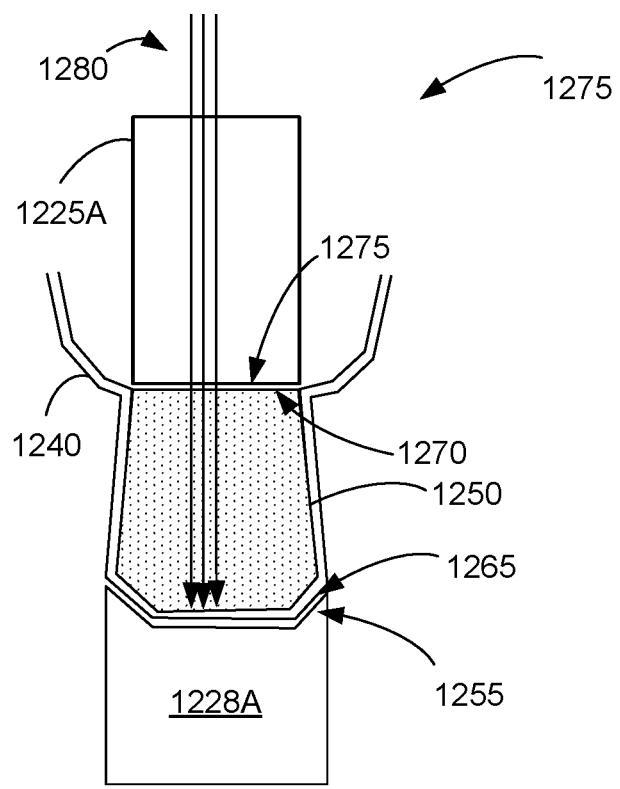
FIG. 12E illustrates a cross sectional side view of a portion of the bonding station of FIGS. 12A-C during a bonding process, in accordance with embodiments of the present disclosure.

FIG. 12A illustrates a cross sectional side view of a bonding station 1200 for bonding an object to an aligner into or onto which it has been inserted, in accordance with embodiments of the present disclosure. FIG. 12B illustrates a perspective view of the bonding station 1200 of FIG. 12A, in accordance with embodiments of the present disclosure. FIG. 12C illustrates a perspective view of the bonding station 1200 of FIGS. 12A-B, with the addition of a housing 1240 and a robot arm 1235 comprising a light source 1230, in accordance with embodiments of the present disclosure. FIG. 12D illustrates a cross sectional side view of a portion of the bonding station 1200 of FIGS. 12A-C during a bonding process, in accordance with embodiments of the present disclosure. FIG. 12E illustrates a cross sectional side view of a portion of the bonding station 1200 of FIGS. 12A-C during a bonding process, in accordance with embodiments of the present disclosure.

Referring to FIGS. 12A-E, bonding station 1200 includes a moveable platform 1204 that supports one or more holder 1205A, 1205B. Each holder 1205A, 1205B may hold a dental appliance 1240 (e.g., via a feature of the dental appliance). The moveable platform 1204 may be connected to a pusher 1280, which may move the moveable platform 1204 with the attached holders 1205A, 1205B up and down. The pusher 1280 may be, for example, a pneumatic plunger, a linear actuator, and so on. The bonding station 1200 may further include an upper platform 1202 that supports one or more upper clamping fixture 1225A, 1225B. Upper clamping fixtures 1225A, 1225B may be clear or transparent to light output by a light source used to perform bonding (e.g., to laser light) in embodiments. In one embodiment, upper clamping fixtures 1225A, 1225B are plastic, acrylic, glass, quartz, or another transparent material. The upper platform 1202 and attached upper clamping fixtures 1225A, 1225B may have a fixed position in embodiments. Accordingly, the pusher 1280 may push the platform 1204 and attached holders 1205A, 1205B against the upper clamping fixtures 1225A, 1225B.

Bonding station 1200 may additionally include pusher 1210 attached to one or more lower clamping fixtures 1228A, 1228B. In one embodiment, the lower clamping fixtures 1228A, 1228B are composed of aluminum or an aluminum alloy. In one embodiment, the lower clamping fixtures 1228A, 1228B are acrylic, plastic, stainless steel, cast iron, or another material. The pusher 1280 may be, for example, a pneumatic plunger, a linear actuator, and so on. Pusher 1280 may push the lower clamping fixtures 1228A, 1228B against a surface of the dental appliance 1240 or object 1250. In one embodiment, pusher 1280 pushes the lower clamping fixtures 1228A, 1228B against the surface of the dental appliance 1240 with a force of about 10-30 psi (e.g., about 20 psi). Upper clamping fixtures 1225A, 1225B may apply pressure on the object 1250 disposed on or inserted into the feature and clamping fixtures 1228A, 1228B may apply an opposite pressure a side of the dental appliance 1240 onto which the object 1250 is disposed or into which the object 1250 is inserted. Accordingly, the pusher 1210 may press the object 1250 against the dental appliance 1240.

As shown, holders 1205A, 1205B may include a channel on their interior into which the lower clamping fixtures 1228A, 1228B may be inserted by pusher 1210. In one embodiment, the upper clamping fixtures 1225A, 1225B are composed of a transparent material through which light may be received and directed toward the object 1250 and feature of the dental appliance 1250. Accordingly, upper clamping fixtures 1225A, 1225B may act as a light guide to direct light (e.g., coherent light output by a laser).

A surface 1255 of lower clamping fixture 1228A that contacts a surface 1265 of the dental appliance 1240 may be a contoured surface having a first shape that matches a shape of an occlusal surface of the dental appliance 1240 at the feature that the lower clamping fixture 1228A contacts. Similarly, a surface 1275 of upper clamping fixture 1225A that contacts a surface 1270 of the object 1250 may be a contoured surface having a second shape that matches a shape of the object that the upper clamping fixture 1225A contacts. Accordingly, an even force distribution may be applied to the entire contact region of the object and the dental appliance that will be bonded. In one embodiment, lower clamping fixture 1228A, 1228B includes a flexible surface on a surface that contacts the dental appliance. The flexible surface may be, for example, a layer of a flexible material such as a plastic, silicon or rubber. The flexible surface may improve a force distribution across the surface of the contact region between the dental appliance and the object that is to be bonded.

While the force (e.g., a vertical force) is applied to press the object against the dental appliance, a robot arm 1235 may move a light source 1230 (e.g., a laser that emits coherent light having a particular wavelength, such as IR light) to direct coherent light 1280 through a cavity 1220A, 1220B in the upper platform 1202, through the upper clamping fixture 1225A, 1225B, through the object 1250, and onto the interface of the object and the dental appliance 1240. In one embodiment, the laser is a line laser that produces a laser line. The robot arm 1235 may move the laser line along one axis to ensure that all of the surface of the object to be bonded receives the laser light. In one embodiment, the laser is a spot laser that generates a spot. The robot arm 1235 may move the laser spot along two axes (e.g., x axis and y axis) to ensure that all of the surface of the object to be bonded receives the laser light. The laser light may cause a photo thermal compound that coats a surface of the object to heat up (e.g., the photo thermal compound reacts with the light to heat up), melting the object 1250 and the dental appliance 1240 at an interface of the object 1250 and the dental appliance 1240.

Weld quality can be important for ensuring patient safety. Too little welding can lead to a break of the bond between the dental appliance and the object, and a possible choking hazard. However, too much welding can melt the dental appliance. Factors that affect weld quality include a coating density of the photo thermal compound, laser power, clamping pressure, and gantry speed (speed of movement of the laser beam). In one embodiment, coating density is about 20 to about 60 nL/mm$^2$ (e.g., about 40 nL/mm$^2$), laser power is about 20 to about 40 W (e.g., about 31 W), clamping pressure is about 10 psi to about 30 psi, and gantry speed is about 5 mm/s to about 9 mm/s (e.g., about 7 mm/s).

In one embodiment, upper platform 1202 includes a cutout 1218 that provides access to a power meter 1215. Periodically (e.g., before bonding an object to a dental appliance), robot arm 1235 may direct laser 1230 towards the power meter 1215. The power meter 1215 may measure a power of the coherent light output by the laser 1230 to ensure that the coherent light is being delivered with a target power. If a detected amount of power deviates from the target power, then a power of the laser may be adjusted until the delivered power is equal to the target power. This power setting may then be used during laser welding.

In one embodiment, the object 1250 does not include a photo thermal compound coating, and instead a laser light is used that has a sufficient wavelength (e.g., of about 2 microns) to heat the interface of the object and the dental appliance without use of the photo thermal compound.

In one embodiment, side walls of the object and the feature of the dental appliance are not bonded. In such an embodiment, the side walls of the object may not be coated with a bonding agent, and may be smooth (e.g., have a relatively low average surface roughness. In other embodiments, side walls of the object are also bonded to the dental appliance. In addition to the upward force applied by the pusher 2110, a sideward force may be applied such as by the jaws of holder 1245. An angle of light may be adjusted (e.g., by rotating robot arm 1235) so that the light contacts an interface of the sidewalls of the object and the dental appliance (e.g., the sidewalls of the object and the sidewalls of the cavity into which the object has been inserted). Thus, a laser weld may be achieved both on a bottom surface (or top surface) of the object and on the sidewalls of the object.

In one embodiment, the laser light is directed through the dental appliance 1240 and onto the interface of the dental appliance 1240 and the object 1250 rather than through the object 1250. In such an embodiment, the laser may be positioned beneath the dental appliance (rather than above the dental appliance as shown). Alternatively, the dental appliance may be positioned such that the occlusal surface of the dental appliance faces upwards rather than the mating surface of the dental appliance shaped to fit over teeth of a patient (as illustrated).

In embodiments where the bonding agent is something other than a photo thermal compound, a different bonding station may be used. For example, if a UV-cured adhesive is used, then a UV light may be attached to the robot arm rather than a laser. If a thermally cured adhesive is used, then the bonding station may include one or more heating elements to heat the dental appliance and object.

In one embodiment, a vacuum clamp is used to press the object against the dental appliance. In such an embodiment, the object may include one or more holes and a vacuum may be applied to the interface of the object and the dental appliance via the one or more holes. The vacuum may apply a force the pulls the dental appliance against the object.

Returning to FIG. 1, after the object has been bonded to the dental appliance, the holder with the attached dental appliance may be moved to an inspection station in order for a bond inspection to be performed. In one embodiment, the holder and held dental appliance are automatically moved to the inspection station, such as via a conveyor (e.g., a conveyor belt). In one embodiment, the dental appliance is moved to a same inspection station that was used to inspect the dental appliance in the holder prior to insertion of the object and/or the inspection station that was used to inspect the dental appliance after the object was inserted into the dental appliance. Alternatively, the inspection station may be different from the previously used inspection stations. In one embodiment, the bonding station includes an integrated inspection station, and a bond inspection may be performed at the bonding station. In one embodiment, the inspection station corresponds to inspection station 800 of FIG. 8 or inspection station 300 of FIG. 3.

At block 145, a bond inspection is performed at the inspection station. Performing the bond inspection may include capturing one or more images of the object attached to the dental appliance and performing image processing on the one or more images and/or inputting the one or more images into a trained machine learning model. The trained machine learning model and/or image processing algorithm(s) may output an indication of a bond quality. In an example, the dental appliance and/or the object may include build lines that remain present if an adequate bond has not been formed at a region. However, the build lines may melt and reflow when a proper bond is achieved, eliminating the build lines. Thus, processing logic may identify which regions retain build lines, and determine that those regions that retain build lines have not been successfully bonded. In one embodiment, a grid pattern is overlaid over the image of the object in the dental appliance. The grid pattern can be used to divide the interface between the object and the dental appliance into successful bond regions and unsuccessful bond regions. A size of the successful and/or unsuccessful bond regions may be determined and/or a ratio of the size of the successful bond region to the size of the unsuccessful bond region may be determined. The determined size(s) and/or ratio may be compared to one or more threshold to determine whether or not the bond meets one or more bond quality criteria. For example, if the successful bond region size is below a threshold, if the unsuccessful bond region size is above a threshold and/or if the ratio of the successful bond region size to the unsuccessful bond region size is below a threshold, then a determination may be made that the bond does not meet the quality criteria and is a partial weld. However, if the successful bond region size is at or above a threshold, if the unsuccessful bond region size is at or below a threshold and/or if the ratio of the successful bond region size to the unsuccessful bond region size is at or above a threshold, then a determination may be made that the bond meets the quality criteria. In one embodiment, the bond is considered a partial bond if less than 100% of the surface region has been bonded. In one embodiment, the bond is considered a partial bond if less than 80% of the surface region has been bonded. In one embodiment, the bond is considered a partial bond if less than 50% of the surface region has been bonded.

If the bond does not meet the quality criteria, then the bonding process may be repeated. After the bonding process has been repeated, another bond inspection may be performed at the inspection station. If after a threshold number of bond attempts the bond continues to not satisfy bond quality criteria, then the dental appliance may be scrapped. If the bond is successful, then the dental appliance is safe to use and can be packaged and shipped to a doctor or patient.

Figure 13A:
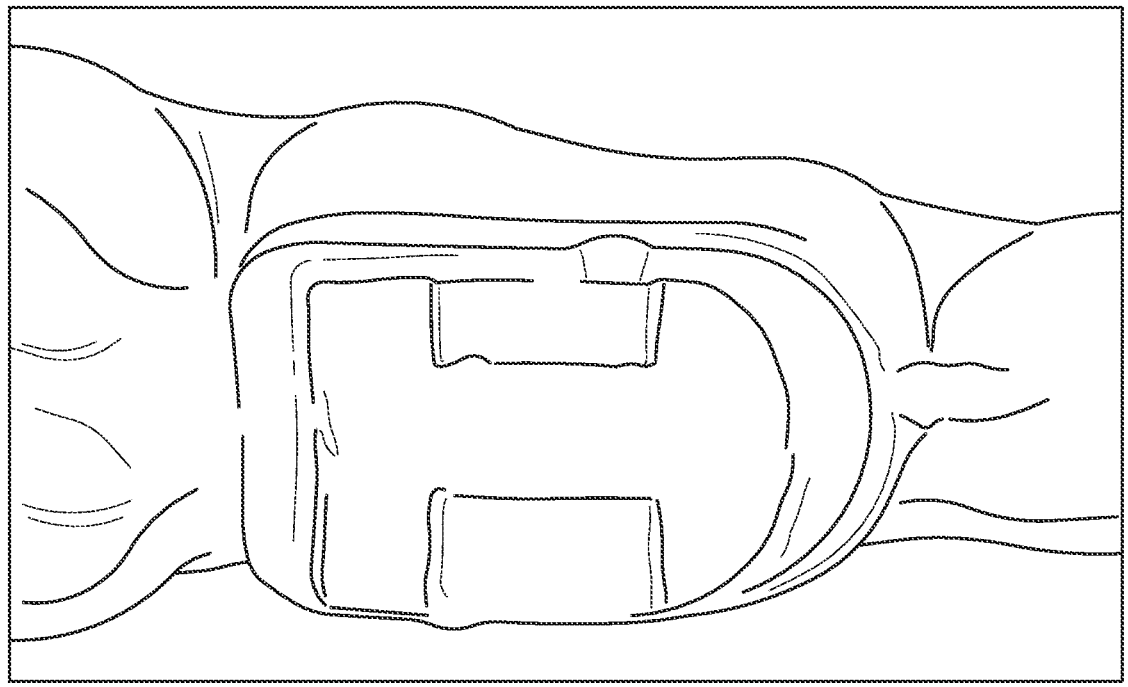
FIG. 13A is an image of an object fully bonded to an aligner, in accordance with embodiments of the present disclosure.

FIG. 13A is an image of an object fully bonded to an aligner, in accordance with embodiments of the present disclosure. As shown, there are no build lines visible on the bottom surface of the object that interfaces with the dental appliance.

Figure 13B:
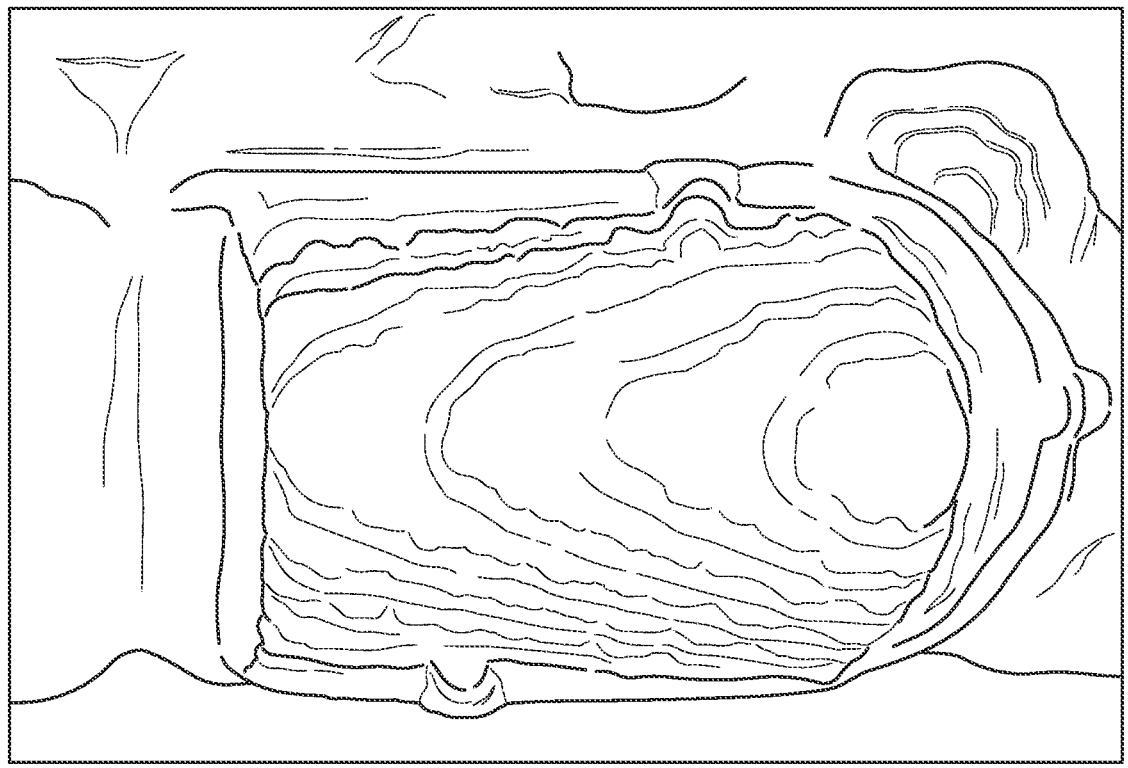
FIG. 13B is an image of an object partially bonded to an aligner, in accordance with embodiments of the present disclosure.

FIG. 13B is an image of an object that has not been bonded to an aligner, in accordance with embodiments of the present disclosure. As shown, there are multiple build lines visible on the bottom surface of the object that interfaces with the dental appliance.

Figure 14:
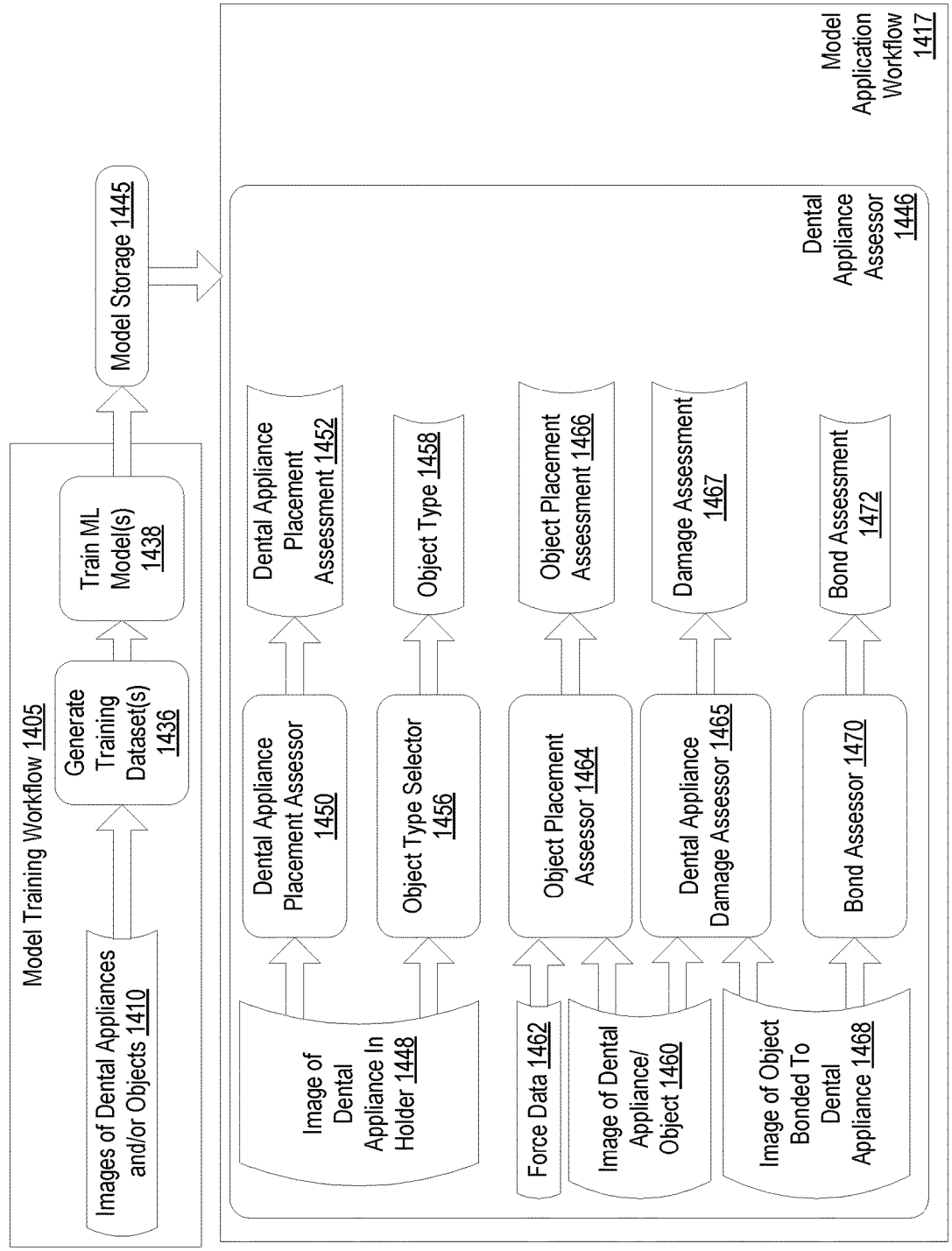
FIG. 14 illustrates a model training workflow and a model application workflow for quality assessment of a dental appliance, in accordance with embodiments of the present disclosure.

FIG. 14 illustrates a model training workflow 1405 and a model application workflow 1417 for quality control of a dental appliance, in accordance with an embodiment of the present disclosure. In embodiments, the model training workflow 1405 may be performed at a server, and the trained models are provided to a processing device at an inspection station. In one embodiment, the one or more trained models together form a dental appliance placement assessor 1446. The model training workflow 1405 and the model application workflow 1417 may be performed by processing logic executed by a processor of a computing device (e.g., computing device 1700 of FIG. 17). One or more of these workflows 1405, 1417 may be implemented, for example, by one or more machine learning models implemented in a quality control system.

The model training workflow 1405 is to train one or more machine learning models (e.g., deep learning models) to perform one or more classifying, segmenting, detection, recognition, etc. tasks for images (e.g., 2D images and/or 3D images) of dental appliances and/or objects disposed against dental appliances. The model application workflow 1417 is to apply the one or more trained machine learning models to perform the classifying, segmenting, detection, recognition, estimation, prediction, etc. tasks for dental appliances and/or objects based on images of the dental appliances and/or objects. One or more of the machine learning models may receive and process 3D data (e.g., 3D point clouds, 3D surfaces, portions of 3D models, etc.). One or more of the machine learning models may receive and process 2D data (e.g., 2D color images).

Many different machine learning outputs are described herein. Particular numbers and arrangements of machine learning models are described and shown. However, it should be understood that the number and type of machine learning models that are used and the arrangement of such machine learning models can be modified to achieve the same or similar end results. Accordingly, the arrangements of machine learning models that are described and shown are merely examples and should not be construed as limiting. Additionally, one or more of the machine learning models may be replaced by traditional image processing algorithms in some embodiments.

In embodiments, one or more machine learning models are trained to perform one or more of the below tasks. Each task may be performed by a separate machine learning model. Alternatively, a single machine learning model may perform each of the tasks or a subset of the tasks. Additionally, or alternatively, different machine learning models may be trained to perform different combinations of the tasks. In an example, one or a few machine learning models may be trained, where the trained ML model is a single shared neural network that has multiple shared layers and multiple higher level distinct output layers, where each of the output layers outputs a different prediction, classification, identification, etc. The tasks that the one or more trained machine learning models may be trained to perform are as follows:

I) Dental appliance placement assessment—this can include classifying images of dental appliances inserted into a holder as correctly positioned in the holder or incorrectly positioned in the holder. If the dental appliance is incorrectly positioned in the holder, the machine learning model can output an indication of why the placement is incorrect.

II) Dental Appliance type determination and/or object type selection—this can include classifying images of dental appliances inserted into a holder as belonging to a dental appliance type from a plurality of different dental appliance types (e.g., from two dental appliance types or four dental appliance types). This can further include determining an object type to be used for a dental appliance.

III) Object placement assessment—this can include classifying images of dental appliances with objects inserted into or onto features thereof as showing a correct object placement or an incorrect object placement. If an incorrect object placement is detected, this can include identifying why the object placement is incorrect.

IV) Dental appliance damage assessment—this can include classifying images of dental appliances as showing a damaged dental appliance or an undamaged dental appliance. In embodiments, dental appliance damage assessment is performed after an object is placed against a feature of a dental appliance.

V) Bond assessment—this can include classifying images of a bond between a dental appliance and an object as a full bond or a partial bond. In embodiments, bond assessment includes identifying regions of an interface between a surface of an object and a surface of a feature of a dental appliance as having a successful bond and identifying regions between the surface of the object and the surface of the feature of the dental appliance as having an unsuccessful bond. In embodiments, a pixel-level or patch-level analysis of the dental appliance and object are performed to identify the interface between the dental appliance and the object to be assessed and to determine for pixels representing the interface whether the pixel is associated with a successful bond or an unsuccessful bond.

One type of machine learning model that may be used to perform some or all of the above asks is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize a scanning role. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

For the model training workflow 1405, a training dataset containing hundreds, thousands, tens of thousands, hundreds of thousands or more images should be used to form a training dataset. In embodiments, images of manufactured dental appliances to treat up to millions of cases of patient dentition may be available for forming a training dataset. Each image may include various labels of one or more types of useful information. Each image may include, for example, data indicating whether the dental appliance was correctly placed in a holder in the image, a dental appliance type and/or object type for a dental appliance in the image, an indication as to whether an object was correctly placed against a feature of the dental appliance in the image, an indication as to whether or not the dental appliance in the image was damaged, pixel-level or patch-level segmentation of the image into various classes (e.g., bond region, not bond region, successful bond, unsuccessful bond, etc.), and so forth. This data may be processed to generate one or multiple training datasets 1436 for training of one or more machine learning models. The machine learning models may be trained, for example, to automate the one or more processes associated with quality analysis of a manufactured dental appliance that includes an object bonded to a surface of the dental appliance. Such trained machine learning models can be added to a dental appliance assessor 1446, and can be applied to automatically assess a quality of a dental appliance during various stages of manufacturing.

In one embodiment, generating one or more training datasets 1436 includes gathering many images of dental appliances and/or objects with labels 1410. The labels that are used may depend on what a particular machine learning model will be trained to do. For example, to train a machine learning model to perform classification of regions as having a successful or unsuccessful bond, a training dataset 1436 may include pixel-level labels or patch-level labels of bond quality.

Processing logic may gather a training dataset 1436 comprising 2D or 3D images 1410 having one or more associated labels (e.g., pixel-level, patch-level labels, image level labels, etc.). One or more images, and optionally associated labels, in the training dataset 1436 may be resized in embodiments. For example, a machine learning model may be usable for images having certain pixel size ranges, and one or more image may be resized if they fall outside of those pixel size ranges. The images may be resized, for example, using methods such as nearest-neighbor interpolation or box sampling. The training dataset may additionally or alternatively be augmented. Training of large-scale neural networks generally uses tens of thousands of images, which are not easy to acquire in many real-world applications. Data augmentation can be used to artificially increase the effective sample size. Common techniques include random rotation, shifts, shear, flips and so on to existing images to increase the sample size.

To effectuate training, processing logic inputs the training dataset(s) 1436 into one or more untrained machine learning models. Prior to inputting a first input into a machine learning model, the machine learning model may be initialized. Processing logic trains the untrained machine learning model(s) based on the training dataset(s) to generate one or more trained machine learning models that perform various operations as set forth above.

Training may be performed by inputting one or more of the images into the machine learning model one at a time. Each input may include data from an image in a training data item from the training dataset. Additionally, or alternatively, additional layers may include three layers for color values (e.g., a separate layer for each color channel, such as an R layer, a G layer and a B layer), a layer for pixel information from an image generated under specific lighting conditions, and so on. In some embodiments, data from multiple images is input into the machine learning model together, where the multiple images may all be of the same dental appliance.

The machine learning model processes the input to generate an output. An artificial neural network includes an input layer that consists of values in a data point (e.g., intensity values and/or height values of pixels in a height map). The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class, prediction and/or output that the machine learning model can produce. For example, for an artificial neural network being trained to perform bond quality classification, there may be a first class (successful bond), a second class (unsuccessful), a third class (not a bond region), and/or one or more additional classes. Moreover, the class, prediction, etc. may be determined for each pixel in the image, may be determined for an entire image, or may be determined for each region or group of pixels (e.g., patch) of the image. For pixel level segmentation, for each pixel in the image, the final layer applies a probability that the pixel of the image belongs to the first class, a probability that the pixel belongs to the second class, a probability that the pixel belongs to the third class, and/or one or more additional probabilities that the pixel belongs to other classes.

Accordingly, the output may include one or more prediction and/or one or more a probability map. For example, an output probability map may comprise, for each pixel in an input image, a first probability that the pixel belongs to a first class, a second probability that the pixel belongs to a second class, and so on. For example, the probability map may include probabilities of pixels belonging to classes representing a successful bond, an unsuccessful bond, or not a bond region.

Processing logic may then compare the generated probability map and/or other output to the known probability map and/or label that was included in the training data item. Processing logic determines an error (i.e., a classification error) based on the differences between the output probability map and/or label(s) and the provided probability map and/or label(s). Processing logic adjusts weights of one or more nodes in the machine learning model based on the error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

Once the model parameters have been optimized, model validation may be performed to determine whether the model has improved and to determine a current accuracy of the deep learning model. After one or more rounds of training, processing logic may determine whether a stopping criterion has been met. A stopping criterion may be a target level of accuracy, a target number of processed images from the training dataset, a target amount of change to parameters over one or more previous data points, a combination thereof and/or other criteria. In one embodiment, the stopping criteria is met when at least a minimum number of data points have been processed and at least a threshold accuracy is achieved. The threshold accuracy may be, for example, 70%, 80% or 90% accuracy. In one embodiment, the stopping criteria is met if accuracy of the machine learning model has stopped improving. If the stopping criterion has not been met, further training is performed. If the stopping criterion has been met, training may be complete. Once the machine learning model is trained, a reserved portion of the training dataset may be used to test the model.

As an example, in one embodiment, a machine learning model (e.g., bond assessor 1470) is trained to segment images by classifying regions of those images into one or more classes associated with bond quality. A similar process may be performed to train machine learning models to perform other tasks such as those set forth above. A set of many (e.g., thousands to millions) images of objects bonded to dental appliances with labeled classes may be collected. In an example, each point in the images may include a label having a first value for a first label representing a successful bond, a second value for a second label representing an unsuccessful bond, and a third value for a third label representing a region that is not a bond region. One of the three values may be 1, and the other two values may be 0, for example. Points that have a first class may have a value of (1,0,0) (100% probability of a successful bond and 0% probability of an unsuccessful bond or a region that is not a bond region), points that have a second class may have a value of (0,1,0), and points that have a third class may have a value of (0,0,1) for example. If a machine learning model is being trained to perform image-level classification/prediction as opposed to pixel-level classification/segmentation, then a single value or label may be associated with a generated image as opposed to a map having pixel-level values.

A training dataset may be gathered, where each data item in the training dataset may include an image and an associated probability map (which may be a 2D map if associated with an image or a 3D map if associated with a 3D surface) and/or other label. Additional data may also be included in the training data items. Multiple sources of information can be incorporated into model inputs and used jointly for prediction. Multiple dental classes can be predicted concurrently from a single model or using multiple models. Multiple problems can be solved simultaneously: dental appliance placement assessment, dental appliance type determination, object type determination, object placement assessment, dental appliance damage assessment, bond assessment, etc.

In one embodiment, model application workflow 1417 includes a dental appliance assessor 1446 that includes one or more trained machine learning models that function as a dental appliance placement assessor 1450, an object type selector 1456, an object placement assessor 1464, a dental appliance damage assessor 1465, and/or a bond assessor 1470. These logics may be implemented as separate machine learning models or as a single combined machine learning model in embodiments. For example, dental appliance placement assessor 1450 and object type selector 1456 may share one or more layers of a deep neural network. However, each of these logics may include distinct higher level layers of the deep neural network that are trained to generate different types of outputs. In some embodiments, the dental appliance placement assessor 1450, object type selector 1456, object placement assessor 1464, dental appliance damage assessor 1465 and/or bond assessor 1470 are separate logics that are not part of dental appliance assessor 1446.

For model application workflow 1417, according to one embodiment, a camera of an inspection station generates one or more image (e.g., a 2D image or 3D image) of a dental appliance during a stage of manufacturing. Each of the dental appliance placement assessor 1450, object type selector 1456, object placement assessor 1464, dental appliance damage assessor 1465 and/or bond assessor 1470 may be configured to process images at a particular stage in a manufacturing process. In some embodiments, multiple dental appliance damage assessors 1465 are used, where each may be associated with a different stage in a manufacturing process.

After a dental appliance has been placed into a holder, an image of the dental appliance in the holder 1448 may be generated. The image may be input into the dental appliance placement assessor 1450, which may use a trained machine learning model and/or traditional image processing techniques to determine whether the dental appliance was correctly placed in the holder. This may include determining whether the dental appliance was fully seated in the holder, whether an orientation of the dental appliance in the holder is correct, whether the dental appliance was placed into a correct type of holder, and so on. The dental appliance assessor 1450 (e.g., a trained machine learning model of dental appliance placement assessor 1450) outputs a dental appliance placement assessment 1452. The dental appliance placement assessment 1452 may be a simple indication that the dental appliance was correctly placed in the holder or incorrectly placed in the holder. Alternatively or additionally, the dental appliance placement assessment 1452 may include an indication as to why the dental appliance was incorrectly placed. For example, the output may include an indication that an incorrect holder was used, that the dental appliance was placed at an incorrect orientation, that an angle of the dental appliance in the holder is incorrect, and so on. This information may be used to reposition the dental appliance correctly in the holder or in a new holder.

After a dental appliance has been placed into a holder, an image of the dental appliance in the holder 1448 may be generated. The image may be input into the object type selector 1456, which may use a trained machine learning model and/or traditional image processing techniques to determine a dental appliance type (e.g., aligner for upper dental arch or aligner for lower dental arch) and/or an associated object type (e.g., occlusal block for use in an aligner for an upper dental arch or an occlusal block for use in an aligner for a lower dental arch). If a dental appliance type is output by the machine learning model, then a corresponding object type 1458 that is associated with the dental appliance type may be determined based on the dental appliance type. Accordingly, object type selector 1456 outputs an object type 1458 for an object to be placed against the dental appliance in embodiments. In one embodiment, the object type selector 1456 classifies between two different types of dental appliances/objects. In one embodiment, the object type selector 1456 classifies between four different types of dental appliances/objects (e.g., tall upper occlusal block, short upper occlusal block, tall lower occlusal block, short lower occlusal block). The object type selector 1456 may output, for each type of dental appliance type/object type, a probability that the dental appliance is associated with that type. The dental appliance type/object type having the highest probability may be identified as the dental appliance type/object type represented in the image.

In one embodiment, the feature of the dental appliance includes a pattern of notches and/or protrusions that identifies the dental appliance type. The object type selector 1456 may process the image 1448 to identify the pattern of notches and/or protrusions, and may decode the pattern of notches and/or protrusions to determine the dental appliance/object type 1458.

After an object has been placed against a feature of a dental appliance (e.g., into a cavity of a feature of a dental appliance), an image of the dental appliance with the attached object 1460 may be generated. Additionally, force data 1462 may have been generated during placement of the object against the feature of the dental appliance. The image and/or force data may be input into the object placement assessor 1464, which may use a trained machine learning model and/or traditional image processing techniques to determine whether the object was correctly placed onto or into the feature of the dental appliance. This may include determining whether the object was fully seated against the feature of the dental appliance, whether any portion of the object protrudes from a cavity of the feature, whether there are gaps between walls of a cavity of the feature and sides of the object, whether walls of the feature are in a flexed position, and so on. The object placement assessor 1464 (e.g., a trained machine learning model of object placement assessor 1464) outputs an object placement assessment 1466. The object placement assessment 1464 may be a simple indication that the object was correctly placed in/on the feature of the dental appliance or incorrectly placed in/on the feature of the dental appliance. Alternatively or additionally, the object placement assessment 1464 may include an indication as to why the object was incorrectly placed. For example, the output may include an indication that an incorrect object was used, that the object was placed at an incorrect orientation, that an angle of the object in/on the feature of the dental appliance is incorrect, and so on. This information may be used to reposition the object or a different object correctly in or on the feature of the dental appliance.

In one embodiment, the image of the dental appliance with the attached object 1460 is input into dental appliance damage assessor 1465. Dental appliance damage assessor 1465 may use a trained machine learning model and/or traditional image processing techniques to determine whether the dental appliance was damaged (e.g., by the act of placing the object into or onto the feature of the dental appliance). This may include determining whether the feature of the dental appliance and/or some other region of the dental appliance is deformed, for example. The dental appliance damage assessor 1465 (e.g., a trained machine learning model of dental appliance damage assessor 1465) outputs an a damage assessment 1467. The damage assessment 1467 may be a simple indication that the dental appliance is damaged. Alternatively or additionally, the damage assessment 1467 may include an indication as to how the dental appliance was damaged and/or a type of class of detected damage. appliance. In one embodiment, a single trained machine learning model performs both object placement assessment and damage assessment. In one embodiment, dental appliance damage assessor 1465 performs one or more operations to assess damage to the dental appliance as set forth in U.S. patent application Ser. No. 16/145,016, filed Sep. 27, 2018, which is incorporated by reference herein.

After a bond has been formed between a dental appliance and an object placed against the dental appliance (e.g., into a cavity of a feature of a dental appliance), an image of the dental appliance with the bonded object 1468 may be generated. The image may be input into the bond assessor 1470, which may use a trained machine learning model and/or traditional image processing techniques to determine a bond quality and/or whether or not a bond satisfies one or more bond quality criteria. In one embodiment, the machine learning model outputs a pixel-level or patch-level map or mask indicating pixels/patches that represent a successful bond or an unsuccessful bond. This information may then be processed to determine a size of a successful bond region, a size of an unsuccessful bond region, a percentage of the total bond region that is successfully bonded, a ratio of the size of the successful bond region to the unsuccessful bond region, and so on. These bond quality metric values may be compared to one or more bond quality criteria (e.g., threshold). If the bond quality metric value or values satisfy the bond quality criteria, then the bond may be identified as full or successful bond. If the bond quality metric value or values fail to satisfy one or more bond quality criteria, then the bond may be identified as an unsuccessful or partial bond. The bond quality information may be output in a bond assessment 1472.

In one embodiment, the image of the object bonded to the dental appliance 1468 is input into dental appliance damage assessor 1465. Dental appliance damage assessor 1465 may use a trained machine learning model and/or traditional image processing techniques to determine whether the dental appliance was damaged (e.g., by the act of bonding the object to the feature of the dental appliance). This may include determining whether the feature of the dental appliance and/or some other region of the dental appliance was melted or deformed, for example. The dental appliance damage assessor 1465 (e.g., a trained machine learning model of dental appliance damage assessor 1465) outputs an a damage assessment 1467. The damage assessment 1467 may be a simple indication that the dental appliance is damaged. Alternatively or additionally, the damage assessment 1467 may include an indication as to how the dental appliance was damaged and/or a type of class of detected damage. appliance. In one embodiment, a single trained machine learning model performs both object placement assessment and damage assessment.

Figure 15:
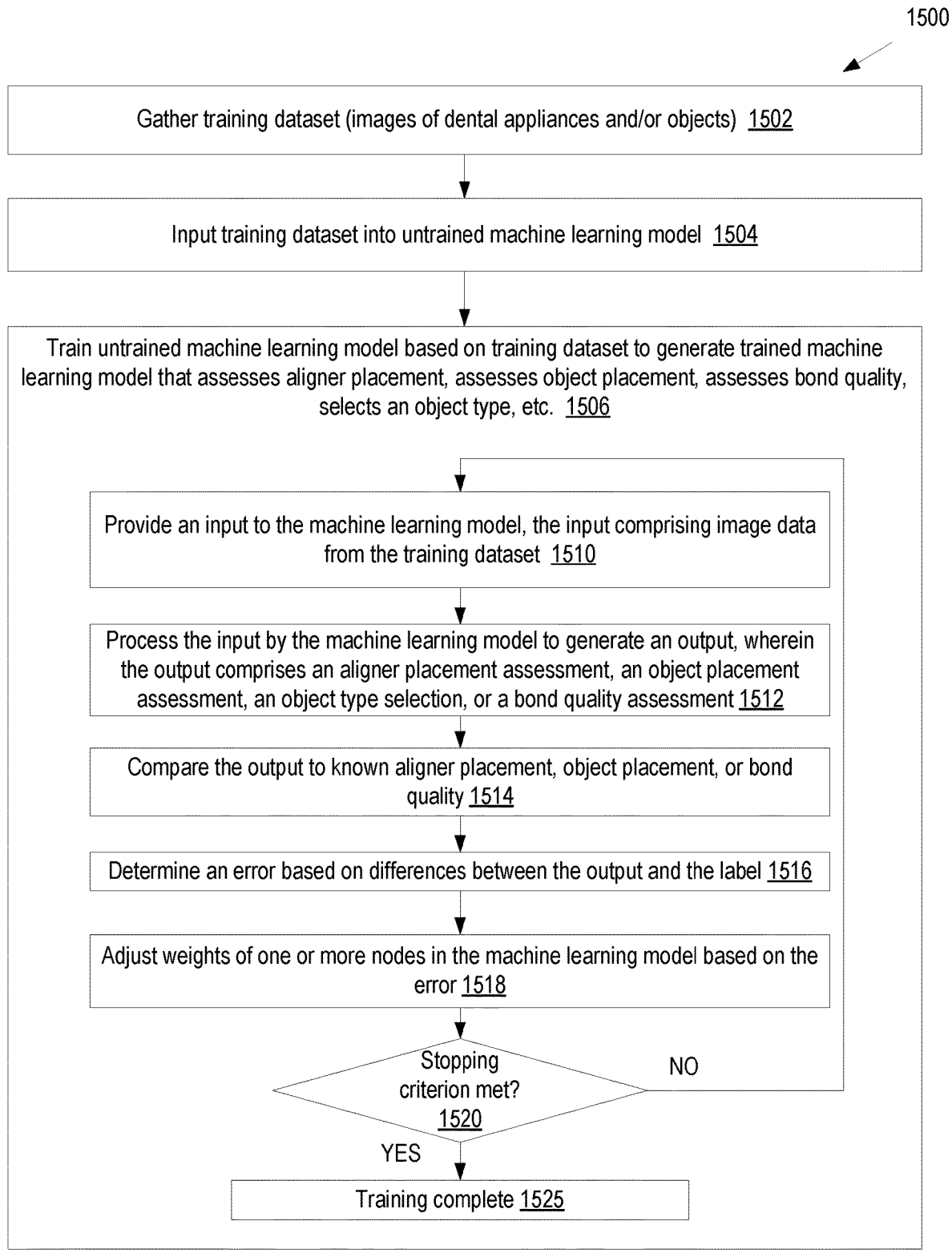
FIG. 15 illustrates a flow diagram for a method of training a machine learning model, in accordance with one embodiment.

FIG. 15 is a flow chart showing a method 1500 for training a machine learning model to perform one or more operations associated with quality control for dental appliance manufacturing, in accordance with embodiments of the present disclosure. Operations method 1500 may be performed by a processing logic that may comprise hardware (e.g., circuitry, dedicated logic, programmable logic, microcode, etc.), software (e.g., instructions run on a processing device to perform hardware simulation), or a combination thereof. The processing logic may execute on one or many processing devices (e.g., of computing device 1700 of FIG. 17).

For simplicity of explanation, the method 1500 is depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

At block 1502 of method 1500, processing logic gathers a training dataset, which may 2D images and/or 3D images of dental appliances and/or objects. Each data item (e.g., image) of the training dataset may include one or more labels. The data items in the training dataset may include image-level labels, pixel-level labels and/or patch-level labels.

At block 1504, data items from the training dataset are input into the untrained machine learning model. At block 1506, the machine learning model is trained based on the training dataset to generate a trained machine learning model that assesses aligner placement, assesses object placement on an aligner, assesses bond quality, selects an object type, assesses damage of an aligner, and so on. The machine learning model may also be trained to output one or more other types of predictions, image-level classifications, pixel-level classifications, patch-level classifications (where a patch is a group of pixels), decisions, and so on.

In one embodiment, at block 1510 an input of a training data item is input into the machine learning model. The input may include data from a 2D image or 3D image. At block 1512, the machine learning model processes the input to generate an output. The output may include an aligner placement assessment, an object placement assessment, an object type selection, a bond quality assessment, an aligner damage assessment, and/or other classification or prediction.

At block 1514, processing logic compares the output to known aligner placement, object placement, bond quality, object type, damage information, etc. At block 1516, processing logic determines an error based on differences between the output and the label associated with the input data item. At block 1518, processing logic adjusts weights of one or more nodes in the machine learning model based on the error.

At block 1520, processing logic determines if a stopping criterion is met. If a stopping criterion has not been met, the method returns to block 1510, and another training data item is input into the machine learning model. If a stopping criterion is met, the method proceeds to block 1525, and training of the machine learning model is complete.

Figure 16A:
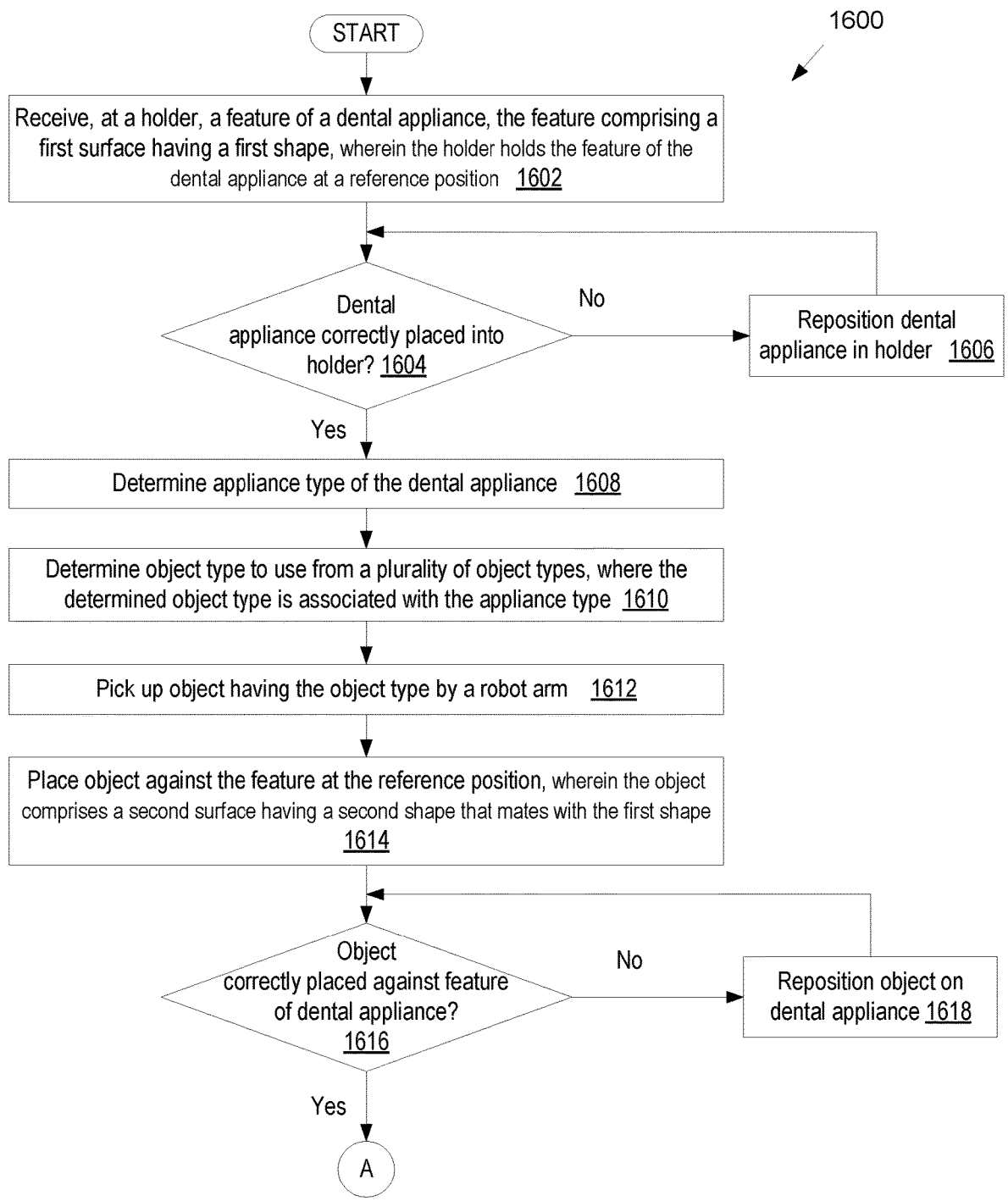
FIGS. 16A-B illustrate a flow diagram for a method of manufacturing and assessing the quality of a dental appliance, in accordance with embodiments of the present disclosure.
Figure 16B:
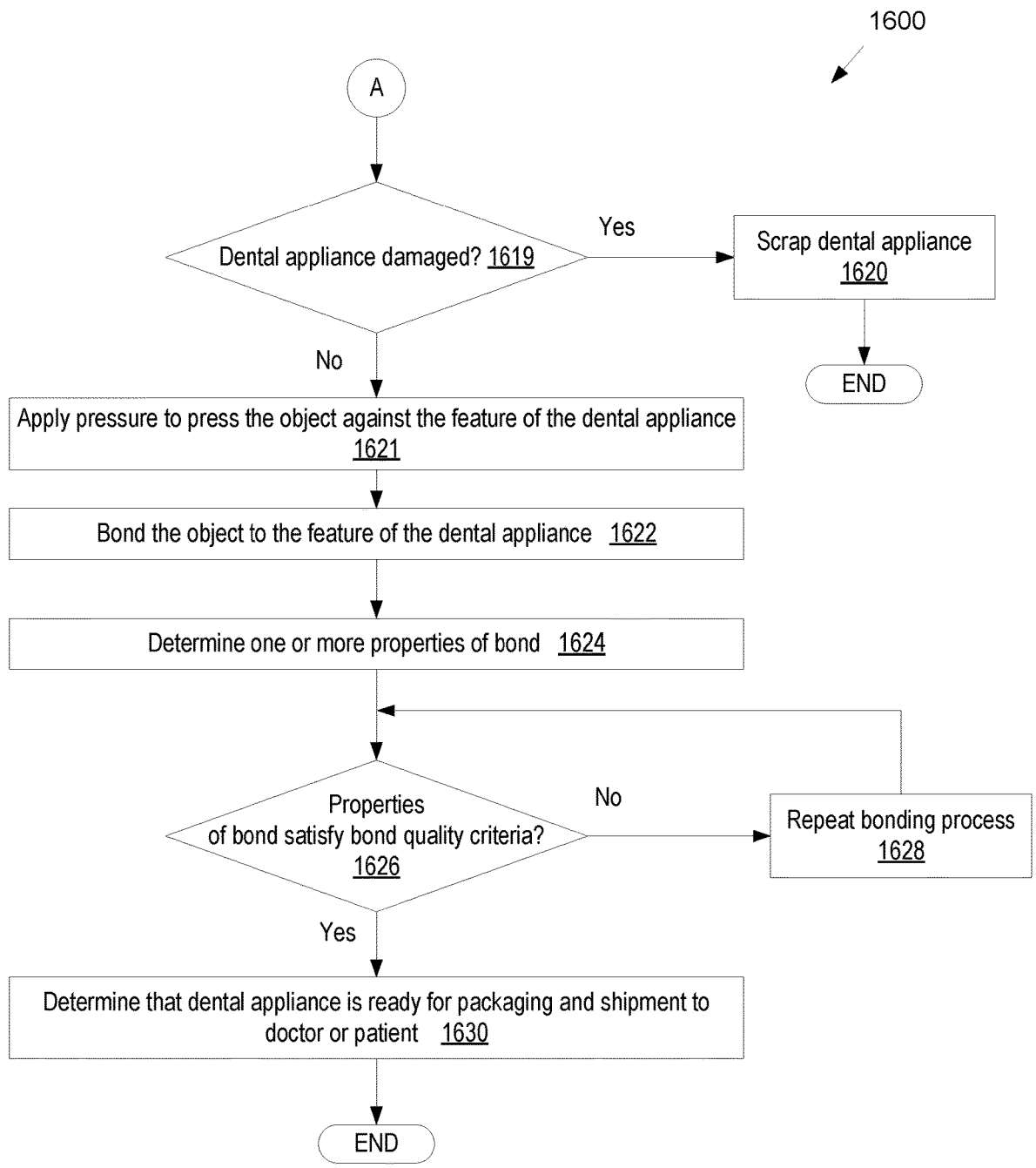

FIGS. 16A-B illustrate a flow diagram for a method 1600 of manufacturing a dental appliance and performing automated quality control of the manufactured dental appliance, in accordance with embodiments of the disclosure. Some operations of the methods may be performed by a processing logic that may comprise hardware (e.g., circuitry, dedicated logic, programmable logic, microcode, etc.), software (e.g., instructions run on a processing device to perform hardware simulation), or a combination thereof. The processing logic may execute on one or many processing devices (e.g., of computing device 1700 of FIG. 17). The processing logic may be processing logic of dental appliance assessor 1446 of FIG. 14 in embodiments. Some operations of method 1600 may be performed by a manufacturing system, which may include multiple inspection stations, a robot station and a bonding station in embodiments.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

At block 1602 of method 1600, the manufacturing system receives, at a holder, a feature of a dental appliance. The feature may include a first surface having a first shape. The holder may hold the feature of the dental appliance at a reference position.

At block 1604, an inspection station of the manufacturing system generates an image of the dental appliance in the holder, and processing logic processes the image to determine whether the appliance is correctly placed into the holder. In one embodiment, dental appliance placement assessor 1450 determines whether the dental appliance is properly placed in the holder based on processing of the image. If the dental appliance is correctly placed in the holder, the method continues to block 1608. If the dental appliance is incorrectly placed in the holder or is placed in an incorrect holder, the method continues to block 1606.

At block 1606, the dental appliance is repositioned in the holder or in a different holder. The method then returns to block 1604.

At block 1608, processing logic determines an appliance type of the dental appliance. In one embodiment, the image of the dental appliance in the holder is processed by processing logic to determine the appliance type. In one embodiment, object type selector 1456 determines the appliance type from the image.

At block 1610, processing logic may determine an object type to use from a plurality of object types, where the determined object type is associated with the appliance type. In one embodiment, object type selector 1456 determines the object type.

At block 1612, an object having the determined object type is picked up by a robot arm at a robot station. At block 1614, the robot arm places the object against the feature at the reference position. The object may have a second surface with a second shape that mates with the first shape of the feature.

At block 1616, processing logic determines whether the object was correctly placed against the feature of the dental appliance. In one embodiment, an inspection station generates an image of the object in the dental appliance and determined based on the image whether the object was correctly placed into or onto the feature of the dental appliance. In one embodiment, object placement assessor 1465 determines whether the object was correctly placed against the feature of the dental appliance. If the object was not correctly placed against the feature of the dental appliance, the method continues to block 1618, at which the robot arm may remove the object from the dental appliance and/or reposition the object against the feature of the dental appliance. The method may then return to block 1616. If at block 1616 a determination is made that the object was correctly placed, the method continues to block 1619.

At block 1619, processing logic processes the image of the object placed into or onto the feature to determine whether the dental appliance has been damaged during the manufacturing process (e.g., due to the placement of the object against the dental appliance). In one embodiment, dental appliance damage assessor 1465 processes the image to determine whether the dental appliance has been damaged. If the dental appliance has been damaged, then the method may continue to block 1620, at which the dental appliance may be scrapped. Processing logic may then mark or label the dental appliance for disposal in an inventory tracking database. If the dental appliance has not been damaged, then the method may proceed to block 1621.

At block 1621, processing logic applies pressure to press the object against the feature of the dental appliance at a bonding station. At block 1622, the feature is bonded to the dental appliance (e.g., via laser welding).

At block 1624, processing logic determines one or more properties of the bond. This may include generating an image of the bond (e.g., at an inspection station) and processing the image using processing logic. In one embodiment, the image is processed by bond assessor 1470, which outputs the one or more properties of the bond. At block 1626, processing logic (e.g., bond assessor 1470) determines whether the properties of the bond satisfy one or more bond quality criteria. If the properties of the bond fail to satisfy one or more bond quality criteria, then the method may proceed to block 1628, at which the bond process may be repeated. The method may then return to block 1626. If at block 1626 a determination is made that the bond satisfies the one or more bond quality criteria, the method proceeds to block 1630.

At block 1630, processing logic determines that the dental appliance is ready for packaging and shipment to a doctor or patient. The dental appliance may be marked or tagged for shipment in an inventory tracking database.

Figure 17:
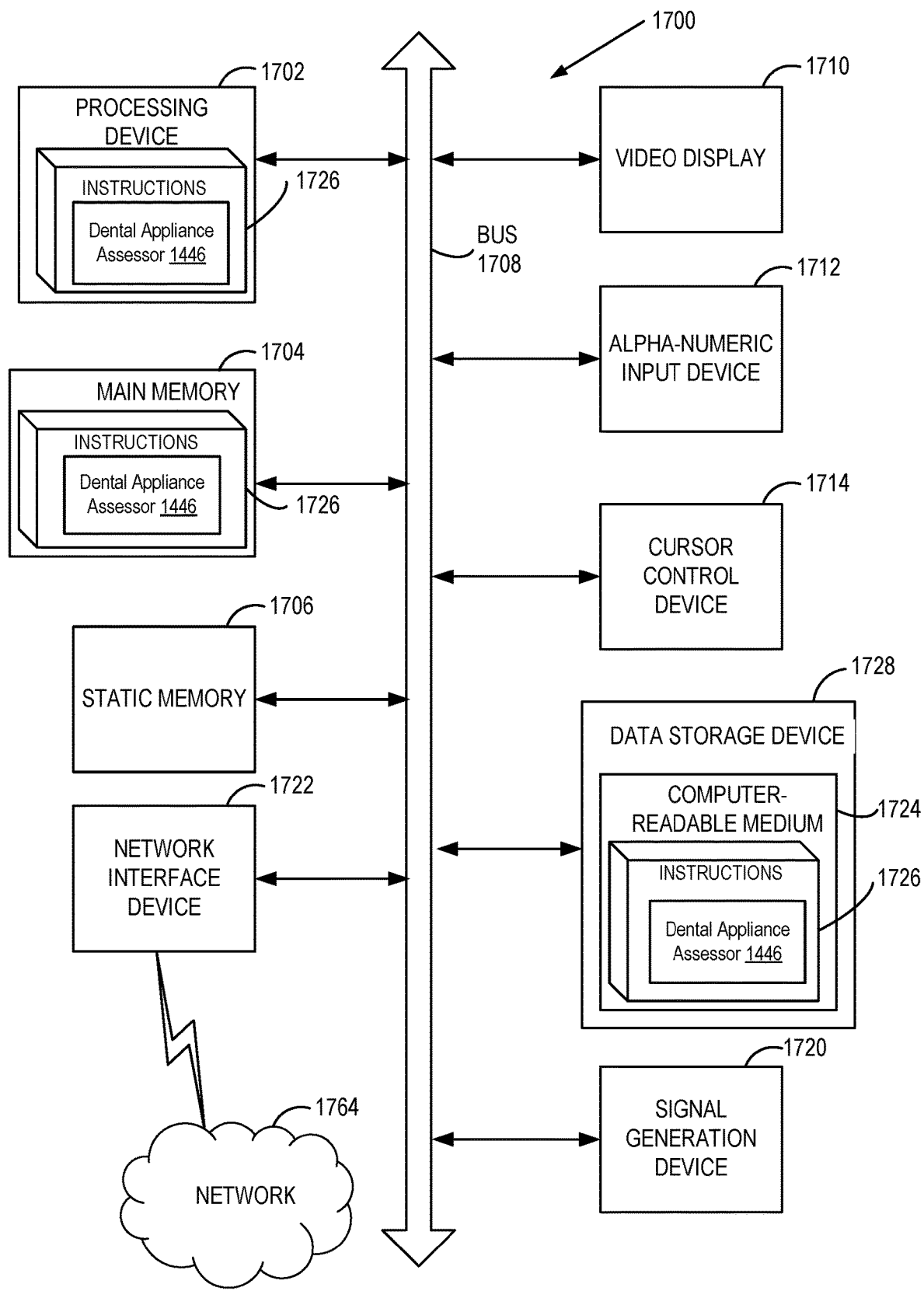
FIG. 17 illustrates a block diagram of an example computing device, in accordance with embodiments of the present disclosure.

FIG. 17 illustrates a diagrammatic representation of a machine in the example form of a computing device 1700 within which a set of instructions, for causing the machine to perform any one or more of the methodologies discussed herein above. In alternative embodiments, the machine may be connected (e.g., networked) to other machines in a Local Area Network (LAN), an intranet, an extranet, or the Internet. For example, the machine may be networked to a rapid prototyping apparatus such as a 3D printer or SLA apparatus. In another example, the machine may be networked to or directly connected to an imaging system, a robot arm, a laser welder, a bonding station, and so on. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1700 includes a processing device 1702, a main memory 1704 (e.g., read only memory (ROM), flash memory, dynamic random access memory (DRAM) such as synchronous DRAM (SDRAM), etc.), a static memory 1706 (e.g., flash memory, static random access memory (SRAM), etc.), and a secondary memory (e.g., a data storage device 1728), which communicate with each other via a bus 1708.

Processing device 1702 represents one or more general-purpose processors such as a microprocessor, central processing unit, or the like. More particularly, the processing device 1702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1702 may also be one or more special-purpose processing devices such as an application specific integrated circuit (ASIC), a field programmable gate array (FPGA), a digital signal processor (DSP), network processor, or the like. Processing device 1702 is configured to execute the processing logic (instructions 1726) for performing operations and steps discussed herein.

The computing device 1700 may further include a network interface device 1722 for communicating with a network 1764. The computing device 1700 also may include a video display unit 1710 (e.g., a liquid crystal display (LCD) or a cathode ray tube (CRT)), an alphanumeric input device 1712 (e.g., a keyboard), a cursor control device 1714 (e.g., a mouse), and a signal generation device 1720 (e.g., a speaker).

The data storage device 1728 may include a machine-readable storage medium (or more specifically a non-transitory computer-readable storage medium) 1724 on which is stored one or more sets of instructions 1726 embodying any one or more of the methodologies or functions described herein. A non-transitory storage medium refers to a storage medium other than a carrier wave. The instructions 1726 may also reside, completely or at least partially, within the main memory 1704 and/or within the processing device 1702 during execution thereof by the computer device 1700, the main memory 1704 and the processing device 1702 also constituting computer-readable storage media.

The computer-readable storage medium 1724 may also be used to store dental appliance assessor 1446 as described herein above, which may perform one or more of the operations of methods described above. The computer readable storage medium 1724 may also store a software library containing methods that call a dental appliance assessor 1446. While the computer-readable storage medium 1724 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media, and other non-transitory computer-readable media.

As discussed herein above, in some embodiments, the inspection stations may be used to perform automated defect detection of molds of dental arches used to manufacture aligners and/or to perform automated defect detection of dental appliances.

Figure 18:
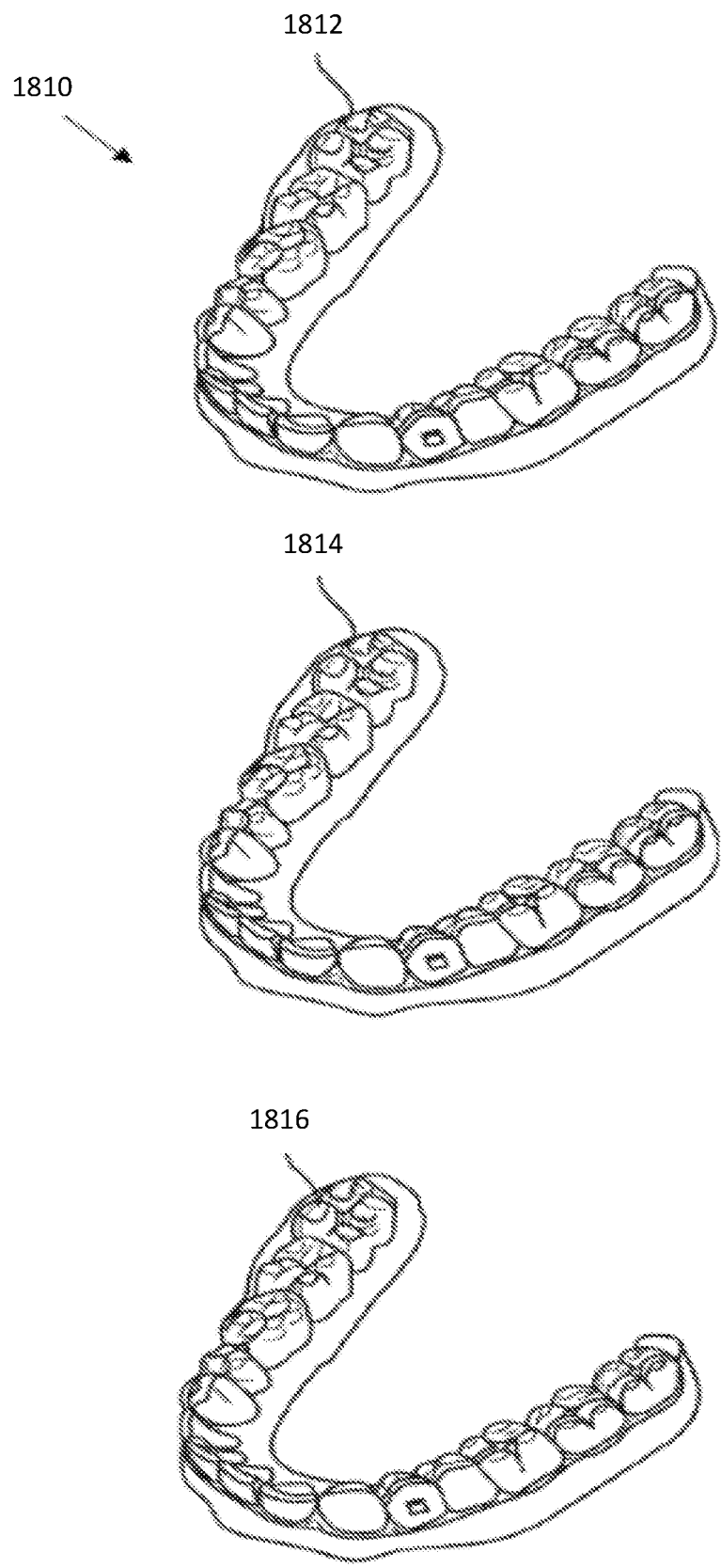
FIG. 18 illustrates a tooth repositioning system, in accordance with embodiments.

FIG. 18 illustrates a tooth repositioning system 1810 including a plurality of appliances 1812, 1814, and 1816. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1810 can include a first appliance 1812 corresponding to an initial tooth arrangement, one or more intermediate appliances 1814 corresponding to one or more intermediate arrangements, and a final appliance 1816 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

In some embodiments, the appliances 1812, 1814, 1816, or portions thereof, can be produced using indirect fabrication techniques, such as thermoforming over a positive or negative mold, which may be inspected using the methods and systems described herein above. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In an example of indirect fabrication, a mold of a patient's dental arch may be fabricated from a digital model of the dental arch, and a shell may be formed over the mold (e.g., by thermoforming a polymeric sheet over the mold of the dental arch and then trimming the thermoformed polymeric sheet). The fabrication of the mold may be formed by a rapid prototyping machine (e.g., a SLA 3D printer). The rapid prototyping machine may receive digital models of molds of dental arches and/or digital models of the appliances 1812, 1814, 1816 after the digital models of the appliances 1812, 1814, 1816 have been processed by processing logic of a computing device. The processing logic may include hardware (e.g., circuitry, dedicated logic, programming logic, microcode, etc.), software (e.g., instructions executed by a processing device), firmware, or a combination thereof.

To manufacture the molds, a shape of a dental arch for a patient at a treatment stage is determined based on a treatment plan. In the example of orthodontics, the treatment plan may be generated based on an intraoral scan of a dental arch to be molded. The intraoral scan of the patient's dental arch may be performed to generate a three dimensional (3D) virtual model of the patient's dental arch (mold). For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting technologies (e.g., to design the virtual 3D mold). Alternatively, an initial negative mold may be generated from an actual to be modeled (e.g., a dental impression or the like). The negative mold may then be scanned to determine a shape of a positive mold that will be produced.

Once the virtual 3D model of the patient's dental arch is generated, a dental practitioner may determine a desired treatment outcome, which includes final positions and orientations for the patient's teeth. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model will be different. The original virtual 3D model, the final virtual model 3D model and each intermediate virtual 3D model is unique and customized to the patient.

Accordingly, multiple different virtual 3D models (digital designs) of a dental arch may be generated for a single patient. A first virtual 3D model may be a unique model of a patient's dental arch and/or teeth as they presently exist, and a final virtual 3D may be a model of the patient's dental arch and/or teeth after correction of one or more teeth and/or a jaw. Multiple intermediate virtual 3D models may be modeled, each of which may be incrementally different from previous virtual 3D models.

Each virtual 3D model of a patient's dental arch may be used to generate customized physical mold of the dental arch at a particular stage of treatment. The shape of the mold may be at least in part based on the shape of the virtual 3D model for that treatment stage. The virtual 3D model may be represented in a file such as a computer aided drafting (CAD) file or a 3D printable file such as a stereolithography (STL) file. The virtual 3D model for the mold may be sent to a third party (e.g., clinician office, laboratory, manufacturing facility or other entity). The virtual 3D model may include instructions that will control a fabrication system or device in order to produce the mold with specific geometries.

A clinician office, laboratory, manufacturing facility or other entity may receive the virtual 3D model of the mold, the digital model having been created as set forth above. The entity may input the digital model into a rapid prototyping machine. The rapid prototyping machine then manufactures the mold using the digital model. One example of a rapid prototyping manufacturing machine is a 3D printer. 3D printing includes any layer-based additive manufacturing processes. 3D printing may be achieved using an additive process, where successive layers of material are formed in proscribed shapes. 3D printing may be performed using extrusion deposition, granular materials binding, lamination, photopolymerization, continuous liquid interface production (CLIP), or other techniques. 3D printing may also be achieved using a subtractive process, such as milling.

In some instances SLA is used to fabricate an SLA mold. In SLA, the mold is fabricated by successively printing thin layers of a photo-curable material (e.g., a polymeric resin) on top of one another. A platform rests in a bath of liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured.

Materials such as polyester, a co-polyester, a polycarbonate, a thermopolymeric polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermopolymeric elastomer (TPE), a thermopolymeric vulcanizate (TPV) elastomer, a polyurethane elastomer, a block copolymer elastomer, a polyolefin blend elastomer, a thermopolymeric co-polyester elastomer, a thermopolymeric polyamide elastomer, or combinations thereof, may be used to directly form the mold. The materials used for fabrication of the mold can be provided in an uncured form (e.g., as a liquid, resin, powder, etc.) and can be cured (e.g., by photopolymerization, light curing, gas curing, laser curing, crosslinking, etc.). The properties of the material before curing may differ from the properties of the material after curing.

After the mold is generated, it may be inspected using the systems and/or methods described herein above. If the mold passes the inspection, then it may be used to form an appliance (e.g., an aligner).

Appliances may be formed from each mold and when applied to the teeth of the patient, may provide forces to move the patient's teeth as dictated by the treatment plan. The shape of each appliance is unique and customized for a particular patient and a particular treatment stage. In an example, the appliances 1812, 1814, and 1816 can be pressure formed or thermoformed over the molds. Each mold may be used to fabricate an appliance that will apply forces to the patient's teeth at a particular stage of the orthodontic treatment. The appliances 1812, 1814, and 1816 each have teeth-receiving cavities that receive and resiliently reposition the teeth in accordance with a particular treatment stage.

In one embodiment, a sheet of material is pressure formed or thermoformed over the mold. The sheet may be, for example, a sheet of polymeric (e.g., an elastic thermopolymeric, a sheet of polymeric material, etc.). To thermoform the shell over the mold, the sheet of material may be heated to a temperature at which the sheet becomes pliable. Pressure may concurrently be applied to the sheet to form the now pliable sheet around the mold. Once the sheet cools, it will have a shape that conforms to the mold. In one embodiment, a release agent (e.g., a non-stick material) is applied to the mold before forming the shell. This may facilitate later removal of the mold from the shell.

Additional information may be added to the appliance. The additional information may be any information that pertains to the aligner. Examples of such additional information includes a part number identifier, patient name, a patient identifier, a case number, a sequence identifier (e.g., indicating which aligner a particular liner is in a treatment sequence), a date of manufacture, a clinician name, a logo and so forth. For example, after an appliance is thermoformed, the aligner may be laser marked with a part number identifier (e.g., serial number, barcode, or the like). In some embodiments, the system may be configured to read (e.g., optically, magnetically, or the like) an identifier (barcode, serial number, electronic tag or the like) of the mold to determine the part number associated with the aligner formed thereon. After determining the part number identifier, the system may then tag the aligner with the unique part number identifier. The part number identifier may be computer readable and may associate that aligner to a specific patient, to a specific stage in the treatment sequence, whether it is an upper or lower shell, a digital model representing the mold the aligner was manufactured from and/or a digital file including a virtually generated digital model or approximated properties thereof of that aligner (e.g., produced by approximating the outer surface of the aligner based on manipulating the digital model of the mold, inflating or scaling projections of the mold in different planes, etc.).

After an appliance is formed over a mold for a treatment stage, that appliance is subsequently trimmed along a cutline (also referred to as a trim line) and the appliance may be removed from the mold. The processing logic may determine a cutline for the appliance. The determination of the cutline(s) may be made based on the virtual 3D model of the dental arch at a particular treatment stage, based on a virtual 3D model of the appliance to be formed over the dental arch, or a combination of a virtual 3D model of the dental arch and a virtual 3D model of the appliance. The location and shape of the cutline can be important to the functionality of the appliance (e.g., an ability of the appliance to apply desired forces to a patient's teeth) as well as the fit and comfort of the appliance. For shells such as orthodontic appliances, orthodontic retainers and orthodontic splints, the trimming of the shell may play a role in the efficacy of the shell for its intended purpose (e.g., aligning, retaining or positioning one or more teeth of a patient) as well as the fit on a patient's dental arch. For example, if too much of the shell is trimmed, then the shell may lose rigidity and an ability of the shell to exert force on a patient's teeth may be compromised. When too much of the shell is trimmed, the shell may become weaker at that location and may be a point of damage when a patient removes the shell from their teeth or when the shell is removed from the mold. In some embodiments, the cut line may be modified in the digital design of the appliance as one of the corrective actions taken when a probable point of damage is determined to exist in the digital design of the appliance.

On the other hand, if too little of the shell is trimmed, then portions of the shell may impinge on a patient's gums and cause discomfort, swelling, and/or other dental issues. Additionally, if too little of the shell is trimmed at a location, then the shell may be too rigid at that location. In some embodiments, the cutline may be a straight line across the appliance at the gingival line, below the gingival line, or above the gingival line. In some embodiments, the cutline may be a gingival cutline that represents an interface between an appliance and a patient's gingiva. In such embodiments, the cutline controls a distance between an edge of the appliance and a gum line or gingival surface of a patient.

Each patient has a unique dental arch with unique gingiva. Accordingly, the shape and position of the cutline may be unique and customized for each patient and for each stage of treatment. For instance, the cutline is customized to follow along the gum line (also referred to as the gingival line). In some embodiments, the cutline may be away from the gum line in some regions and on the gum line in other regions. For example, it may be desirable in some instances for the cutline to be away from the gum line (e.g., not touching the gum) where the shell will touch a tooth and on the gum line (e.g., touching the gum) in the interproximal regions between teeth. Accordingly, it is important that the shell be trimmed along a predetermined cutline.

In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances 1812, 1814, and 1816. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances 1812, 1814, and 1816 can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances 1812, 1814, and 1816 can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances 1812, 1814, and 1816. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances 1812, 1814, and 1816 are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every nth build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, and then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Once appliances (e.g., aligners) are directly fabricated, they may be inspected using the systems and/or methods described herein above.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 19:
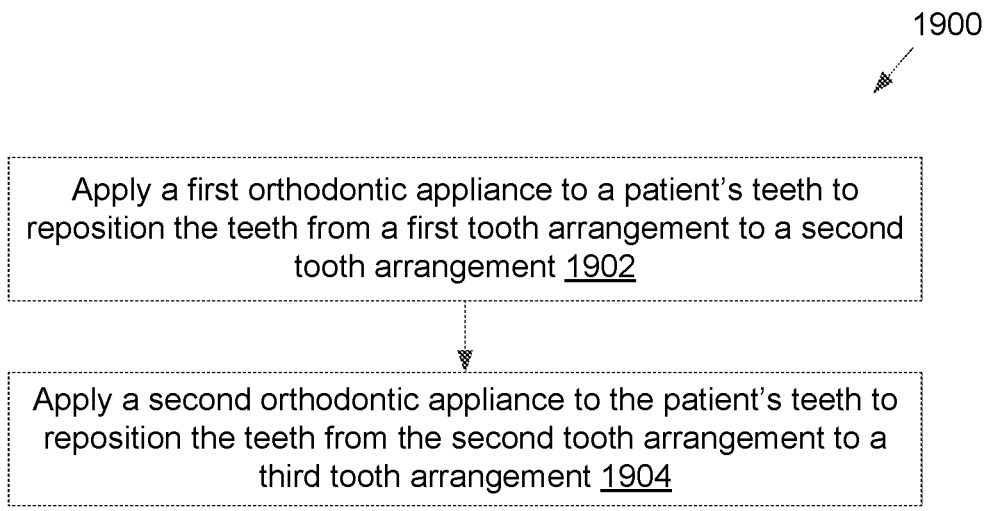
FIG. 19 illustrates a method of orthodontic treatment using a plurality of appliances, in accordance with embodiments.

FIG. 19 illustrates a method 1900 of orthodontic treatment using a plurality of appliances, in accordance with embodiments. The method 1900 can be practiced using any of the appliances or appliance sets described herein. In block 1902, a first orthodontic appliance is applied to a patient's teeth in order to reposition the teeth from a first tooth arrangement to a second tooth arrangement. In block 1904, a second orthodontic appliance is applied to the patient's teeth in order to reposition the teeth from the second tooth arrangement to a third tooth arrangement. The method 1900 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 20:
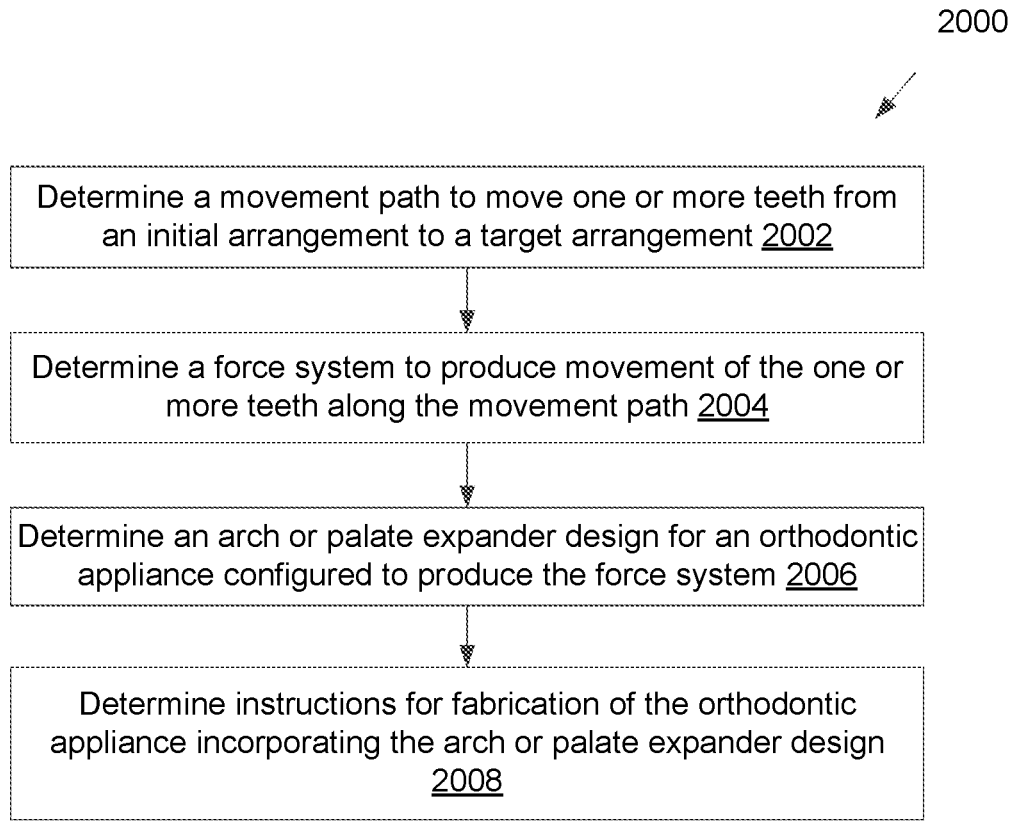
FIG. 20 illustrates a method for designing an orthodontic appliance to be produced by direct fabrication, in accordance with embodiments.

FIG. 20 illustrates a method 2000 for designing an orthodontic appliance to be produced by direct fabrication, in accordance with embodiments. The method 2000 can be applied to any embodiment of the orthodontic appliances described herein. Some or all of the blocks of the method 2000 can be performed by any suitable data processing system or device, e.g., one or more processors configured with suitable instructions.

In block 2002, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 2004, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In block 2006, an orthodontic appliance configured to produce the force system is determined. Determination of the orthodontic appliance, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA(Abaqus) software products from Dassault Systèmes of Waltham, MA.

Optionally, one or more orthodontic appliances can be selected for testing or force modeling. As noted above, a desired tooth movement, as well as a force system required or desired for eliciting the desired tooth movement, can be identified. Using the simulation environment, a candidate orthodontic appliance can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In block 2008, instructions for fabrication of the orthodontic appliance incorporating the orthodontic appliance are generated. The instructions can be configured to control a fabrication system or device in order to produce the orthodontic appliance with the specified orthodontic appliance. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 2000 may comprise additional blocks: 1) The upper arch and palate of the patient is scanned intraorally to generate three dimensional data of the palate and upper arch; 2) The three dimensional shape profile of the appliance is determined to provide a gap and teeth engagement structures as described herein.

Although the above blocks show a method 2000 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 2000 may be performed with any suitable fabrication system or device, such as the embodiments described herein. Some of the blocks may be optional, and the order of the blocks can be varied as desired.

Figure 21:
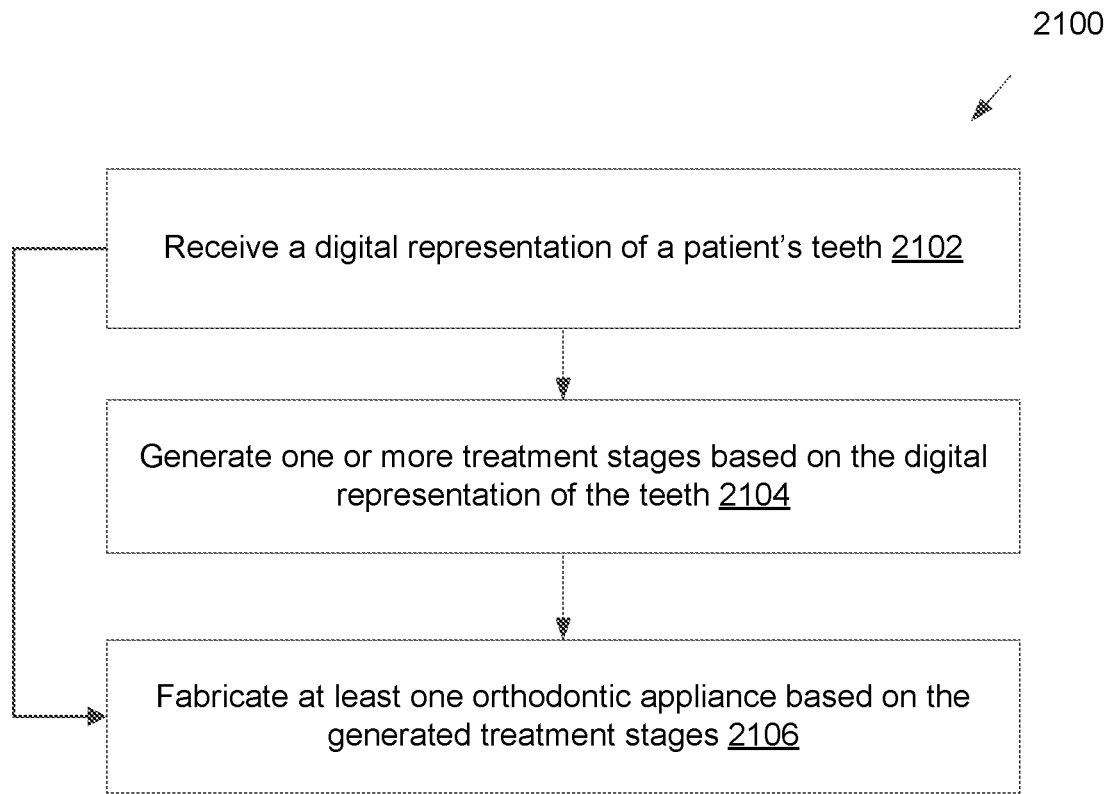
FIG. 21 illustrates a method for digitally planning an orthodontic treatment, in accordance with embodiments.

FIG. 21 illustrates a method 2100 for digitally planning an orthodontic treatment and/or design or fabrication of an appliance, in accordance with embodiments. The method 2100 can be applied to any of the treatment procedures described herein and can be performed by any suitable data processing system.

In block 2110, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 2102, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 2104, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. Design and/or fabrication of an orthodontic appliance, and perhaps a particular orthodontic treatment, may include use of a representation of the patient's teeth (e.g., receive a digital representation of the patient's teeth), followed by design and/or fabrication of an orthodontic appliance based on a representation of the patient's teeth in the arrangement represented by the received representation.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or." When the term "about" or "approximately" is used herein, this is intended to mean that the nominal value presented is precise within ±10%.

Although the operations of the methods herein are shown and described in a particular order, the order of operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. In one embodiment, multiple metal bonding operations are performed as a single step.

It is understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A method of manufacturing a dental appliance, comprising:
    receiving, at a holder, a feature of the dental appliance, the feature comprising a first surface having a first shape, wherein the holder holds the feature of the dental appliance at a reference position;
    capturing an image of the dental appliance in the holder prior to placing an object against the feature of the dental appliance;
    processing the image;
    determining whether the dental appliance has a correct placement in the holder based on a result of the processing;
    automatically placing the object against the feature at the reference position using a robot arm, wherein the object comprises a second surface having a second shape that mates with the first shape;
    applying pressure to press the object against the feature of the dental appliance; and
    bonding the object to the feature of the dental appliance while applying the pressure.

2. The method of claim 1, further comprising performing the following prior to receiving the feature of the dental appliance at the holder:
    performing three-dimensional printing to print a mold for the dental appliance;
    thermoforming the dental appliance over the mold;
    trimming the dental appliance along a trim line; and
    removing the dental appliance from the mold.

3. The method of claim 1, wherein the dental appliance comprises an orthodontic aligner, the method further comprising performing the following before placing the object against the feature of the orthodontic aligner:
    determining an aligner type of the orthodontic aligner;
    determining an object type to use from a plurality of object types, wherein the object type is associated with the aligner type; and
    automatically picking up the object having the object type using the robot arm.

4. The method of claim 3, wherein determining the aligner type comprises:
    capturing an image of the feature; and
    processing the image.

5. The method of claim 4, wherein:
    the feature comprises a pattern of notches and/or protrusions associated with the aligner type, wherein processing of the image is performed to identify the pattern of notches and/or protrusions of the feature, and wherein the object having the object type comprises an opposing pattern of notches and/or protrusions that mates with the pattern of notches and/or protrusions of the feature for the aligner type.

6. The method of claim 1, wherein processing the image comprises inputting the image into a trained machine learning model, wherein the trained machine learning model generates an output indicating whether the dental appliance has the correct placement in the holder.

7. The method of claim 1, wherein bonding the object to the feature comprises laser welding the object to the feature.

8. The method of claim 7, wherein the object comprises a layer of a photo-thermal compound on the second surface of the object, wherein at least one of a) the dental appliance is a clear plastic dental appliance or b) the object is a clear plastic object, and wherein performing the laser welding comprises:
directing coherent light having a first wavelength through at least one of the clear plastic dental appliance or the clear plastic object onto an interface of the first surface and the second surface, wherein the photo-thermal compound absorbs the coherent light having the first wavelength and generates heat that melts the object and the dental appliance at the interface of the first surface and the second surface.

9. The method of claim 7, wherein the object comprises plastic impregnated with a photo-thermal compound, wherein the dental appliance is a clear plastic orthodontic aligner, and wherein performing the laser welding comprises:
directing coherent light having a first wavelength through the clear plastic orthodontic aligner onto an interface of the first surface and the second surface, wherein the photo-thermal compound at the second surface absorbs the coherent light having the first wavelength and generates heat that melts the object and the dental appliance at the interface of the first surface and the second surface.

10. A method of manufacturing an orthodontic aligner, comprising:
receiving, at a holder, a feature of the orthodontic aligner, the feature comprising a first surface having a first shape, wherein the holder holds the feature of the orthodontic aligner at a reference position;
determining an aligner type of the orthodontic aligner, wherein determining the aligner type comprises:
capturing an image of the feature; and
inputting the image into a trained machine learning model, wherein the trained machine learning model outputs a classification for the orthodontic aligner that indicates the aligner type;
determining an object type to use from a plurality of object types, wherein the object type is associated with the aligner type;
automatically picking up an object having the object type using a robot arm;
automatically placing the object against the feature at the reference position using the robot arm, wherein the object comprises a second surface having a second shape that mates with the first shape;
applying pressure to press the object against the feature of the orthodontic aligner; and
bonding the object to the feature of the orthodontic aligner while applying the pressure.

11. A method of manufacturing a dental appliance, comprising:
receiving, at a holder, a feature of the dental appliance, the feature comprising a first surface having a first shape, wherein the holder holds the feature of the dental appliance at a reference position;
automatically placing an object against the feature at the reference position using a robot arm, wherein the object comprises a second surface having a second shape that mates with the first shape;
capturing an image of the dental appliance in the holder prior to bonding the object to the dental appliance;
processing the image;
determining whether the object is correctly placed against the feature of the dental appliance based on a result of the processing;
applying pressure to press the object against the feature of the dental appliance; and
bonding the object to the feature of the dental appliance while applying the pressure.

12. The method of claim 11, wherein processing the image comprises inputting the image into a trained machine learning model, wherein the trained machine learning model generates an output indicating at least one of a) whether the object was correctly placed against the feature of the dental appliance, or b) whether the object is a correct object type for placement against the feature of the dental appliance.

13. A method of manufacturing a dental appliance, comprising:
receiving, at a holder, a feature of the dental appliance, the feature comprising a first surface having a first shape, wherein the holder holds the feature of the dental appliance at a reference position;
automatically placing an object against the feature at the reference position using a robot arm, wherein the object comprises a second surface having a second shape that mates with the first shape;
measuring an amount of force applied to place the object against the feature of the dental appliance during the placing of the object against the feature of the dental appliance;
determining whether the amount of force is between an upper force threshold and a lower force threshold;
determining whether the object has been correctly placed against the feature of the dental appliance based on whether the amount of force is between the upper force threshold and the lower force threshold;
applying pressure to press the object against the feature of the dental appliance; and
bonding the object to the feature of the dental appliance while applying the pressure.

14. The method of claim 13, wherein the feature comprises a cavity having a narrower opening at a top of the cavity than at a bottom of the cavity, wherein placing the object against the feature causes walls of the cavity to flex outward, and wherein the walls of the cavity return to an unflexed position once the object is fully seated against the feature.

15. The method of claim 13, wherein bonding the object to the feature comprises at least one of a) applying heat to activate a thermally activated solvent on the second surface of the object that forms the bond or b) exposing the dental appliance to ultraviolet radiation to cure an ultraviolet cured adhesive on the second surface of the object to form the bond.

16. A method of manufacturing a dental appliance, comprising:
receiving, at a holder, a feature of the dental appliance, the feature comprising a first surface having a first shape, wherein the holder holds the feature of the dental appliance at a reference position;
manufacturing an object comprising a second surface having a second shape that mates with the first shape, wherein the second surface of the object that mates with the first surface of the feature has a first average surface roughness that causes the second surface to have a target wettability, and wherein a third surface of the object that does not contact the dental appliance has a second average surface roughness that is lower than the first average surface roughness, wherein the second average surface roughness reduces at least one of absorbance or reflectance of the object to light;

coating the second surface of the object with a bonding layer, wherein the first average surface roughness facilitates an even coating of the bonding layer on second surface;

automatically placing the object against the feature at the reference position using a robot arm;

applying pressure to press the object against the feature of the dental appliance; and bonding the object to the feature of the dental appliance while applying the pressure.

17. A method of manufacturing a clear plastic dental appliance, comprising:

manufacturing an object configured to fit into a cavity of a clear plastic dental appliance, wherein the cavity comprises a first surface having a first shape, wherein the object comprises a second surface having a second shape that mates with the first surface of the cavity and that has a first average surface roughness that causes the second surface to have a target wettability, and wherein a third surface of the object that does not contact the clear plastic dental appliance has a second average surface roughness that is lower than the first average surface roughness, wherein the second average surface roughness reduces at least one of absorbance or reflectance of the object to coherent light used to perform laser welding;

coating the second surface of the object with a photo-thermal compound, wherein the first average surface roughness facilitates an even coating of the photo-thermal compound on the second surface;

disposing the object within the cavity of the clear plastic dental appliance;

applying pressure to press the object against the cavity of the clear plastic dental appliance; and laser welding the object to the cavity of the clear plastic dental appliance while applying the pressure.

18. The method of claim 17, further comprising:
forming the clear plastic dental appliance;
wherein disposing the object within the cavity comprises inserting the object into the cavity of the clear plastic dental appliance after the clear plastic dental appliance has been formed.

19. The method of claim 17, wherein forming the clear plastic dental appliance comprises thermoforming the clear plastic dental appliance over a mold.

20. The method of claim 17, wherein the object comprises a layer of a photo-thermal compound on the second surface of the object, wherein the object is a clear plastic object, and wherein performing the laser welding comprises:

directing coherent light having a first wavelength through the clear plastic object onto an interface of the first surface and the second surface, wherein the photo-thermal compound absorbs the coherent light having the first wavelength and generates heat that melts the object and the clear plastic dental appliance at the interface of the first surface and the second surface.

21. The method of claim 17, further comprising:
forming a mold for the clear plastic dental appliance, wherein the mold comprises an object configured to separate from the mold;

thermoforming the clear plastic dental appliance over the mold, wherein the cavity forms over the mold during the thermoforming;

trimming the clear plastic dental appliance along a trim line; and removing the clear plastic dental appliance from the mold, wherein the object is retained within the cavity and separates from the mold during removal of the clear plastic dental appliance from the mold.

* * * * *